United States Patent [19]
Boutillon et al.

[11] Patent Number: 5,993,823
[45] Date of Patent: Nov. 30, 1999

[54] CYTOTOXIC T LYMPHOCYTE-INDUCING LIPOPEPTIDES AND METHODS OF USE

[75] Inventors: Christophe Boutillon, Lille; Frederic Martinon, Montrouge; Christian Sergheraert, Morbecque; Remy Magne, L'Etang la Ville; Helene Gras-Masse, Merignies; Elisabeth Gomard, Paris; Andre Tartar, Vitry En Artois; Jean-Paul Levy, Paris, all of France

[73] Assignee: Institut Pasteur de Lille, France

[21] Appl. No.: 08/477,420

[22] Filed: Jun. 7, 1995

Related U.S. Application Data

[63] Continuation-in-part of application No. 08/477,419, Jun. 7, 1995, abandoned, which is a continuation-in-part of application No. 07/810,722, Dec. 18, 1991, abandoned.

[30] Foreign Application Priority Data

Dec. 18, 1990 [FR] France .................... 90 15870

[51] Int. Cl.⁶ .................... A61K 39/21; A61K 39/12; A61K 39/38; C07K 17/00
[52] U.S. Cl. .................... 424/208.1; 424/188.1; 424/184.1; 424/704.1; 530/350
[58] Field of Search .................... 424/208.1, 188.1, 424/184.1, 204.1; 530/350

[56] References Cited

U.S. PATENT DOCUMENTS 5,084,441  1/1992  Shaw et al. .................... 514/2

OTHER PUBLICATIONS

Butini, et al.: Comparative analysis of HIV–specific . . . Z:J Cell. Boi.: Supp. 18B; J 306, 1994.
Deres, et al. :In vivo priming of virus–specific cytotoxic t lymphocytes . . . :Nature: vol. 342: pp. 561–564, 1989.
Culmann, et al.: An antigenic peptide of the HIV–1 NEF protein . . . :Eur. J. Immunol.: 19: pp. 2383–2386, 1989.
Haynes, et al. : Toward an understanding of the correlates . . . : Science: vol. 271: pp. 324–328, Jan. 1996.

*Primary Examiner*—Frank C. Eisenschenk
*Assistant Examiner*—Brett Nelson
*Attorney, Agent, or Firm*—Bierman, Muserlian and Lucas

[57] ABSTRACT

Cytotoxic lymphocyte-inducing lipopeptides comprising a peptide fragment having approximately between 10 and 40 amino acids and comprising at least one antigenic determinant and also comprising one or more chains derived from fatty acids and one or more modified steroid groups useful for immunizing a human or animal body against pathogenic agents such as viruses or parasites which fragment is preferably a fragment of the protein encoded by the ENV gene, by the NEF gene or by the GAG gene of HIV viruses.

17 Claims, 13 Drawing Sheets

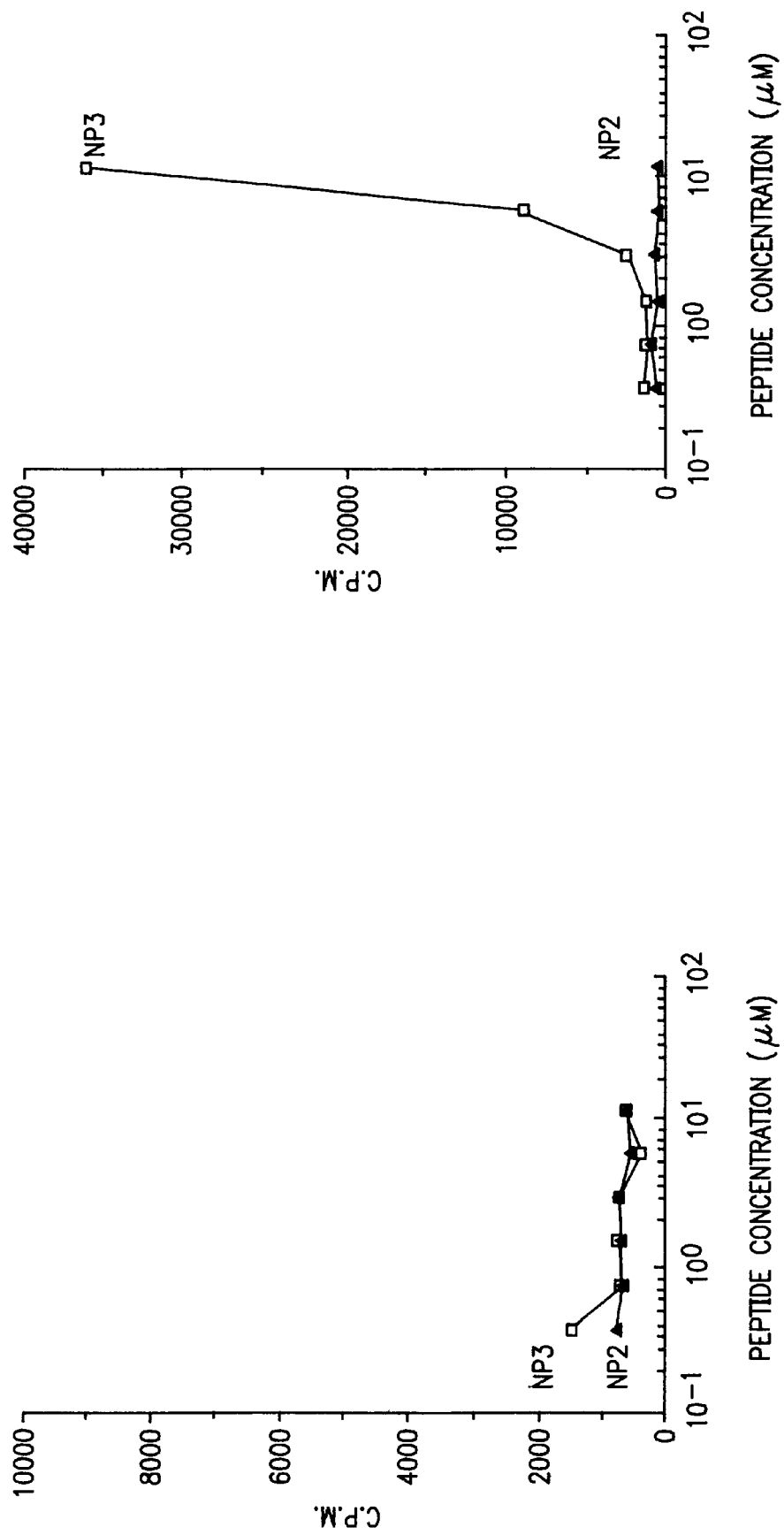

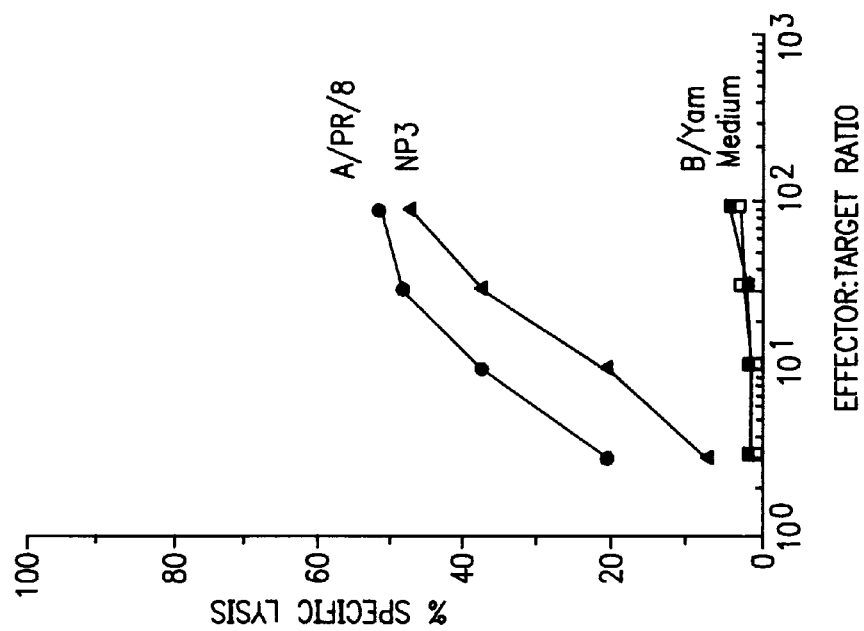
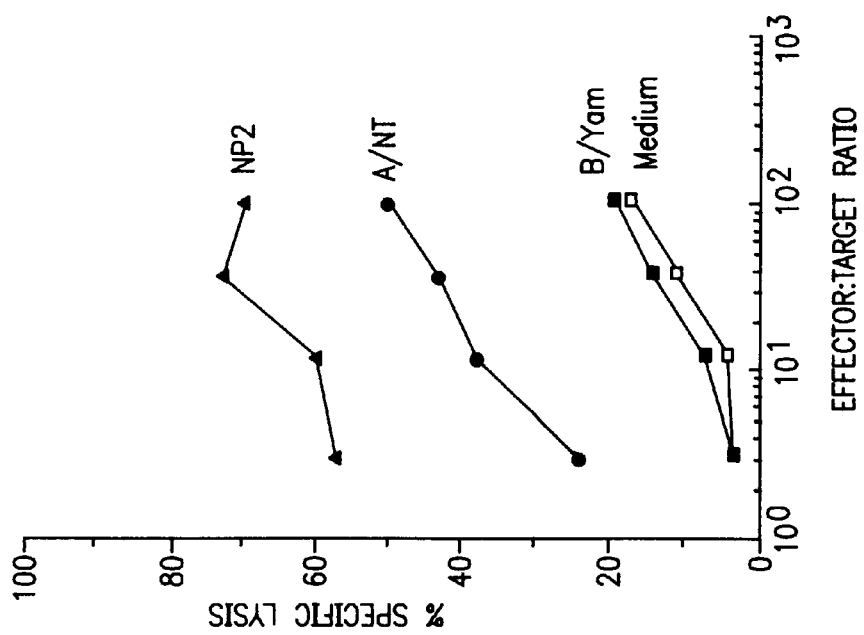
FIG. 11B
FIG. 11A

CYTOTOXIC T LYMPHOCYTE-INDUCING LIPOPEPTIDES AND METHODS OF USE

PRIOR APPLICATIONS

This application is a continuation-in-part of U.S. patent application Ser. No. 477,419 filed May 31, 1994 which is a continuation-in-part of U.S. patent application Ser. No. 810,722 filed Dec. 18, 1991, now abandoned.

FIELD OF THE INVENTION

The subject of the present invention is novel cytotoxic T lymphocyte-inducing lipopeptides.

The subject is furthermore the use of such lipopeptides as vaccines.

DESCRIPTION OF THE PRIOR ART

Most vaccines used induce a response through antibodies; However, it has been shown that cytotoxic lymphocytes can effectively protect mice against various pathogenic microorganisms (Skehel et al., Proc. Natl. Acad. Sci. USA. 1982, 79; 968; Lukacher et al., Exp. Med. 1984, 160: 814). This has also been shown for human cytotoxic T lymphocytes raised against cytomegaloviruses (Quinnan et al., N. Engl. J. Med. 1982, 307: 7; Rook et al., Am. J. Med. 1984, 76: 385). However, little is known about inducing immunity due to lymphocytes.

Some authors have tried to induce cytotoxic T lymphocytes (CTL) in vivo using peptides derived from ovalbumin (Carbone et al. J. Exp. Med. 169: 603, Ishioka et al. 1989, J. Immunol. 143:1094). These authors obtained immunizations, but these results are specific for peptides derived from ovalbumin.

AICHELE et al. ((1990) J. Exp. Med. 171:1815) succeeded, for their part, in inducing a cytolytic T response by repeated injections in vivo of a synthetic peptide in emulsion in incomplete Freund's adjuvant. These authors do not indicate the importance of the adjuvant under their immunization conditions. However, they suggest that an adjuvant is necessary for obtaining such a response.

The application EP-203,676 relates to a vaccine intended to induce a T cell mediated response, comprising some peptide-fatty acid conjugates. The fatty acid which is used is the palmitic acid. However, this vaccine comprises also Freund's adjuvant.

To the knowledge of the applicant, only DERES et al. (Nature, Volume 342, 30 Nov. 1989) pp. 561 to 564, have described the use of a synthetic lipopeptide to induce cytotoxic T lymphocytes (CTL) in vivo. In this article, the NP 147-158 SEQ ID NO:1 fragment of a nucleoprotein of the influenza virus is coupled to tripalmitoyl-S-glycerylcysteinylserylserine (P3CSS). It is shown that the NP 147-158 peptide-P3CSS lipid conjugate induces a CTL response against target cells infected by the influenza virus, whereas mice immunized with the NP 147-158 peptide alone or with the Ser Ser-NP 147-158 peptide do not generate cytotoxic T lymphocytes against this virus.

It should also be noted that lipopeptides have already been used to induce immunological reactions to specific antigens, but the responses generated implied the synthesis of antibodies and not T lymphocyte responses. HOPP (Molecular Immunology, 21, 13–16, 1984) has shown that antibodies raised against a determinant of the hepatitis B virus could be obtained by immunizing rabbits using a molecule consisting of a peptide of 15 amino acids corresponding to the antigenic determinant of the hepatitis B virus and of a pseudolipide residue, dipalmitoyl lysine.

The application EP-93 851 describes some lipopeptides comprising a peptidic sequence of 6 to 15 aminoacids bound to a lipophylic part. This lipophylic part can be a fatty acid such as palmitic, stearic, behenic, oleic or mycolic acids. It is mentioned that these lipopeptides induce the antibodies synthesis.

The publication of Wiesmuller et al. (Vaccine, volume 7, n°, 29–33, 1989) describes the use of a lipopeptide comprising a part of the sequence of the virus FDMV ($VP_1$) and the lipid $P_3CSS$ to induce the synthesis of antibodies.

The abstract of the publication of Jacob et al. (Chemical Abstracts, vol. 104, n°21, 472, abstract 184.455 x, 1986) relates to the induction of the antibodies synthesis by a lipopeptide comprising the tetanus toxine bound to a dipalmitoyl rest.

The abstract of the publication of Watari et al. (Chemical Abstracts, vol. 106, p 516, abstract n° 154 381 u, 1987) relates to the use of some peptides corresponding to the N-terminal region of the glycoprotein D of the virus HSV coupled to the palmitic acid. It is clearly indicated that there is induction of a T cells mediated response but that this response is not due to cytotoxic T lymphocytes.

Two other references relate to the synthesis and the structural study of lipopeptides.

The International Application WO 89 10348 relates to some fatty acids derivated lipopeptides, such as the aminoeicosanic, aminodecanoic, aminotetradecanoic, bromodecanoid and bromododecanoic acids.

It is mentioned that these compounds can be used as adjuvants and as carriers for vaccines, but without providing any mean to use these compounds.

The abstract of the publication of Mercy et al. (Chemical Abstracts, vol. 106, n°25, 264, abstract n°209,643 p, 1987) concerns the structural analysis of a lipopeptide composed of a fragment of the virus G protein and of a lysine-palmitoyl rest.

Besides, the U.S. application Ser. No. 628,596 relates to polypeptidic structures comprising an amino sequence taken in two regions of the NEF proteins corresponding to residues 73-94 and 113-147. However, the structure of the lipidic moiety is not disclosed and the application does not include any results concerning the use of such lipopeptides.

This analysis of the state of the art therefore shows that no technology applicable to various types of antigenic determinants has been developed which enables the induction of cytotoxic T lymphocytes to be obtained, with a high induced response, and which does not require the administration of an adjuvant.

GENERAL DESCRIPTION OF THE INVENTION

The applicant has shown, surprisingly, that a response of cytotoxic T lymphocytes against an antigen could be induced in a host organism by immunizing said organism with a lipopeptide complex containing one of the determinants of this antigen.

Even more surprisingly, the applicant has shown that this induction could be obtained for a large number of antigenic determinants of various pathogenic agents.

The subject of the present invention is therefore a lipopeptide comprising a peptide part having between 10 and 40 and preferably between 10 and 20 amino acids approximately and comprising at least one antigenic determinant, said lipopeptide also comprising one or more chains derived from fatty acids comprising between 10 and 20 carbon atoms and/or one or more steroid groups modified and coupled on the $\alpha$-$NH_2$ or $\epsilon$-NH2 functional groups of said amino acids.

Said fatty acid derivatives may be in particular hexadecanoic acid, 2-aminohexadecanoic acid (D,L) of the following formula (I):
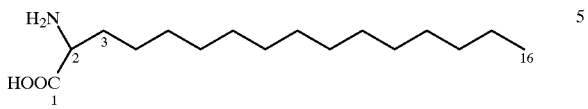
N-ε-palmitoyllysine (L) of the following formula (II):
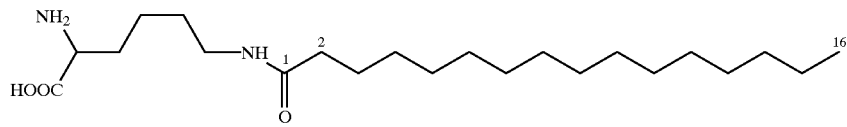
or its derivate having the following formula:
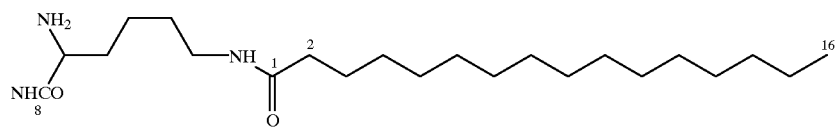
N,N'-dipalmitoyllysine (L) of the following formula (III):
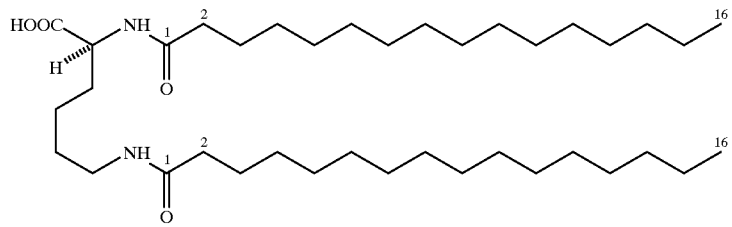
pimelautide of the following formula (IV):
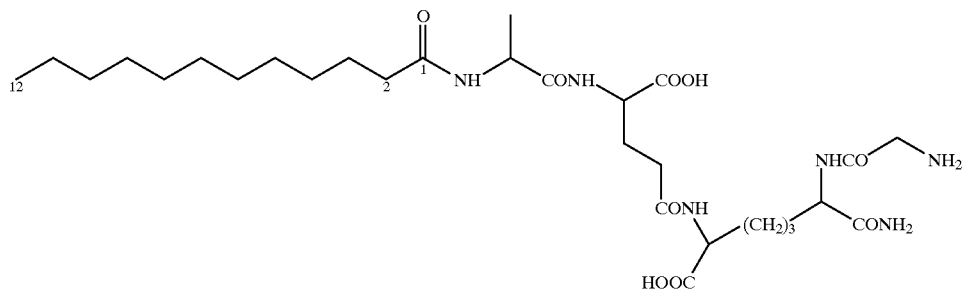
trimexautide of the following formula (V):

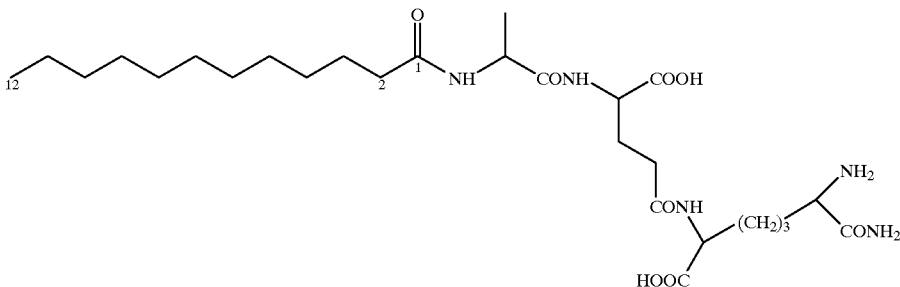

or one of their derivatives. Said steroid groups may be N-ε-[(cholest-5-enyl-3-oxy)acetyl]lysine (L) of the following formula (VI):

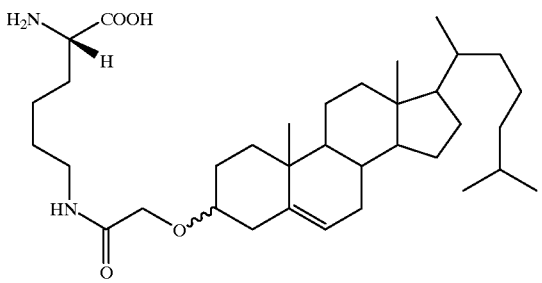

(cholest-5-enyl-3-oxy)acetic acid of the following formula (VII)

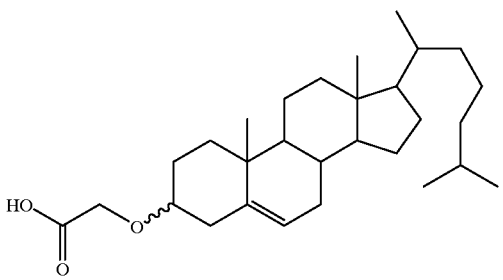

or one of their derivatives.

The peptide part may be a fragment of any protein derived from a pathogenic agent possessing an antigenic determinant.

Such proteins may be especially the proteins of the HIV1 or HIV2 virus, in particular the protein encoded by the ENV gene. In this case, the fragments 312-327 SEQ ID NO:2, 302-336 SEQ ID NO:3 or 307-331 SEQ ID NO:4 may be advantageously used depending on the HIV$_1$-BRU sequence (Hyers, C. A. B. Rabson, S. F. Josephs, T. F. Smith and E. Wong-Staal (Eds.), 1989, Human retrovirus and AIDS, Los Alamos Laboraty II:59) of this protein, to form the conjugated lipopeptide molecule.

Such fragments of HIV proteins may be also the 66-97 SEQ ID NO:5, 117-147 SEQ ID NO:6 or 182-205 SEQ ID NO:7 fragments of the protein encoded by the NEF gene or the 183-214 SEQ ID NO:8 or 253-284 SEQ ID NO: 9 fragments of the protein encoded by the GAG gene.

Such peptides may be also some parts of the proteins specific of melanoma cells, preferentially coupled with a N-ε-palmitoyllysine (palm) or N-N'dipalmitoyllysine rest (dipalm) such as the following ones:

Theradigm-MART-AV: (dipalm) KSSQYIKANSKFIGITEAAAILTVILGVL SEQ ID NO:10

Theradigm-MART-AV: (dipalm) KSSQYIKANSKFIGITEAAAAAGIGILTV SEQ ID NO:11

MART-1 KKGHGHSYTTAEEAAGIGILTVILGVLLIG (palm)Lys-NH$_2$ SEQ ID NO:12

GP100 DFGDSSGTLISRALVVTHTYLEPGPVTAQV (palm)Lys-NH$_2$ SEQ ID NO: 13

They can be associated with the promiscuous peptide, coupled with a lipidic part as hereindefined, of which sequence is the following one:

peptide HA PKYVKONTL KLATGMRNVPEKOTR-GLFGA SEQ ID NO:14.

The peptides can be originated from parasites, in articular the ones having an intracellular development stage.

These peptides can be derived from LSA-3 (Liver Stage Antigen-3), such as:

729NR1 DELFNELLNSVDVNGEVKENILEESQ(palm) Lys-NH$_2$ SEQ ID NO:15

729NR2 LEESQVNDDIFNSLVKSVQQEQQHNV(palm) Lys-NH$_2$ SEQ ID NO:16 or from SALSA ( Sporozoite and Liver Stage Antigen), such as:

SALSA-1 SAEKKDEKEASEQGEESHKKENSQESA (palm)Lys-NH$_2$ SEQ ID NO:17

SALSA-2 NGKDDVKEEKKTNEKKDDGKTDKVQ EKVLEKSPKEF(palm)Lys-NH$_2$ SEQ ID NO:18

Peptides can also been the following ones:

MSP3 b AKEASSYDYILGWEFGGGVPEHKKEEN (palm)Lys-NH$_2$ SEQ ID NO:19

MSP3 c PEHKKEENMLSHLYVSSKDKENENISKENE (palm)Lys-NH$_2$SEQ ID NO:20.

The present invention relates moreover to pharmaceutical compositions containing an efficient quantity of at least one of the compounds above described in association with one or few diluents or adjuvants compatible and pharmaceutically acceptable.

These compositions are in particular intended for treating the diseases related with the HIV virus by induction of cytotoxic T lymphocytes.

The subject of the present invention is furthermore vaccines against viruses or parasites containing one of the above-described lipopeptides, and in particular vaccines against diseases linked to HIV viruses, said vaccines advantageously containing at least a fragment of a protein which is the product of the ENV gene, of the NEF gene or the GAG gene.

In particular, such a vaccine could contain the following fragments 307-331 SEQ ID NO:4 or 303-335 A1 fragments of the protein encoded by the ENV gene, 66-97 SEQ ID NO:5, 117-147 SEQ ID NO:6 and 182-205 SEQ ID NO:7 fragments of the protein encoded by the NEF gene, and 183-214 SEQ ID NO:8 and 253-284 SEQ ID NO:9 fragments of the protein encoded by the GAG gene.

The subject of the present invention is furthermore the use of the above-described lipopeptides for immunizing the human or animal body against pathogenic agents by inducing cytotoxic T lymphocytes. Such pathogenic agents may be viruses which have a substantial cytotoxic activity, in particular the HIV1 and HIV2 viruses, the respiratory diseases viruses and the influenza viruses, and certain parasites.

Said lipopeptides may also be used against certain cancers in order to induce a CTL response specific for certain tumor cells and in particular for proteins found at the surface of these cells.

The lipopeptides which are the subject of the present invention may be obtained from protein and pseudolipid constituents by methods known to a person skilled in the art, in particular, either by coupling the amino acids comprising the peptide part to the pseudolipid immobilized on a resin, that is to say by solid phase synthesis, or by coupling the pseudolipid to a peptide immobilized in a solid phase method, or by fragments coupling, or by coupling in solution the activated palmitic acid to the partially protected peptide.

It should be noted that the lipopeptides according to the invention possess the notable advantage of being capable of being adapted for inducing cytotoxic T lymphocytes against any type of antigenic determinant of any pathogenic agent.

Additionally, the present invention also relates to the following synthetic intermediates:

2-tert-butyloxycarbonylaminohexadecanoic acid (D,L) of the following formula (VIII):

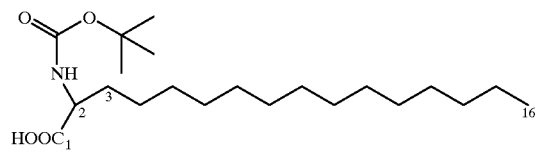

N-α-terbutyloxycarbonyl ε-palmitoyl-lysine (L) of the following formula (IX):

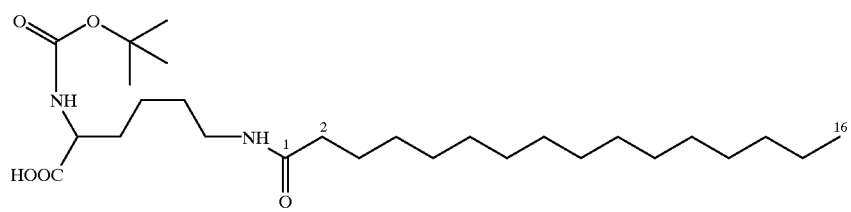

N-α-fluorenylmethyloxycarbonyl ε-palmitoyl-lysine (L) of the following formula (X):

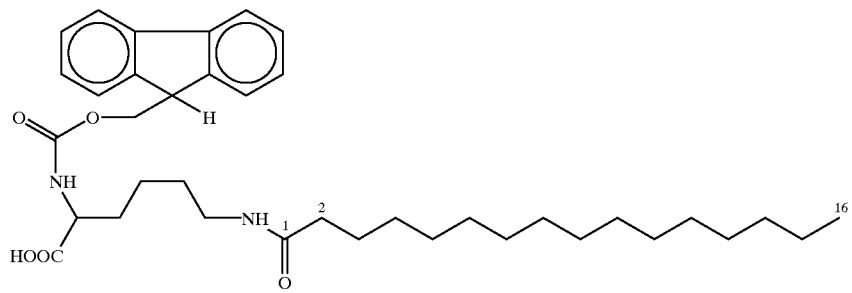

N-α-tert-butyloxycarbonyl ε-[(cholest-5-enyl-3-oxy)-acetyl]-lysine (L) of the following formula (XI):

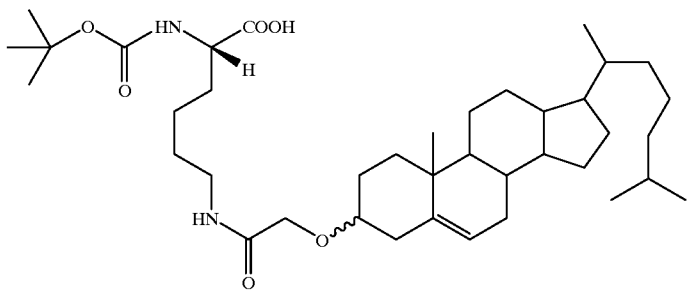

or N-α-fluorenylmethyloxycarbonyl ε-[(cholest-5-enyl-3-oxy)-acetyl]-lysine (L) of the following formula (XII):

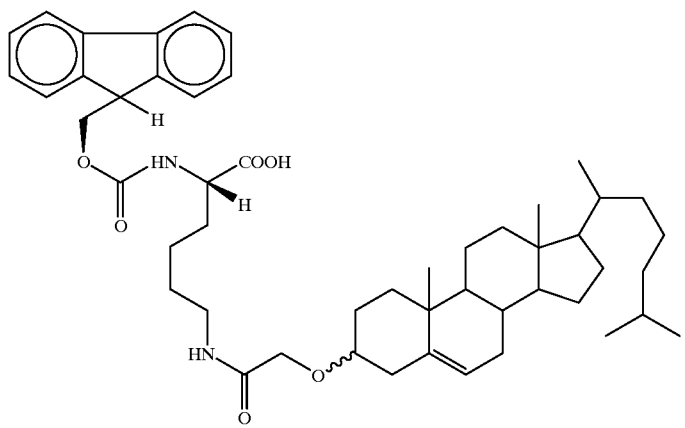

or one of their derivatives.

BRIEF DESCRIPTION OF THE DRAWINGS

The present invention is illustrated, without being limited in any manner, by the following examples of application in which.

The molecular weight assignment, determined by positive ion Plasma Desorption Mass Spectrometry, attests the presence of the lipidic component.

Figure 7B:
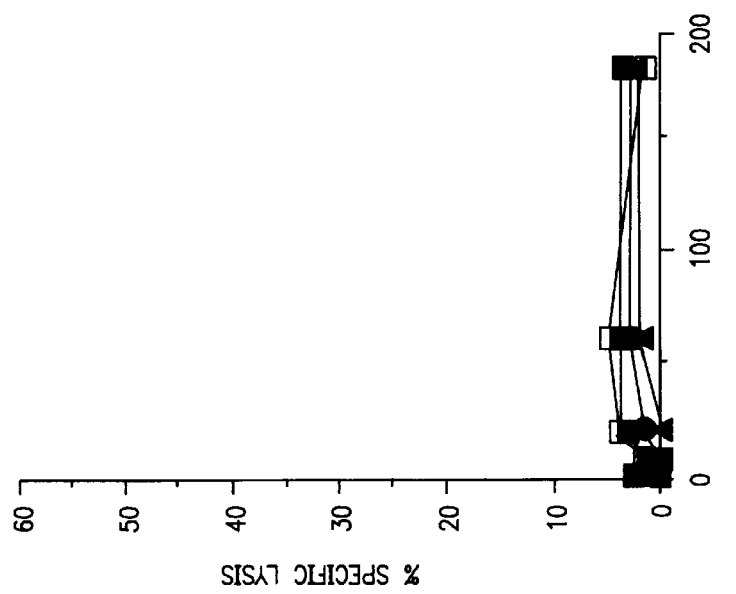
Figure 7A:
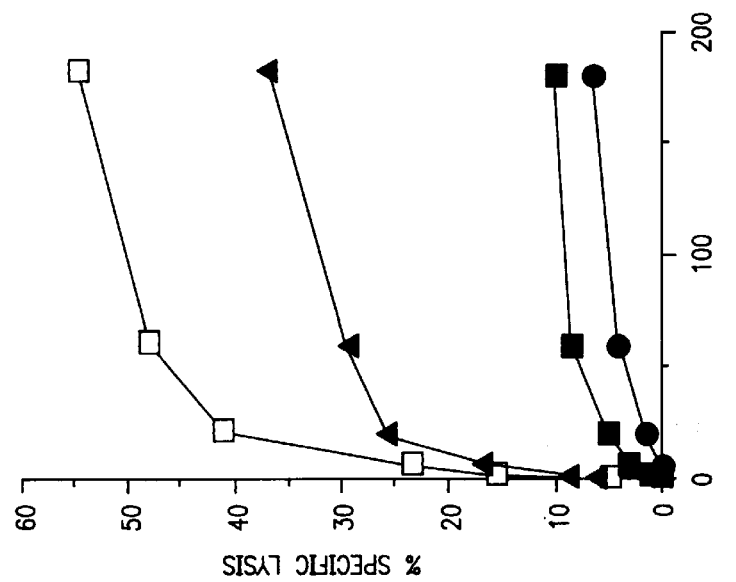

FIGS. 7a and 7b illustrates the Cytolytic activity of cell lines derived from BALB/c (H-2$^d$) mice: animals were primed s.c. with 50 nanomoles of V3SHda (FIG. 7a) in saline, or 50 nanomoles of V3S peptide alone (FIG. 7b). Three weeks later, they were boosted in identical conditions. Fifteen days after the last injection, spleens were removed for in vitro lymphocyte stimulation with peptide V3S. After a single in vitro stimulation, cell lines were tested for their capacity to lyse P815 target cells pretreated with the peptide V3S (open squares), P815 target cells infected with Vac-env (closed triangles) or with a virus expressing an irrelevant protein (Vac-gag: closed squares), or in culture medium alone (closed circles).

Figure 8B:
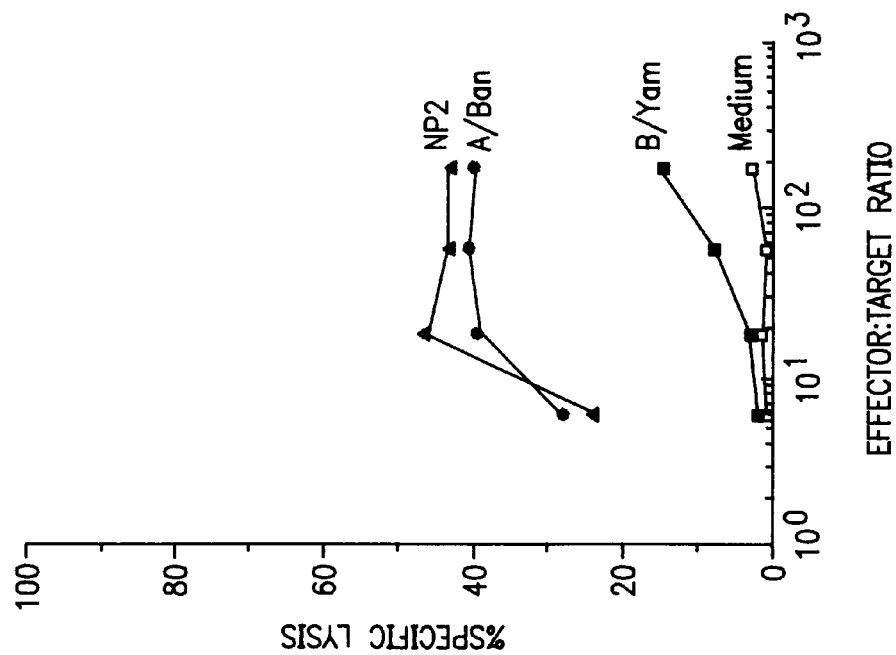
Figure 8A:
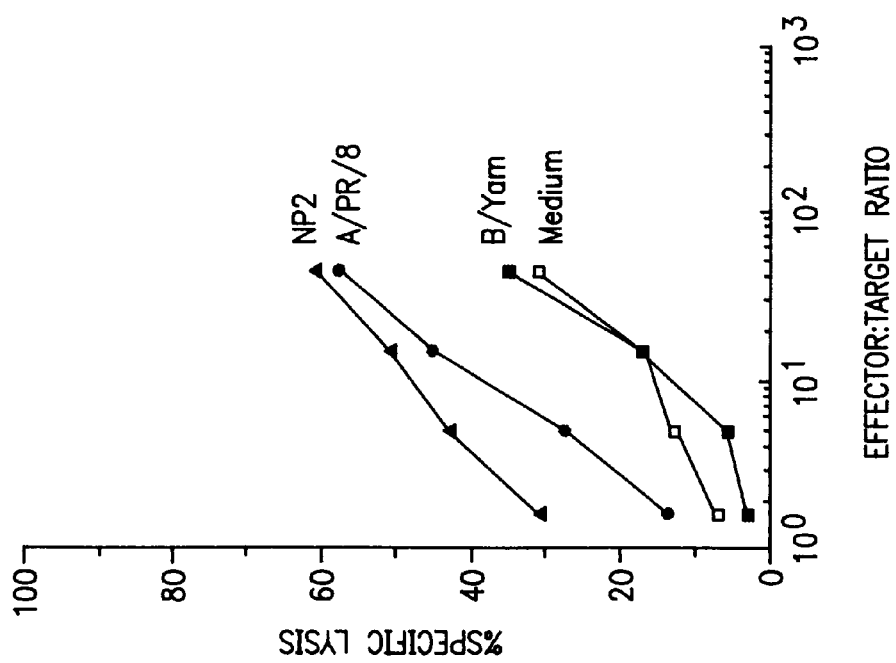

FIGS. 8a and 8b illustrate the in vivo priming of influenza virus-specific CTL with NP lipopeptide constructs. Spleen cells from BALB/c mice immunized i.p. (FIG. 8a) or s.c. (FIG. 8b) with lipo-NP2 were stimulated twice in vitro with NP2-pulsed BALB/c spleen cells. Cytotoxic activity was measured on P815 target cells pretreated as indicated in the figure.

FIGS. 9a to 9d illustrate the test of lipo-NP3 construct in B/6 and F1 mice. Spleen cells from B/6 (9A and 9C) or B/6 X CBA F1 (9b and 9d) mice immunized with Lipo-NP3 were stimulated twice in vitro with NP3-pulsed B/6 spleen cells. Cytotoxic activity was measured on EL4 target cells pretreated as indicated (9a and 9b). In another experiment, spleen cells were cultured in presence of peptide NP3, or the irrelevant NP2 peptide. After a 24 hours incubation, supernatants were collected and assayed for their content in IL-2, using [$^3$H]TdR incorporation of the IL-2 dependant CTL.L line (9c and 9d).

Figure 10C:
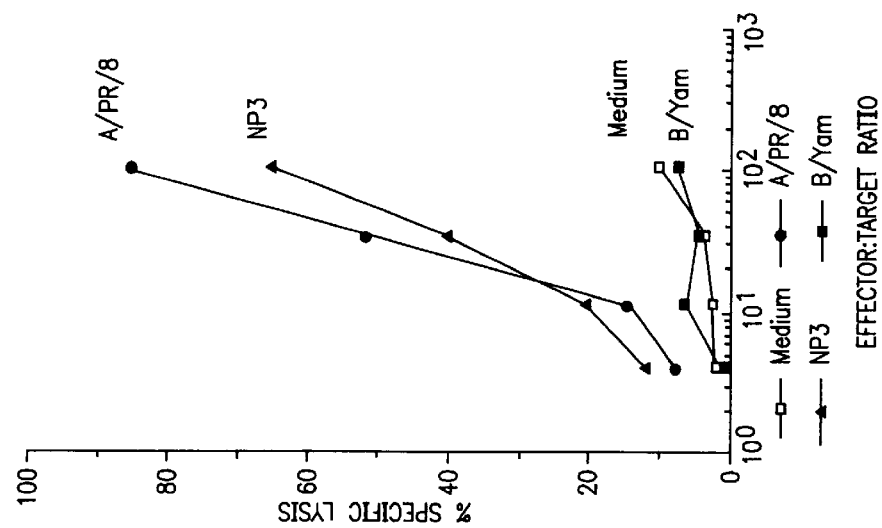
Figure 10B:
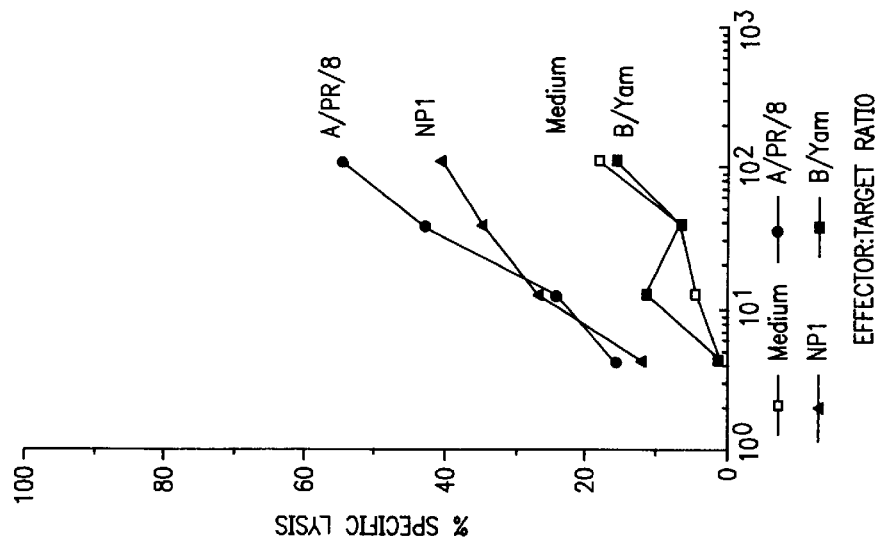
Figure 10A:
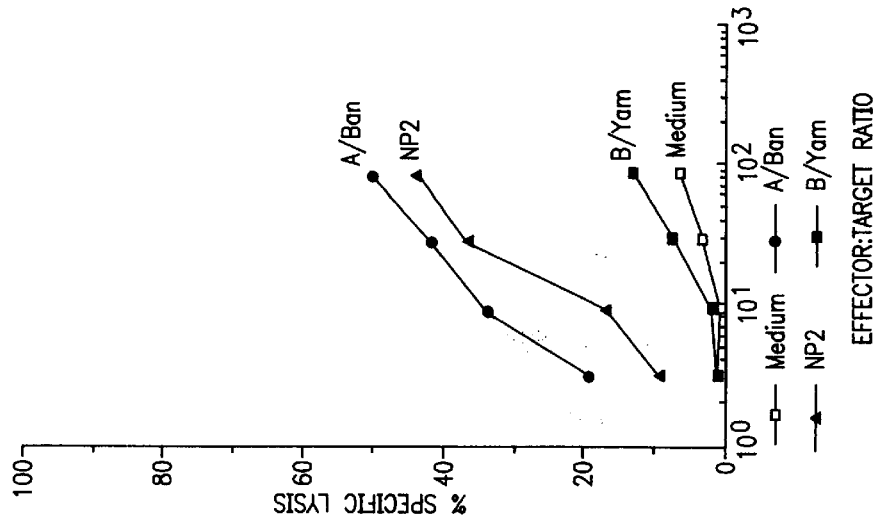

FIGS. 10a to 10c illustrate the in vivo induction of influenza virus nucleoprotein-specific CTL with the construct lipo-NP123. Spleen cells from BALB/c mice immunized s.c. with lipo-NP123 in saline were stimulated twice in vitro with NP2-pulsed BALB/c spleen cells (FIG. 10a). Identically immunized CBA or B/6 X CBA F1 mice were stimulated twice in vitro with either NP1-pulsed CBA or NP3-pulsed B/6 spleen cells (FIGS. 10b and 10c respectively). Responding cells were tested for their cytolytic activity on P815 (10a), RDM4 (10b), or EL4 (10c) target cells pretreated as indicated in the figure.

FIGS. 11a and 11b illustrate the Memory CTL response in mice primed with lipo-NP123. Spleen cells from BALB/c (FIG. 11a) and B/6 X CBA F1 (FIG. 11b) mice immunized s.c. six months before with lipo-NP123 were stimulated in vitro with NP2-pulsed BALB/c or with NP3-pulsed B/6 spleen cells respectively. Responding cells were tested for their cytolytic activity on P815 (FIG. 11a) or EL4 (FIG. 11b) target cells pretreated as indicated in the figure.

EXAMPLE 1

Synthesis of pseudolipid residues (or hydrophobic molecules)

1. Synthesis of 2-tert-butyloxycarbonyl-aminohexadecanoic acid.

1.1 Synthesis of 2-aminohexadecanoic acid.

Empirical formula: $C_{16}H_{33}NO_2$

Molecular mass: 271.44

Procedure:

0.0298 mole of 2-bromohexadecanoic acid (10 g) and 100 ml of a 28% solution of $NH_4OH$ are introduced into an autoclave previously cleaned with 50% nitric acid and 10% phosphoric acid. After stirring, the autoclave is heated at 60° C. for 15 hours. The nascent amino derivative precipitates in the reaction medium. After cooling, the autoclave is washed, the water dispersed and the ethanol removed. The reaction mixture is filtered on sintered glass with a porosity of 4 The difference in solubility of the various products in ethanol medium enables the removal of traces of 2-bromohexadecanoic acid by rinsing.

Amount of precipitate obtained: 4.37 g; yield of 54%.

Remark: The insolubility of the amino derivative was checked in numerous solvents (water, ethanol, acetic acid at low temperature, 70% formic acid, ethyl acetate, toluene, toluene/acetonitrile, ethyl acetate/acetonitrile). Among all the solubilization assays tested, only the action of a specific detergent (trimethylbenzylammonium hydroxide) or boiling acetic acid dissolved the amino derivative.

The dried precipitate is taken up in 150 ml of acetic acid which is refluxed until a yellowish clear solution is obtained. The colored pigments are absorbed on vegetable charcoal. After filtering on folded filter paper, the purified amino derivative is obtained by crystallization from the eluate. The white crystals obtained are recovered on sintered glass with a porosity of 4, washed with cold acetic acid before being dried in a desiccator over $P_2O_5$.

Yield: 46% (the product being in acetate form, a MW of 330.48 is used).

The purification yield is equal to 85%.

1.2. Synthesis of 2-tert-butyloxycarbonyl-aminohexadecanoic acid.

Empirical formula: $C_{21}H_{41}NO_4$

Molecular mass: 371.557.

Procedure:

Dissolution of 2-aminohexadecanoic acid.

1.1 equivalents of "Triton" (benzyltrimethyl-ammonium hydroxide) in solution at 40% in methanol (2.9 ml) as well as 100 ml of DMF are added to 5 mmol of amino acid in acetate form (1.655 g). The reaction mixture is left stirred at room temperature until complete dissolution. The DMF is then evaporated using a vane pump. The residue is dried in a desiccator over $P_2O_5$.

Protection of the amine functional group.

The dry residue is dissolved in a mixture consisting of 36 ml of water, 8 ml of IN $KHCO_3$ and 30 ml of tert-butyl alcohol. 2.5 equivalents of terbutyl-dicarbonate (MW= 218.25) are added to this solution. The pH is adjusted to between 8 and 9 using a 1N solution of $Na_2CO_3$ and maintained constant during the initial hours of the reaction. The kinetics of coupling are monitored by thin-layer chromatography on silica.

After evaporating the tert-butyl alcohol under vacuum, the product is taken up in 100 ml of water. The aqueous phase is acidified to pH 3 with a 1N solution of HCl. The Boc-amino acid is extracted with ethyl acetate (2×100 ml). The organic phase is washed with distilled water, dried over anhydrous $Na_2SO_4$, filtered and then concentrated using a rotating evaporator. 4 ml of hexane are added to the oily residue. Crystallization of the Boc-amino acid is enhanced by cooling in a cold chamber. The white crystals are recovered on sintered glass with a porosity of 4, washed with hexane and dried in a desiccator over $P_2O_5$. Yield: 16 to 18%.

1.3. Purification and characterization.

1.3.1. Purification.

Successive recrystallizations made it possible to increase the purity (increase in the melting point). The purification led to a reduction in yield of not more than 2% for aminohexadecanoic acid and of not more than 1% for the protected amino acid.

1.3.2. Characterization.

A. Melting point:

| Product | Melting point obtained |
| --- | --- |
| 2-Bromohexadecanoic acid | 56° C. |
| 2-Aminohexadecanoic acid | 144° C. |
| 2-tert-Butyloxycarbonyl-aminohexadecanoic acid | 85° C. |

B. Thin-layer chromatography on silica.

The solutions (10 to 20 μl of a solution at 1 mg/ml) are deposited on thin-layer silica (Merck silica gel 60 without fluorescence indicator).

2-Bromohexadecanoic acid is dissolved in ethanol, 2-aminohexadecanoic acid in boiling acetic acid, and tert-butyloxycarbonyl-2-aminohexadecanoate in dichloromethane.

Choice of the migration solvent.

The various systems chosen are:

System A: butanol/ethyl acetate/acetic acid/water in the volume/volume proportions: 1/1/1/1.

System B: ethyl acetate/pyridine/acetic acid/water in the v/v proportions: 5/5/1/3.

System C: chloroform/methanol/acetic acid in the v/v proportions: 10/1/0.1.

Developing.

After migration in the system of suitable solvents, the thin layers are dried for 15 minutes at 120° C. before being developed after spraying with a developing reagent.

The ninhydrin reagent which is specific for primary amino functional groups enables the detection of the unprotected aminohexadecanoic acid but also of the Boc-amino acid, the spraying of 20% acetic acid followed by drying at 120° C. enabling the displacement of the Boc group.

The spraying using a reagent comprising 20 g of $(NH_4)_2SO_4$, 3 ml of $H_2SO_4$ and 100 ml of $H_2O$ enable the simultaneous developing of the three products. In this technique, the drying, after spraying, in the thin-layer chromatography is carried out using an epi-radiator (porcelain resistance with infrared radiation).

Result:

| Product | Solvents | Rf |
|---|---|---|
| 2-Bromohexadecanoic acid | System A | 0.5 |
|  | System B | 1 |
|  | System C | 1 |
| 2-Aminohexadecanoic acid | System A | 0.82 |
|  | System B | 0.94 |
|  | System C | 0 |
| 2-tert-Butyloxycarbonyl-amino-hexadecanoic acid | System A | 1 |
|  | System B | 1 |
|  | System C | 0.67 |

C. Mass spectrometry (PDMS BIO-ION 20).
2-tert-Butyloxycarbonyl-aminohexadecanoic acid spectrum.

| MM (g) | (M—H)$^-$ | Fragments: |
|---|---|---|
| Theoretical MM | 370.557 |  |
| Experimental MM | 370.8 | 270 |

The experimental molecular ion and the theoretical molecular ion have an identical mass. The molecular ion is fragmented; the Boc group (peak at 270) is released. The 296.6 peak represents the ion with a mass of 270 containing the CN group (nitrocellulose).

2. Synthesis of 3β-(2'-carboxymethoxy)-cholest-5-ene.
2.1. Synthesis of cholesteryl tosylate.
Empirical formula: $C_{34}H_{53}SO_3$,
Molecular mass: 540.83,
Procedure:
After dissolving 25.86 mmol of cholesterol (10 g) in a minimum of pyridine (5 to 10 ml), an excess of tosyl chloride (10 g, 52.6 mmol) is added. After stirring for 12 hours, the pyridine is removed by evaporating to dryness. The residue is solubilized in 20 ml of acetone at high temperature (the temperature is maintained below 55° C. to avoid the formation of oil). The mixture is filtered. The cholesterol tosylate is obtained by crystallization from the eluate. The white crystals obtained are washed with cold acetone and dried in a desiccator over $P_2O_5$.
Yield: 82 to 85%.
2.2 Synthesis of 3β-(2'-hydroxyethoxy)-cholest-5-ene.
Empirical formula: $C_{29}H_{50}O_2$.
Molecular mass: 430.71.
Procedure:
30 ml of ethylene glycol (480 mmol) are added to 17.5 mmol of cholesteryl tosylate (10 g) dissolved in 120 ml of dioxane. The reaction mixture is refluxed for 4 hours at 120° C. After cooling, it is taken up in 150 ml of distilled water. The alcohol derivative formed is extracted with diethyl ether (3×200 ml). The ethereal phase is successively washed with 5% $NaHCO_3$ (2 200 ml) and distilled water (2×200 ml). After drying over anhydrous $Na_2SO_4$, the ethereal solution is concentrated until an oil is obtained. After adding 4 ml of hexane, the crystallization is started by rubbing and cooling in a cold chamber (4° C.). The white crystals are recovered on sintered glass with a porosity of 4 and washed with hexane before being dried in a desiccator over $P_2O_5$. Yield: 32 to 34%.

2.3. Synthesis of 3β-(2'-carboxymethoxy)-cholest-5-ene.
Empirical formula: $C_{29}H_{48}O_3$,
Molecular mass: 444.69.
Procedure:
The oxidizing solution is prepared beforehand: it comprises 2.67 g of chromic anhydride, 2.3 ml of concentrated $H_2SO4$, the volume being brought to 10 ml with distilled water. The oxidizing medium is added dropwise to 4.66 mmol (2 g) of 3β(2'-hydroxyethoxy)-cholest-5-ene dissolved in 50 ml of acetone. The progress of the reaction is monitored by thin-layer chromatography. Once the reaction is completed, the reaction medium is taken up in 250 ml of distilled water. The acid derivative is extracted with ethyl acetate (3×200 ml). The organic phase is washed with distilled water (2×200 ml), dried over anhydrous $Na_2SO_4$ and concentrated until an oil is obtained. 4 ml of petroleum ether are added. The crystallization of the acid derivative is enhanced by cooling in a cold chamber (4° C.). The white crystals are recovered on sintered glass with a porosity of 4, washed with petroleum ether and dried in a desiccator over $P_2O_5$. Yield: 29 to 31%.

2.4. Purification and characterization.
2.4.1. Purification.
Cholesteryl p-toluenesulfonate is purified by successive recrystallizations in acetone. β-(2'-Hydroxyethoxy)cholest-5-ene and the acid derivative have both been purified by thick-layer chromatography on silica.

A. Thick-layer chromatography on silica.
The depositions are carried out on a thick layer of silica (Merck silica gel 60 PF$_{254}$ with a fluorescence indicator), the spots being detected by ultraviolet radiation.
A solution containing 0.250 mg of product is deposited on the silica plate, the products have both been dissolved in dichloromethane.

| Product | Solvent | R$_f$ |
|---|---|---|
| 3β-(2'-Hydroxyethoxy) cholest-5-ene | Petroleum ether/ ethyl ether Volume/volume proportions: 1/1 | 0.48 |
| 3β-(2'-Carboxymethoxy)- cholest-5-ene | Petroleum ether/ ethyl ether/ methanol v/v proportions: 10/10/3 | 0.52 |

The two products were extracted from the silica with methanol. A loss equivalent to about 30% of the amount deposited is observed for each of the products.

2.4.2. Characterization.
A. Melting point.

| Product | Melting point (literature) | Melting point |
|---|---|---|
| Cholesteryl para-toluene-sulfonate | 131.5° C.–132.5° C. | 128° C. |
| 3β-(2'-Hydroxyethoxy) | 102° C.–104° C. | 99° C. |
| 3β-(2'-Carboxymethoxy)-cholest-5-ene | 160° C.–161° C. | 157° C. |

B. Thin-layer chromatography
The depositions (10 to 20 μl) of a 1 mg/ml solution are carried out on a thin layer of silica with a fluorescence indicator (Merck Kieselgel 60F$_{254}$).
The dissolution of the various products is carried out in dichloromethane.

After migration in the suitable solvent system, the thin layers are dried in air before being developed either by ultraviolet radiation or after spraying with $HClO_4$ (20%) and drying in an oven (120° C. for 20 minutes).

Result:

Various solvent systems.
System A: Ethyl ether/petroleum ether in the volume/volume proportions: 1/1.
System B: Ethyl ether/petroleum ether in the v/v proportions: 1/2.
System C: Petroleum ether/ethyl ether/methanol in the v/v proportions: 5/5/1.
System D: Petroleum ether/ethyl ether/methanol in the v/v proportions: 10/10/3.
System E: Petroleum ether/ethyl ether/methanol in the v/v proportions: 5/5/2.
System F: Ethyl ether.

| Product | Solvent system | $R_f$ |
|---|---|---|
| Cholesterol | System A | 0.54 |
|  | System B | 0.3 |
|  | System F | 0.95 |
| Cholesteryl para-toluenesulfonate | System A | 0.85 |
|  | System B | 0.62 |
|  | System F | 1 |
| 3β-(2'-Hydroxyethoxy)-cholest-5-ene | System A | 0.41 |
|  | System B | 0.24 |
|  | System F | 0.9 |
| 3β-(2'-Carboxymethoxy)-cholest-5-ene | System A | 0 |
|  | System B | 0 |
|  | System C | 0.1 |
|  | System D | 0.42 |
|  | System E | 0.78 |
|  | System F | Streaking effect: $R_f$ 0 0.5 |

C. Mass spectrometry (PDMS)
Analysis of the 3-β(2'-carboxymethoxy)cholest-5-ene.

| MM (g) | (M—H)⁻ |
|---|---|
| Theoretical MM | 443.69 |
| Experimental MM | 443.1 |

The experimental molecular ion and the theoretical molecular ion have an identical mass.

D. $^{13}C$ nuclear magnetic resonance

Analysis of the 3-β(2'-carboxymethoxy)cholest-5-ene spectrum was carried out by comparison with the $^{13}C$ NMR spectrum of cholesterol.

The dissolution of the cholesterol and the 3-β(2'-carboxymethoxy)cholest-5-ene was performed in deuterated chloroform.

Cholesterol spectrum.

| Peaks | d (ppm) obtained | attribution | theoretical d (ppm) |
|---|---|---|---|
| 1 | 140.7606 | C5 or C6 | alkene functional group: d (ppm) from 100 to 145 |
| 2 | 121.7064 | C5 or C6 |  |
| 3 | 78.5715 | $CDCl_3$ |  |
| 4 | 76.9981 | $CDCl_3$ |  |
| 5 | 75.4010 | $CDCl_3$ |  |

| Peaks | d (ppm) obtained | attribution | theoretical d (ppm) |
|---|---|---|---|
| 1' to 22' | 71 to 11 |  | alkane functional groups. |

3β-(2'-Carboxymethoxy)cholest-5-ene spectrum.

| Peaks | d (ppm) obtained | attribution | theoretical d (ppm) |
|---|---|---|---|
| 1 | 172.2923 | C2' | acid functional group: d (ppm) from 160 to 185 |
| 2 | 139.8394 | C5 or C6 | alkene functional group: d (ppm) from 100 to 145 |
| 3 | 122.5233 | C5 or C6 | alkene functional group |
| 4 | 80.5745 | C1' | ether functional group: d (ppm) from 45 to 80 |
| 5 | 79.2943 | C1' | + slight displacement |
| 6 | 78.5903 | $CDCl_3$ |  |
| 7 | 77.0089 | $CDCl_3$ |  |
| 8 | 75.4146 | $CDCl_3$ |  |
| 9 to 31 | 65 to 11 |  | alkane functional groups. |

E. Elemental analysis.

Elemental analysis of 3β-(2'-carboxymethoxy)cholest-5-ene gave the following results:

|  | Theoretical | Obtained |
|---|---|---|
| % carbon | 78.3 | 76.25 |
| % hydrogen | 10.9 | 10.9 |
| % oxygen | 10.8 | 12.5 |

EXAMPLE 2

Synthesis of the lipopetides

I. Method for coupling 2-aminohexadecanoic acid

The 312-327 SEQ ID NO:2 region of gp120 of the HIV-1 $LAV_{BRU}$ virus was chosen for sequences constructed in lipopeptide form in order to study the cytotoxic T response. 3 preparations were carried out using this sequence.

The synthesis was carried out in solid phase (MERRIFIELD R.B., 1963, J. Am. Chem. Soc. 85, 2149–2210).

All the lipopeptides were synthesized on a benzhydrylamine resin (charged at 0.72 millimole/gram). In all cases, the first amino acid grafted was 2-Boc-aminohexadecanoic acid (2 equivalents). This made it possible to obtain constructs where the C-terminal amino acid was 2-aminohexadecanoic acid in amide form in order to avoid the presence of a charge near the hydrophobic aliphatic chain. After acetylation with acetic anhydride in basic medium, in order to block the free reactive sites, the cleavage of the N-terminal Boc and then the coupling of the first amino acid of the sequence were carried out.

All these stages were carried out manually, which made it possible to carry out very precise controls of the coupling of the pseudolipid amino acid and the first amino acid on the latter.

The coupling activator is benzotriazolyl-N-oxytriadimethylaminophosphonium (BOP) in the presence of hydroxybenzotriazole (HOBt) and diisopropylethylamine (DIEA). By virtue of this very efficient coupling method, the yield of these two coupling reactions was always greater than 99.5% despite the substantial steric hindrance due to 2-Boc-aminohexadecanoic acid.

The rest of the synthesis was carried out in a conventional manner, automatically, up to the last amino acid. At this stage, the peptidyl-resin was divided into 3 batches, treated manually:

1 batch was preserved as such;

1 batch was grafted using 2-Boc-aminohexadecanoic acid. The manual coupling (using BOP) of the latter was followed by cleavage of the N-terminal Boc and acetylation of all the amine functional groups thus exposed. This made it possible to avoid the presence of a charge near the hydrophobic aliphatic chain of the pseudolipid amino acid, 1 batch was grafted using diBoc, N$\alpha$,$\epsilon$-lysine. manual grafting (using BOP) of the latter was followed by cleavage of the two Boc groups and the manual coupling of palmitic acid (using BOP). We thus obtained peptides possessing a dipalmitoyl-lysine in the N-terminal position.

These couplings, carried out manually, were the subject of a strict control which revealed yields that were always higher than 99.5%. These results confirm the advantage of using BOP as activating agent in peptide synthesis, especially for coupling pseudolipid amino acids or for coupling to the latter. The synthesized lipopeptides were then cleaved from their support. The lipopeptides derived from the 312-327 SEQ ID NO:2 sequence were cleaved by anhydrous hydrofluoric acid treatment. The cleavage yields are quite low, between 40 and 70%.

There are at least two explanations for these values: 1) the cleavage of a peptide grafted on a benzhydrylamine resin is never total under the usual conditions of cleavage; 2) the presence of 2-aminohexadecanoic acid, directly in contact with the resin, certainly amplified this phenomenon.

After washing twice (TFA-ether), the identity of the lipopeptides was assessed by amino acid analysis after total acid hydrolysis and, for some, by PDMS mass spectrometry. Their homogeneity was checked by thin layer chromatography on silica and analytical reverse phase HPLC.

II. Methods for coupling pimelautide and trimexautide

1) Method for coupling pimelautide (or trimexautide) to the N-terminal end of a peptide by means of a succinyl link.

This method applies to the fixing of unprotected pimelautide (or trimexautide) on a peptide constructed in a solid phase, still fixed to the resin, and to protected side chains.

Both trimexautide and pimelautide (Rhane Poulenc) have two free carboxylic functional groups and a free primary amine functional group. The creation of a predetermined amide bond between the peptide and the pimelautide (or trimexautide) can only be achieved by using the pimelautide (or trimexautide) as amino partner.

The succinylation of the peptide on the resin makes it possible to make it the carboxylic partner.

DEPROTECTION

The terbutyloxycarbonyl group, which temporarily protects the N-terminal end of the peptide on the resin, is cleaved by the action of a 40% trifluoroacetic acid solution in dichloromethane for 20 minutes with stirring.

The resin is washed with:

twice 20 ml of dichloromethane, twice 20 ml of 5% diisopropylethylamine in dichloromethane, twice 20 ml of dimethylformamide (for 3 minutes for each wash).

SUCCINYLATION

It is achieved by carrying out the coupling three times by bringing the resin of the succinylation solution into contact with:

a fivefold excess of succinic anhydride (5% solution in N-methylpyrrolidone)

diisopropylethylamine in a stoichiometric amount relative to the amines of the resin (for 20 minutes with stirring).

ACTIVATION

The activation of the carboxyl now present on the resin is carried out as follows:

the resin is subjected to the action of the activating solution (for 15 minutes at room temperature and with stirring):

BOP (benzotriazolyloxytrisdimethylaminophosphonium hexafluorophosphate): 3 excesses with respect to the carboxyls, HOBT (hydroxybenzotriazole): 3 excesses with respect to the carboxyls, diisopropylethylamine: 7 excesses with respect to the carboxyls in solution in N-methylpyrrolidone.

WASHING

The solution is washed with:

3 times 30 ml of dimethylformamide, 3 times 30 ml of dichloromethane.

COUPLING

The resin is subjected to the action of the coupling solution:

pimelautide (or trimexautide): 3 excesses with respect to the activated ester of hydroxybenzotriazole, diisopropylethylamine: 3 excesses with respect to the ester, 10% dimethyl sulfoxide 90% N-methylpyrrolidone: sufficient amount to dissolve pimelautide (or trimexautide). The saturated solution is at about 4% pimelautide or trimexautide after sonication and passage for 2 minutes at 50° C. 2) Synthesis in solid phase of V3GP120, 312-327 SEQ ID NO:2 succinyl.

a) N-Protection of the pimelautide for trimexautide) by the tert-butyloxycarbonyl croup.

500 micromoles of pimelautide (or trimexautide) are dissolved in 10 ml of a 0.1 molar solution of carbonate buffer at pH 9.5.

10 ml of a solution of diterbutyl pyrocarbonate at 100 mmol/l are added.

A pH of between 9 and 10 is maintained for 100 hours by adding disodium carbonate.

The reaction mixture is then diluted with 10 ml of water and 10 ml of diethyl ether and the washed aqueous phase is acidified to pH 2.5 with potassium bisulfate.

An extraction with 100 ml of dichloromethane followed by evaporation of the solvent using a rotating evaporator leads to the crystallization of Boc-pimelautide (or Boc-trimexautide).

The incorporation of Boc-pimelautide (or Boc-trimexautide) by peptide synthesis in a solid phase generates two position isomers.

19 b) CLEAVAGE AND PURIFICATION

The cleavage of the peptide at the end of the synthesis is performed using anhydrous hydrofluoric acid.

The peptide is then purified by gel filtration and type $C_4$ reverse-phase preparative HPLC.

Figure 1:
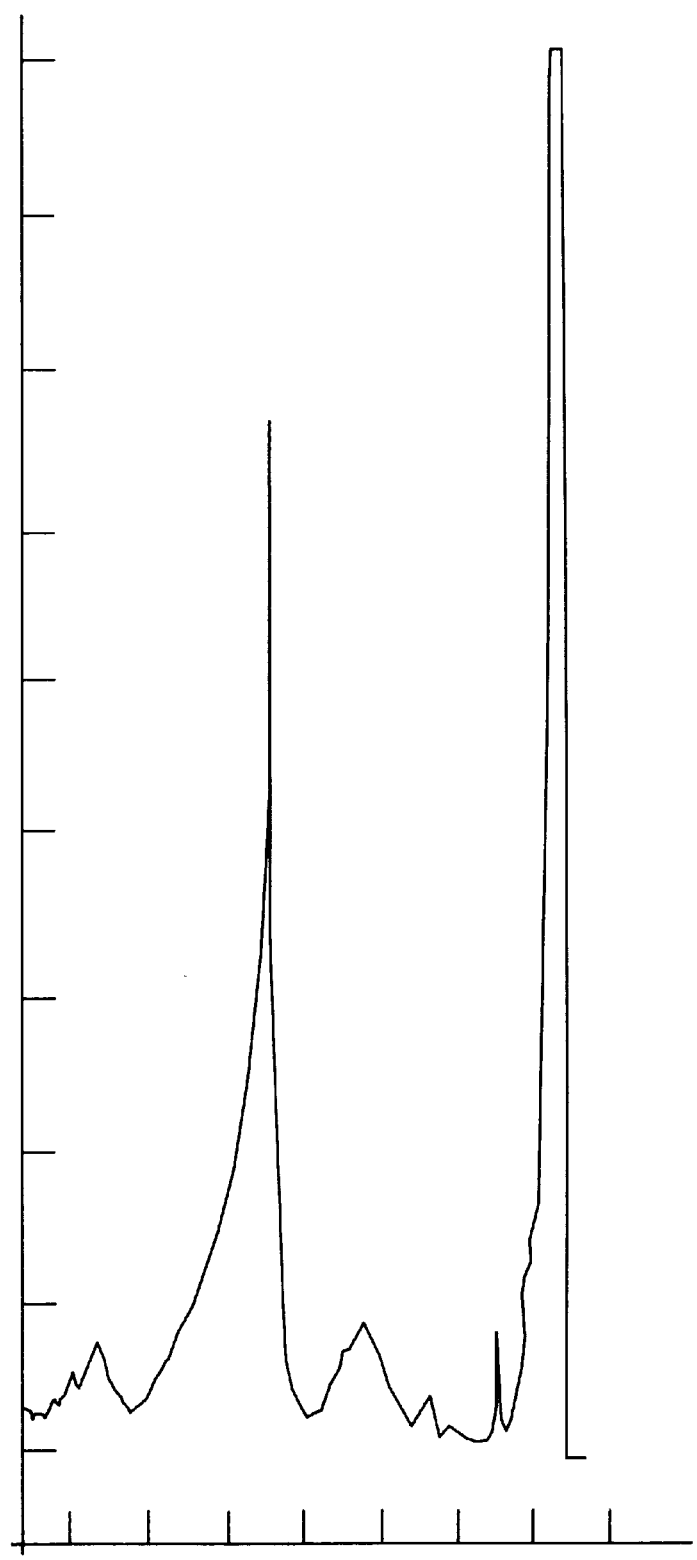
FIGS. 1 and 3a–b represent the reverse-phase HPLC spectra of the lipopeptide V3GP120, 312-327 succinyl during preparative and analytical electrophoreses respectively.

FIG. 1 represents the preparative HPLC spectrum at 235 nm obtained for 20 mg of lipopeptide dissolved in HCOOH.

The lipopeptide obtained is then analyzed by total acid hydrolysis, by analytical $C_4$ HPLC chromatography and mass spectrography.

Figure 2:
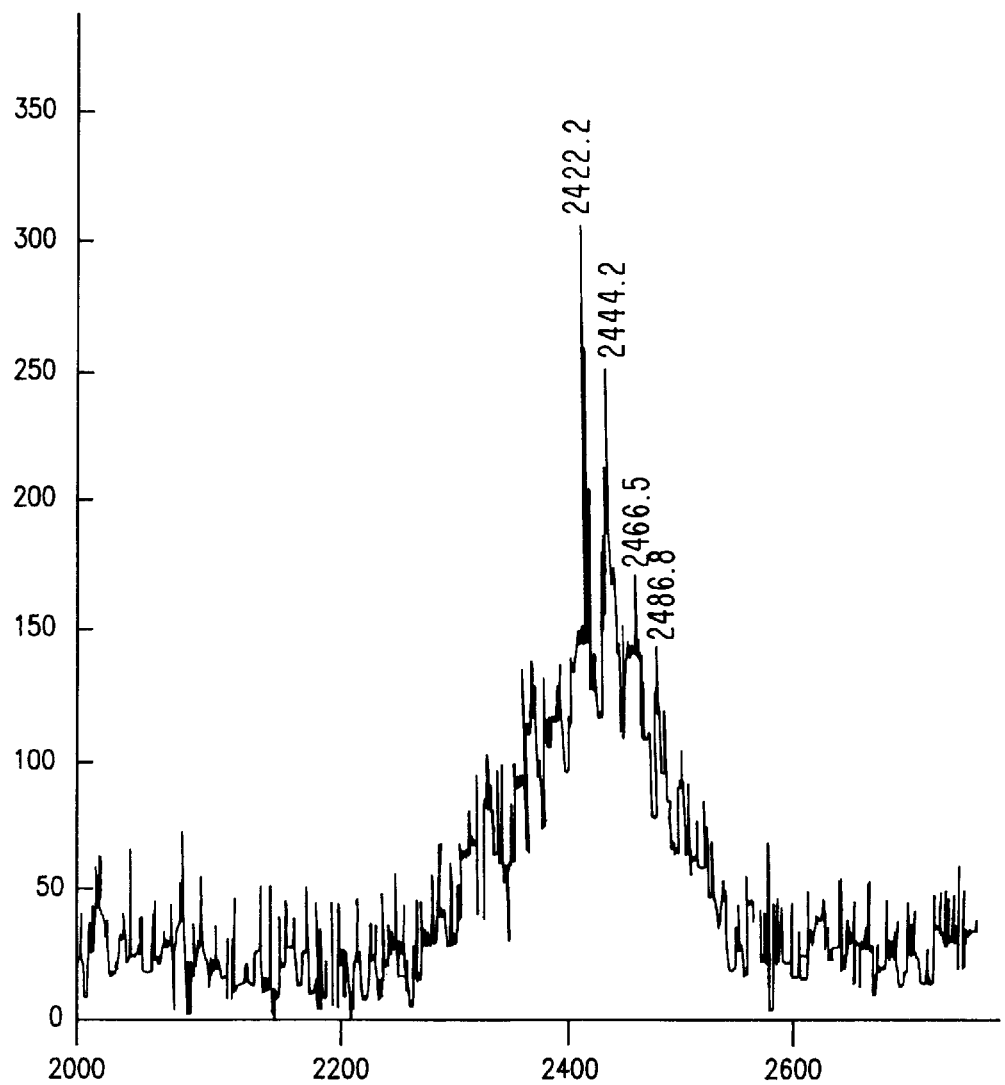
FIG. 2 represents, for its part, its mass spectrum.

FIG. 2 represents the mass spectrum. A distinct peak is observed at 2422.2 which corresponds to the mass of the lipopeptide.

Figure 3A:
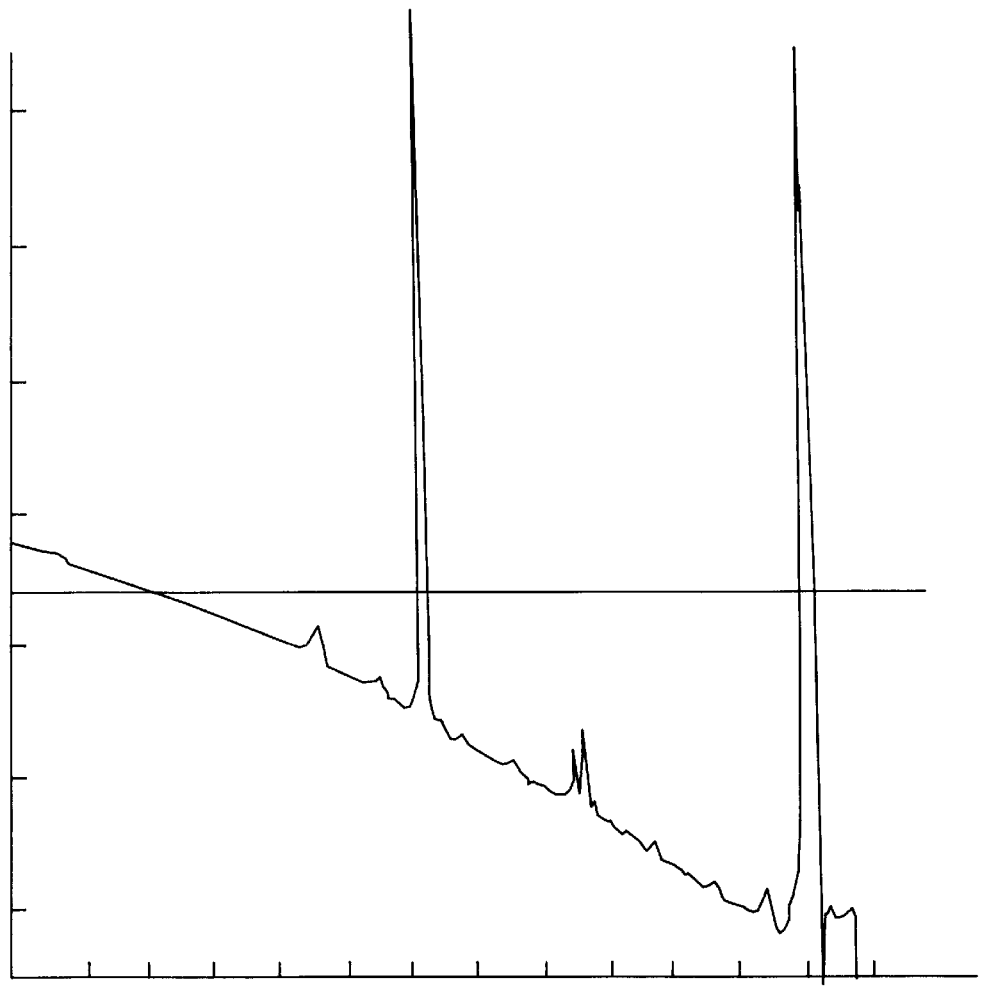
Figure 3B:
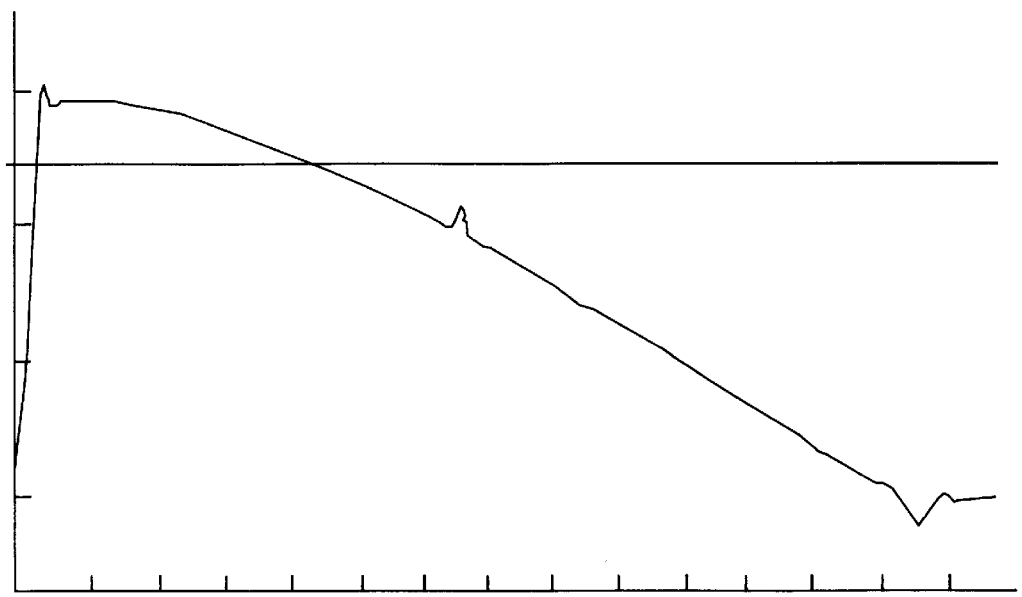

FIGS. 3a and 3b represent the analytical $C_4$ HPLC chromatography of the lipopeptide and of the control without lipopeptide respectively.

The chromatographic conditions are as follows:

solvent (A): 0.5 0/00 trifluoroacetate, gradient: solvent B: 0.75 0/00 acetonitrile 0.5% trifluoroacetate, gradient from 10% to 80% in 120 min, measurement at a wavelength of 215 nm.

During the total acid hydrolysis, the diaminopimelic acid (Dap) present in pimelautide and trimexautide constitutes a good coupling marker.

Results of the total acid hydrolysis

| Amino acids | nanomoles | measured | theoretical | measured/ theoretical |
|---|---|---|---|---|
| Thr | 3.2500 | 0.97 | 1 | 0.97/1 |
| Glu | 7.1000 | 2.11 | 2 | 1.06/1 |
| Pro | 3.1800 | 0.95 | 1 | 0.95/1 |
| Gly | 10.3500 | 3.08 | 3 | 1.03/1 |
| Arg | 6.6900 | 1.99 | 2 | 1.00/1 |
| Val | 3.3900 | 1.01 | 1 | 1.01/1 |
| Ile | 9.5800 | 2.85 | 3 | 0.95/1 |
| Phe | 3.3500 | 1.00 | 1 | 1.00/1 |
| Lys | 3.5200 | 1.05 | 1 | 1.05/1 |
| Arg | 9.9200 | 2.95 | 3 | 0.98/1 |
| Dap | 3.500 | 1.05 | 1 | 1.05/1 |

20

EXAMPLE 3

Immunization against the peptide NP 147-158 SEQ ID NO:1 by using lipopeptide comprising tetradecanoic rest.

The immunizations of mice are carried out as follows:

Immunizations

The mice were injected with the lipopeptide preparations intraperitoneally (i.p.) or subcutaneously (S.C.), with or without adjuvant.

At least two injections (at intervals of 8 to 30 days) are necessary in order to obtain CTLS.

Each injection contains $5 \times 10^{-8}$ mole of lipopeptide.

Detection of the CTLs 8 to 21 days after the last injection, the spleen of the immunized mice was removed, the splenocytes of these mice were cultured in vitro in an amount of $5 \times 10^6$ splenocytes/2 ml of conventional culture medium (DMEM+ 10% FeS+pyruvate+nonessential amino acids +β-2-mercaptoethanol) containing 5 µM of the peptide corresponding to that involved in the lipopeptide construction.

From the 5th day of the in vitro culture, the activity of the CTLs may be detected by the conventional test of $^{51}Cr$ release (Martinon et al., J. Immunol., 142;3489–3494, 1989).

The CTL activity is tested against some syngenic target cells in the presence of the peptide (NP 147-158 R⁻, P₃CSS. PepNP or L₁-Pep.NP) or against some syngenic target cells infected by the influenza A virus.

The results obtained are summarized in Table I. The first part of the table relates to the results already obtained with the whole influenza virus, the NP 147-158 R protein of the influenza virus and the P3CSS-PEPNP lipopeptide, which consists of the NP 147-158 peptide coupled to tripalmitoyl-S-glyceryl-cysteinylserylserine (DERES et al. previously mentioned).

The second part of the table relates, on the one hand, to the immunization trials carried out with liposomes containing the NP 147-158 peptide and with the lipopeptides L1, L2 and L3. These lipopeptides are molecules containing a peptide part (NP 147-158) and a lipid part, respectively. The lipopeptides L1, SEQ ID O:32 L2 SEQ ID NO:33 and L3 SEQ ID NO:34 are therefore of the following formulae

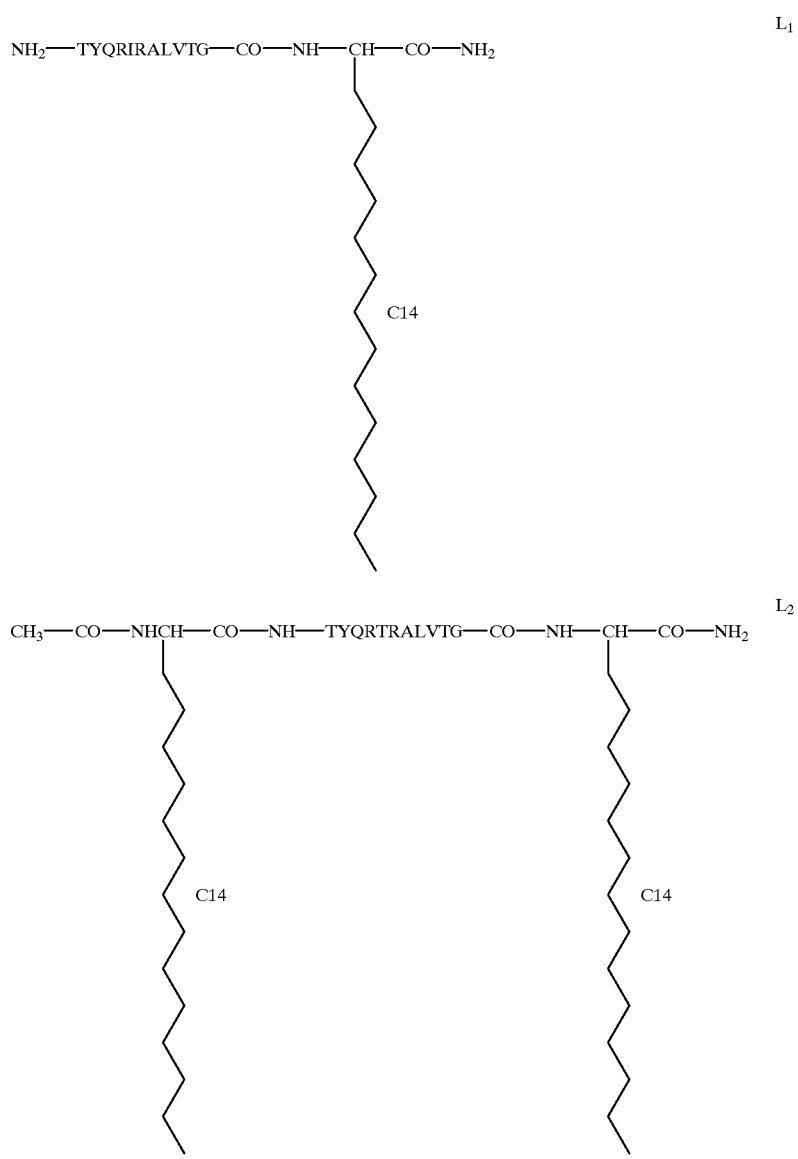

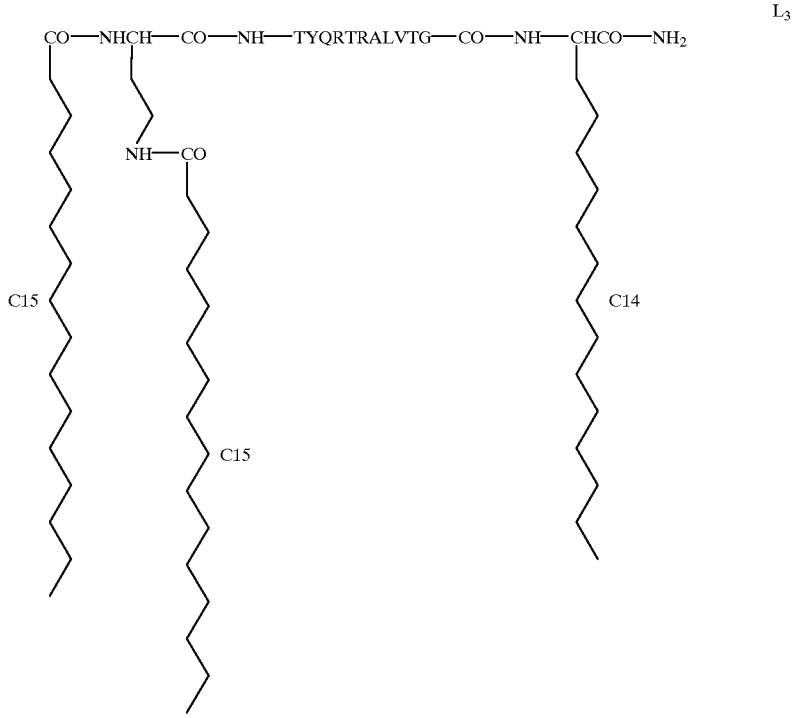

The cytolytic activities after 5 days, 12 days and more than 21 days show that a very high activity is obtained for the lipopeptide L1 compared to the other trials carried out.

EXAMPLE 4

Immunization by lipopeptides CB1 SEQ ID NO:35, CB2 SEQ ID NO:36 and CB3 A2 against the ENV 312-327 SEQ ID NO:2 peptide, comprising tetradecanoïc rest.

This peptide is a protein fragment encoded by the ENV gene of the HIV virus.

The experimental procedures are identical to those described in example 3.

Table II summarizes the results obtained.

In this table, CB1, CB2 and CB3 correspond to lipopeptides formed from the peptide derived from the ENV protein and a lipid. The formulae of CB1, CB2 and CB3 are as follows.

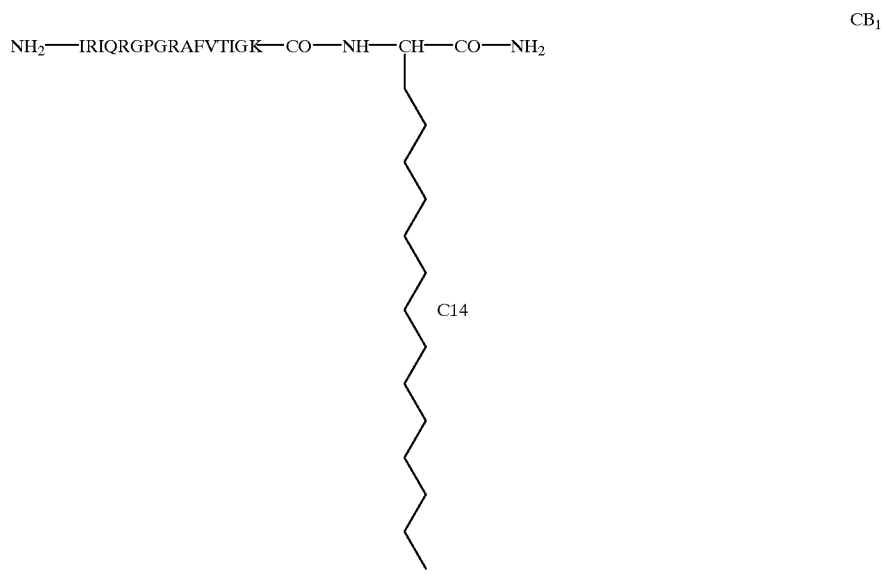

-continued

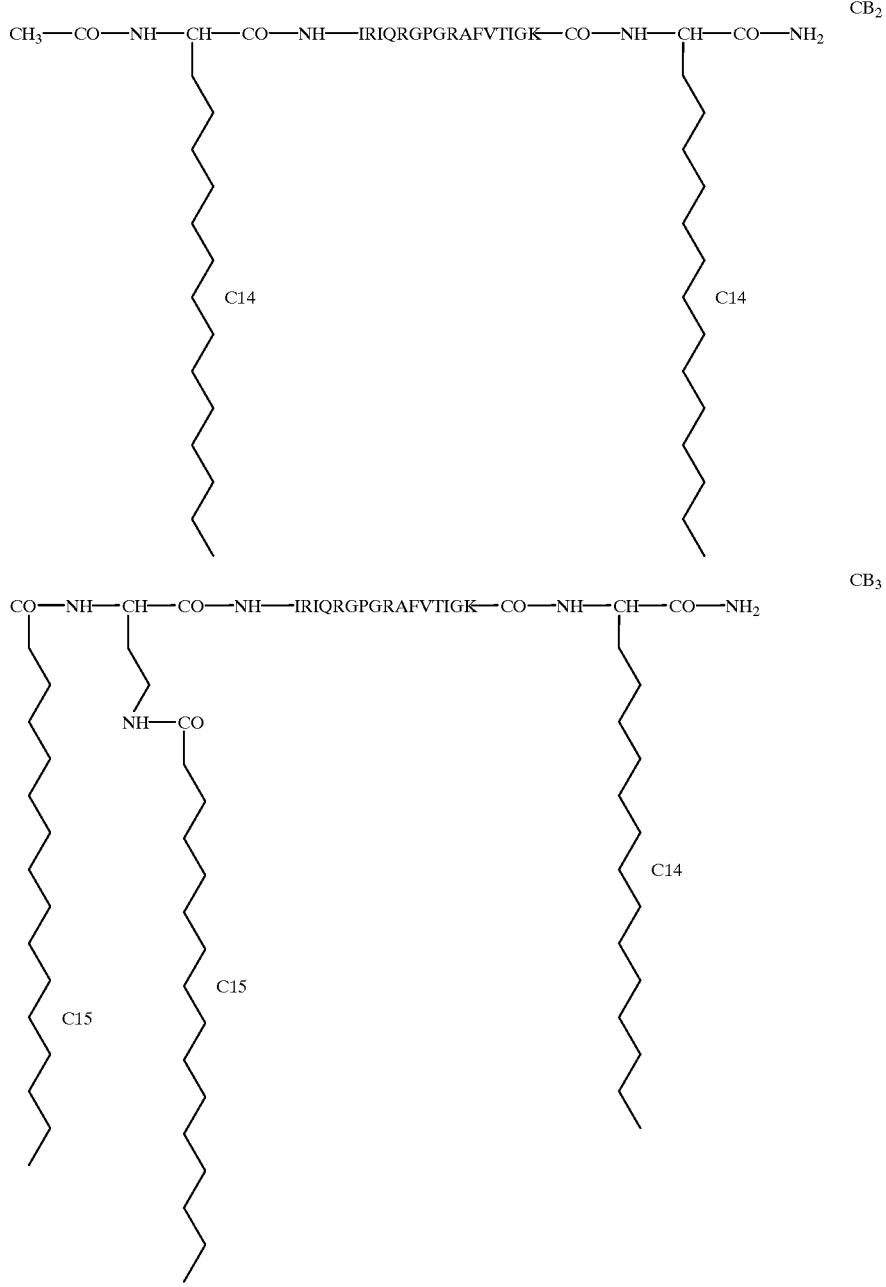

The results in table II show a substantial activity for one of the lipopeptides (CB1).

EXAMPLE 5

Immunization by lipopeptides comprising tetradecanoïc rest against the peptide ENV 302-335 SEQ ID NO:3 (amino acids 1-34)

This peptide is the 302 to 335 fragment of the ENV protein of the HIV virus.

The experimental procedures are identical to those described in Example 3.

The results are shown in Table III.

The formulae of the lipopeptides $CB_6$ SEQ ID NO:38, $CB_7$ SEQ ID NO:39 and $CB_8$ SEQ ID NO:40 are as follows:

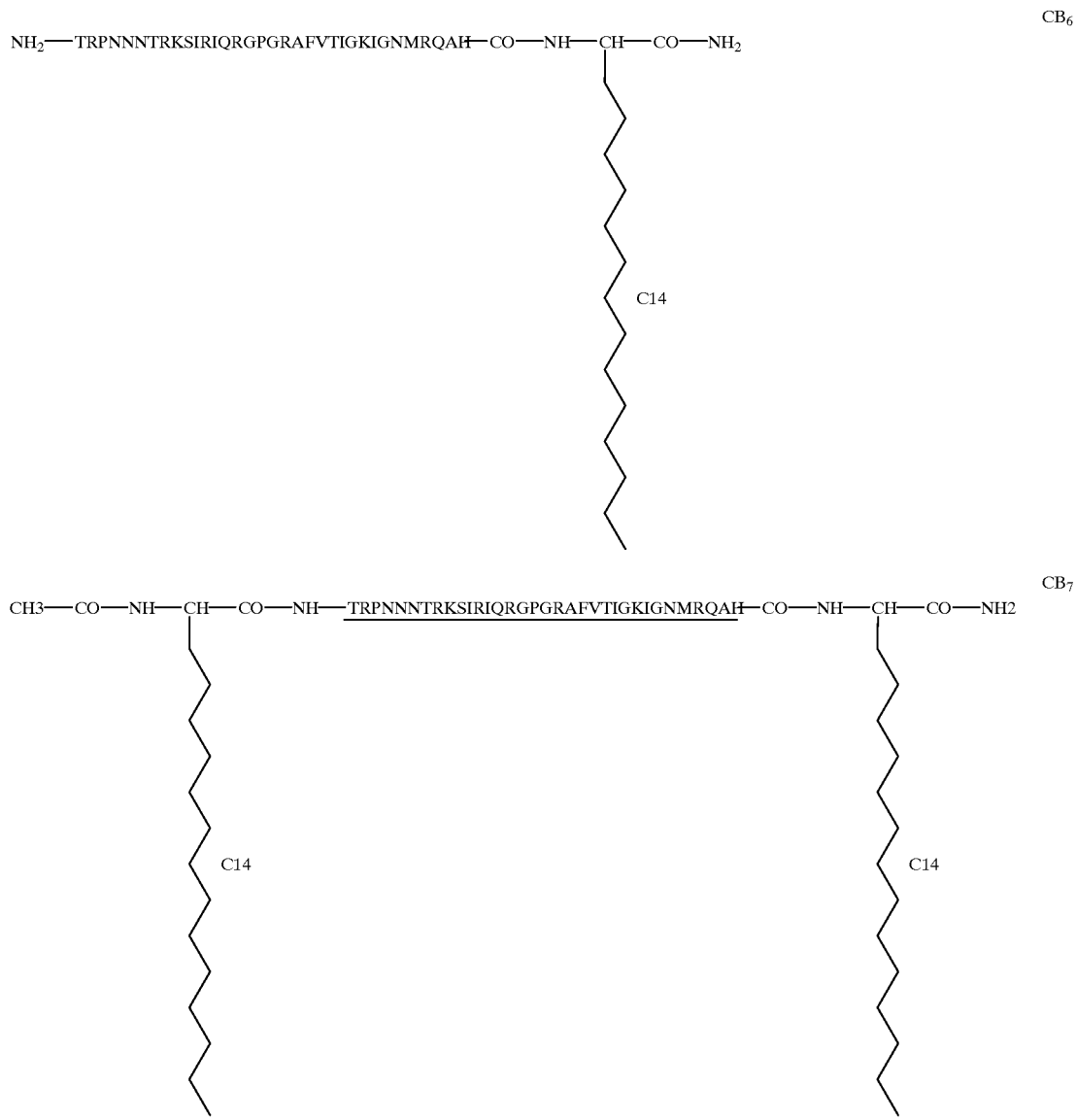

-continued

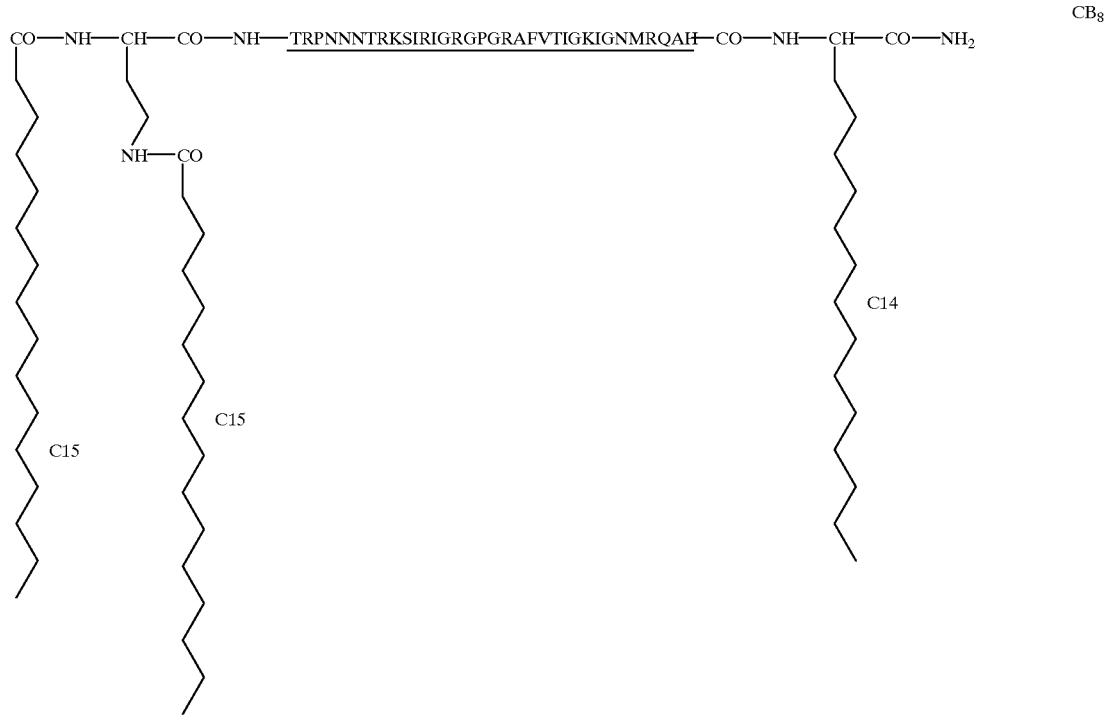

It can be observed in Table that the two lipopeptides, $CB_6$ and $CB_7$, show cytolytic activities substantially higher than the control.

EXAMPLE 6

Immunization against the peptide ENV 312-327 SEQ ID NO:2 by CB1 SEQ ID NO:35, CB4 A4, CB5 A5, CB17 SEQ ID NO:42, CB19 A6, CB21 SEQ ID NO:45 and CB25 SEQ ID NO:46.

The experimental procedures are substantially identical to those described in example 3.

The table IV summarizes the results obtained.

The formula of $CB_1$ is indicated in example 4.

The formulae of CB4, CB5, CB17, CB19, CB21 and CB25 are as follows:

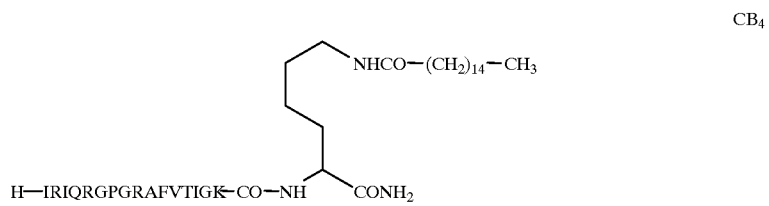

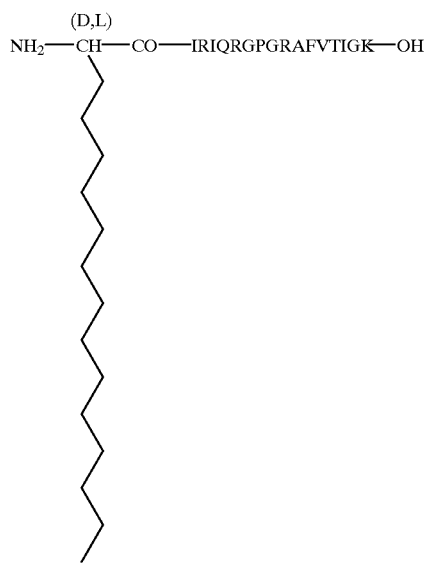
CB17
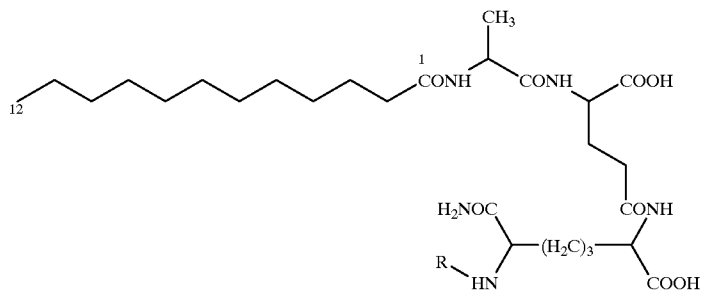
CB6 = R = CO—(CH$_2$)$_2$—CONH—
IRIQRGPGPGRAPVTIGK-OH  CB19=R=CO—CH$_2$—
NH—CO (CH$_2$)$_2$—CONH—HGQRGPGRAFVTUGKOH
IRIQRGPGRAFVTIGK—OH  R'=OH
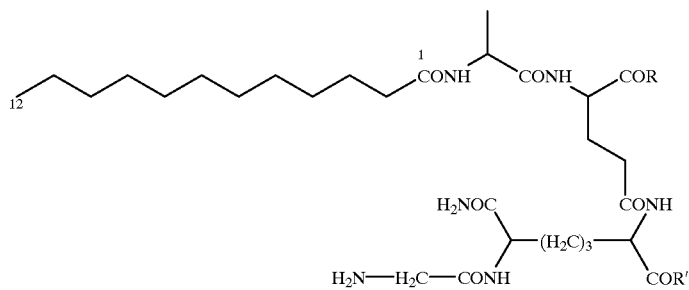
CB21  Mixture of A: R—OH  R'=NH—
IRIQRGIGRAPVTIGK—OH  B: R=NH—

EXAMPLE 7

Immunization by lipopeptides against NEF and GAG proteins

Materials and methods.

Sequences of peptides and lipopeptides

Peptides from NEF protein were as follows:

LP1 101-126 (S-V-R-P-K-V-P-L-R-A-M-T-Y-K-L-A-I-D-M-S-H-F-I-K-E-K SEQ ID NO:21)

LP2 125-147 (E-K-G-G-L-E-G-I-Y-Y-S-A-R-R-H-R-I-L-D-M-Y-L-E SEQ ID NO:22),

LP3 155-178 (D-W-Q-D-Y-T-S-G-P-G-I-R-Y-P-K-T-F-G-W-L-W-K-L-V SEQ ID NO:23),

LP4 201-225 (S-K-W-D-D-P-W-G-E-V-L-A-W-K-F-D-P-T-L-A-Y-T-Y-E-A SEQ ID NO:24) and LP5 221-247 (Y-T-Y-E-A-Y-A-R-Y-P-E-E-L-E-A-S-Q-A-C-Q-R-K-R-L-E-E-G SEQ ID NO:25).

In addition, two GAG SIV epitopic peptides.

LP6 165-195 (K-F-G-A-E-V-V-P-G-F-Q-A-L-S-E-G-C-T-P-Y-D-I-N-Q-M-L-N-C-V-G-D SEQ ID NO:26) and LP7 246-282 (Q-I-Q-W-M-Y-R-Q-Q-N-P-I-P-V-G-N-I-Y-R-R-W-I-Q-L-G-L-Q-K-C-V-R-M-Y-N-P-T-N SEQ ID NO:27) were synthesized.

Synthesis of p-methyl-BHA-N-BOC-HDA resin

N-tert-butyloxycarbonyl-amino hexadecanoic acid (Boc-Hda) was synthesized as described previously (Martinon et al.1992.J.Immunol.149: 3416). This molecule was manually coupled to the p-methyl-benzhydrylamine resin according to the BOP/HOBt procedure (Le-Nguyen et al. 1987.J. Chem..Soc.Perkin Trans. I:1915). All lipopeptides were thus obtained with a carboxamide C-terminal end.

Synthesis of lipopeptides

The lipopeptides were synthesized using the solid phase synthesis according to the "Boc-Benzyl strategy" (Merrifield, 1963. J.Amer.Chem.Soc.85:2149) in an automated Applied Biosystems 470A peptide synthesizer (Applied Biosystems. Foster City, USA), starting on 0.5 mmol of Boc-Hda-resin. Tert-butyloxycarbonyl (t-Boc) protected amino acids were purchased from the Peptide Institute (Osaka, Japan). The activation procedure was the dicyclohexylcarbodiimide/hydroxybenzotriazole method. Side chain functional groups were protected as follows-:serine (benzyl); threonine (benzyl); cysteine (S-para-methylbenzyl); aspartic (O-cyclohexyl); glutamic (O-cyclohexyl); tryptophane (formyl); histidine ($N^{-im}$ dinitrophenyl); tyrosine (2,6-dichloro-benzyl); arginine (tosyl); lysine (N-2-chlorobenzyloxycarbonyl) and methionine (sulfoxide). Coupling of each amino acid residues was followed by a capping step with acetic anhydride.

Cleavage and deprotection of lipopeptidyl-resins.

Before the hydrogen fluoride (HF) cleavage procedure (low and/or high HF) (Tam et al.1983. J.Am.Chem.Soc.105:6442), histidine ($N^{-im}$ dinitrophenyl) containing lipopeptides were stirred for one night at room temperature in a N,N-dimethylformamid/beta mercaptoethanol/N-ethyldiisopropyla-min (70/20/10:v/v/v) solution in order to remove the dinitrophenyl group. At the end of the HF cleavage, carried out with a Teflon-Kel F apparatus (Asti, Courbevoie, France), the lipopeptides were extracted from the resin with pure TFA and precipitated in a large volume of cold ether. After centrifugation, the precipitate was dissolved either in a 5% acetic acid solution or in a 5% ammonia solution in regard to their isoelectric pH.

The amino acid composition of each crude lipopeptide was determined by using an automated Beckman 6300 amino acid analyser (Beckman, Calif., USA) after total acid hydrolysis at 110° C. for 24 hours in 6M HCl.

Purification and characterization of lipopeptides by RP-HPLC

Lipopeptides were purified by RP-HPLC on a Vydac C4 7 μm 300A column (9×300 mm) using a acetonitrile-water-0.05% TFA solvent system. The lipopeptides were eluted from the column using a 60 minutes gradient from 24% to 60% acetonitrile. The flow rate was 2 ml/mn. Lipopeptides were characterized by amino acid analysis and molecular mass determination by Plasma Desorption Mass Spectrometry (PDMS) on a Bio ion 20 device (Applied Biosystems, Sweden) (Chowdhury and Chait.1989.Anal.Biochem. 180:387). The tubes containing pure lipopeptides were pooled and lyophilyzed.

Animals and protocol of immunizations

Twelve rhesus macaques (Macaca mulatta) were inoculated subcutaneously with a mixture of 7 lipopeptides (500 μg of each) in incomplete Freund adjuvant. Three immunizations were performed respectively at day 0.30 and 60. No side effect was observed except slight and transient erythema at the site of injection in macaque RS4.

Lymphocyte preparation

Peripheral blood mononuclear cells (PBMC) were isolated by density gradient centrifugation on lymphocyte separation medium (Flow Laboratories, Glasgow, United Kingdom) and were either used immediately or stored at −180° in liquid nitrogen.

Generation of the CTL lines

PBMC from rhesus macaques were cultured at $2.10^6$ cells/ml in 24-well microtiter plates in culture medium consisting of RPMi 1640 supplemented with penicillin (100 U/ml), streptomycin (100 μg/ml), L-glutamine (2 mM), nonessential amino acids (1%), sodium pyruvate (1 mM), HEPES (N-2-hydroxyethylpiperazine-N'-2-ethanesulfonic acid) buffer (10 mM), beta-mercaptoethanol ($2.10^{-5}$M), and 10% heat-inactivated human AB serum. Mixture of the 7 peptides was added in each well at a concentration of 5 μM. After 3 days, 10 IU/ml interleukin-2 (IL.2) (Boehringer, Mannheim) was added. At Days 7 and 14, cultures were stimulated by fresh autologous PBMC previously pulsed for 2 hours with the pool of the 7 peptides (5 μM), washed and irradiated (4,000 rads)(ratio effector: stimulator=1:3). In some experiments , effector cells have been stimulated by autologous SIV-infected cells prepared as follows. Briefly PBMC were cultured with ConA during 3 days and then infected with SIV ($10^2$ TCID50 for $10^6$ cells). After one week, these cells were washed and irradiated (10,000 rads) and served as stimulator (ratio effector:stimulator=1:1).

Phenotypic analysis of T-cell lines

The T-cell lines were phenotyped the day of the chromium release test (CRT) by incubating cells with fluorescein isothiocyanate-conjugated anti-CD4 (OKT4; Ortho Diagnostic Systems. Raritan, N.J.) and phycoerythrin-conjugated anti-CD8 (Leu-2a; Becton-Dickinson, Mountain, View, Calif.) monoclonal antibodies for 10 minutes at room temperature, washing once with phosphate-buffered saline. All cells were examined for percent positive-staining cells on an EPIC CS flow cytometer (Coulter).

Cell fractionation

PBMC were incubated at $10^7$ cells/ml with either OKT4 (2 μg) or Leu 2a (1 μg) for 30 minutes at 4° C. After incubation with OKT4 or Leu 2a, CD4+ or CD8+ cells were eliminated by magnetic separation with immunomagnetic beads (Dynabeads, Dynal, Oslo, Norway). The cells were then washed with culture medium.

In vitro transformation of B cell lines

B-lymphoblastoid cell lines (LCL) were generated by incubating serial dilutions of PBMC with supernatant of S 594, S 594, kindly provided by N.Letvin, is a cell line producing the immortalizing baboon herpes virus (Herpes virus papio). B-LCL were then cultured in culture medium supplemented with 10% foetal calf serum.

Recombinant vaccinia viruses

Sequences encoding the NEF and the GAG p55 proteins were inserted into vaccinia virus, which served to infect target cells. The wild-type vaccinia virus, strain Copenhagen, was used as a control. All these constructions were made by Transgene, Strasbourg, France.

Chromium release test (CRT)

To obtain target cells presenting SIVmac gene products, B-LCL were incubated at a concentration of $10^6$ cells/ml with recombinant vaccinia virus (20 pfu per cell) for 18 hours at 37° C. in a 5% $CO_2$ humidified atmosphere. To sensitize target cells with peptides, the peptides were incubated overnight at a concentration of 20 μM with $10^6$ B-LCL under the same conditions. B-cells were then washed and labelled with 100 μCl or $Na_2$ $^{51}CrO_4$ (Amersham, UK) for 1 hour, washed twice and used as target cells. $^{51}Cr$ release assay was performed in V-bottomed 96-well microtiter plated. The cytolytic activity of anti-SIV cell lines was measured by mixing $5 \times 10^3$ $^{51}Cr$ labelled target cells with effector cells at various E/T ratios in a final volume of 0.2 ml/well. Plates were incubated for 4 hours at 37° C. after which 0.1 ml of supernatant was harvested from each well and analysed by a gamma counter. Spontaneous release was determined after incubating target cells with medium alone and never exceeded 20% of the total $^{51}Cr$ incorporation. Results were expressed as specific chromium release: 100× (experimental cpm- spontaneous cpm)/(maximum cpm—spontaneous cpm).

RESULTS

1- CTL activities have been found in 7 macaques.

CTL activity has been induced in 7 macaques, directed against a NEF peptide in 5, and against a GAG peptide in the remaining 2 (table V). Six macaques recognized a single peptide, only one macaques, RS20 recognizing 2 different NEF peptides.

Among the NEF peptides, NEF 155-178 SEQ ID NO:23 appears highly immunogenic since it was epitopic for CTL in 3 macaques (RS6, RS17, RS20). NEF 201-225 SEQ ID NO:24 was recognized by 2 macaques (RS21, RS23). In contrast, NEF 125-147 SEQ ID NO:22 was recognized by only one macaque (RS20). Similarly, the two GAG peptides were recognized respectively by macaques RS4 (165-195) and RS7 (246-281). Finally, two of the NEF peptides, NEF 101-125 SEQ ID NO:21 and NEF 221-247 A7 (amino acids 1-25) have never been recognized.

Cytolytic activities were usually detected after 3 in vitro stimulations (day 21 of the culture) although some activities have been occasionally observed after only 1 or 2 in vitro stimulations.

Figure 4A:
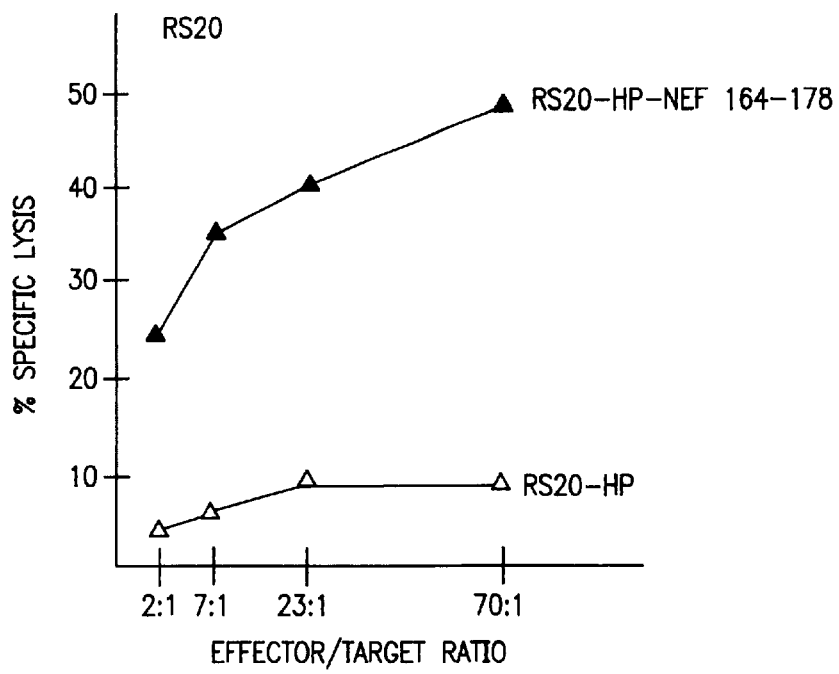
FIGS. 4a–c represents the specific cytolytic activity of an anti-peptide NEF.164-178 CTL from macaque RS20.
Figure 4B:
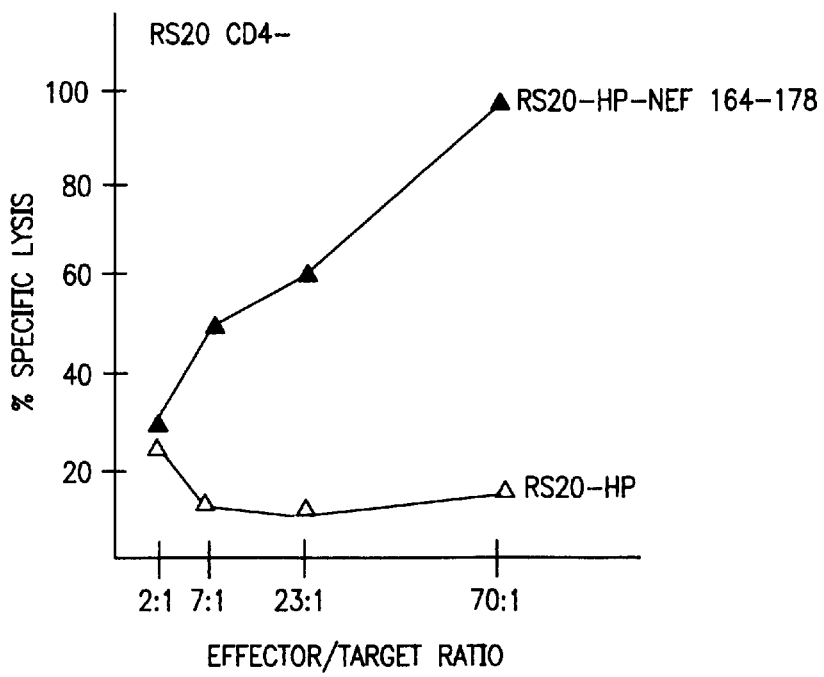
Figure 4C:
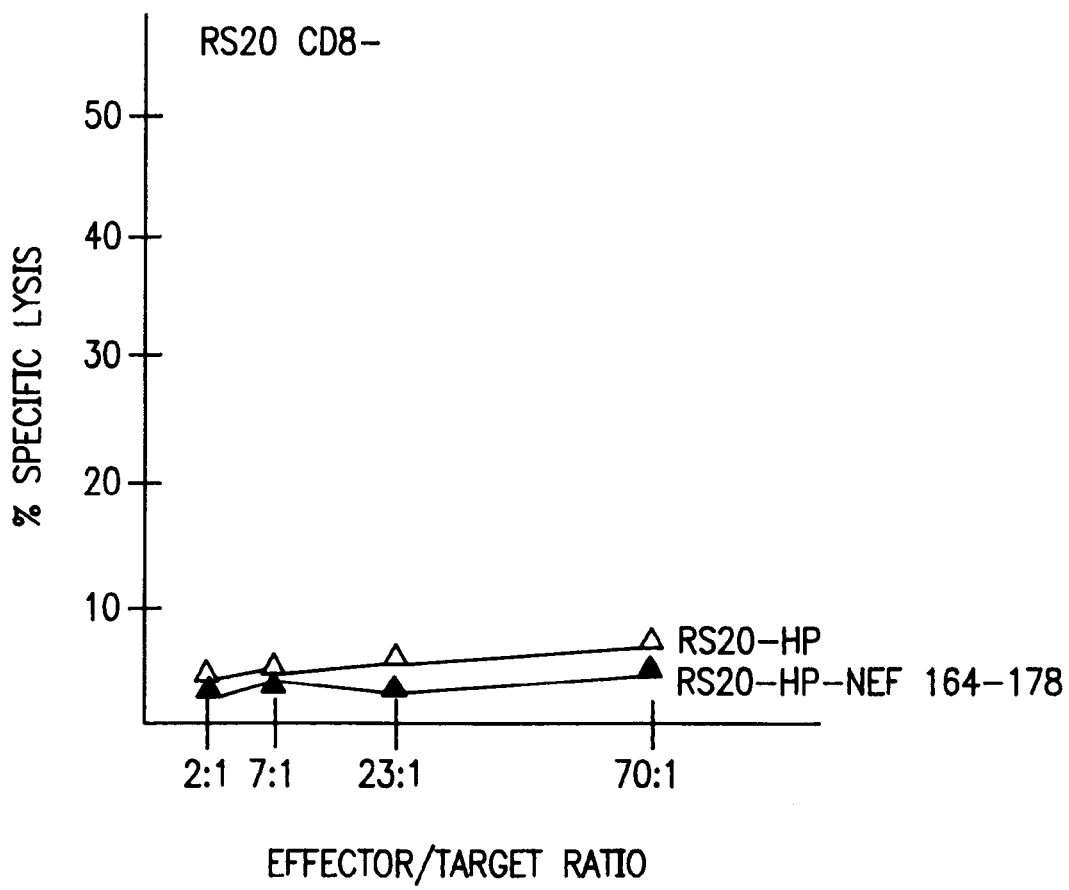

At day 21, the cell lines evidenced a predominantly CD8 phenotype ( on average 35% CD4+cells and 50% CD8+ cells) (table V) suggesting that the cytotoxic activities were mediated by CD8+lymphocytes. This was confirmed by depletion experiments, CTL activity disappearing after elimination of these cells, whereas CD4 depletion has no effect on the lysis, as illustrated in FIG. 4 for macaque RS20. This figure represents the specific cytolytic activity of antipeptide NEF 164-178 SEQ ID NO:28 CTL from macaque RS20. Effector cells were unfractionated PBMC (4a), or PBMC depleted of CD4+ cells by treatment with a monoclonal antibody anti-CD4 plus complement (4b), PBMC depleted of CD8+cells by treatment with an anti-CD8 monoclonal antibody (MoAb) bound to magnetic beads at the time of CRT (4 c). Target cells were autologous B-LCL alone or incubated with NEF peptide 164-178.

2-No CTL activity was found before immunization.

To assess the in vivo priming of macaques by lipopeptides and to discard a possible in vitro induction of CTL responses during the culture, the cells of 5 responding macaques have been tested (RS4, RS17, RS20, RS21, RS23) sampled before any in vivo immunization. They were stimulated in vitro with the pool of peptides. In most cases, no cellular growth was observed and massive cell death prevented from performing the CRT. In a few cases, cell lines were obtained. They were of the CD4+type and no cytotoxic activity was observed.

3-NEF and GAG specific CTL recognized naturally processed peptides from NEF or GAG proteins.

Figure 5B:
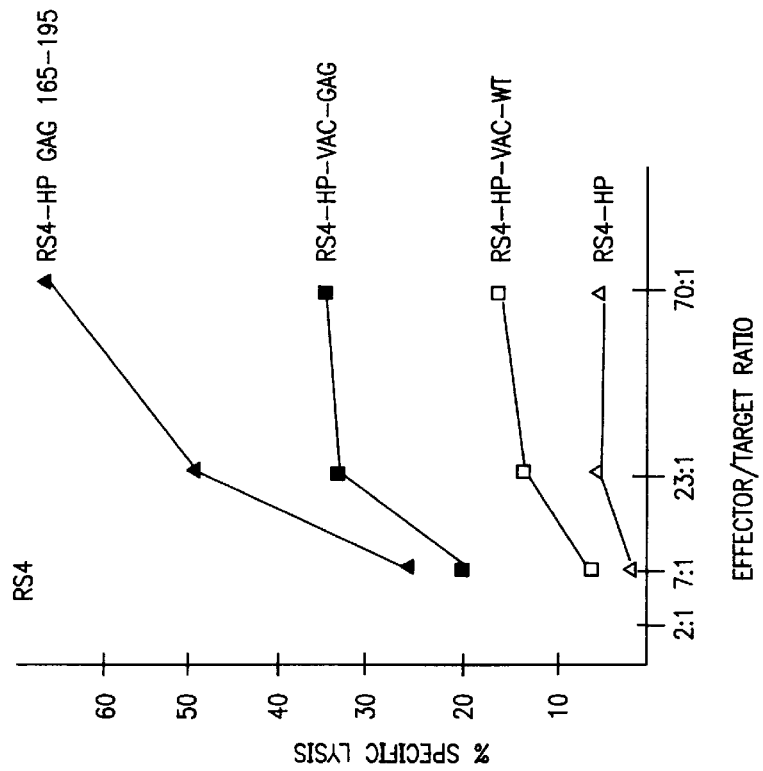
FIGS. 5a–b illustrates the cytolytic activity of RS4 effector cells stimulated by autologous PBMC sensitized with various peptides.
Figure 5A:
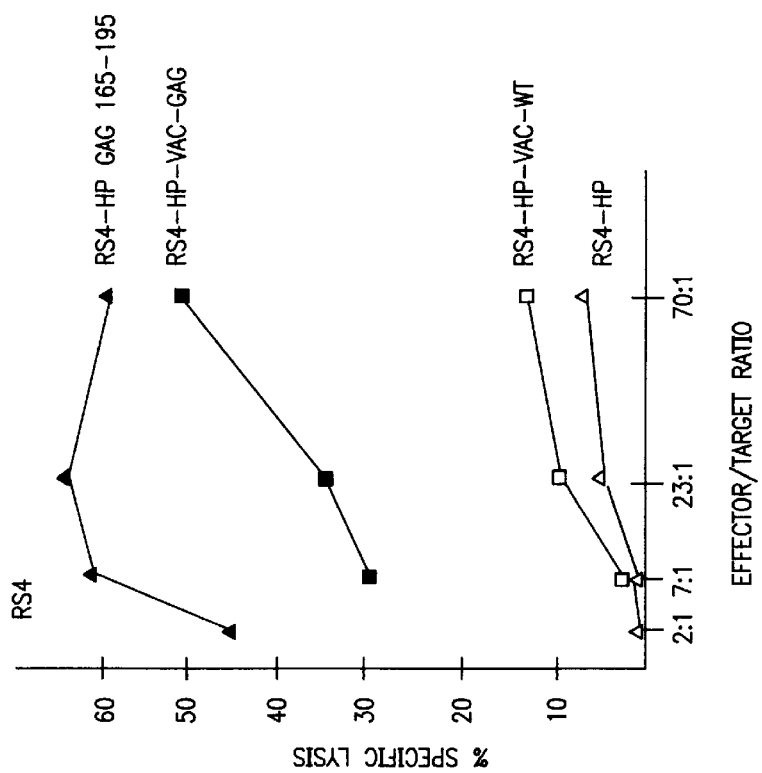

It was important to determine whether or not the CTL of responder macaques would be capable to recognize not only the immunizing synthetic peptides but also the naturally processed peptides in infected cells. To answer this question. Effector cells were stimulated by autologous P3MC sensitized with the mixture of peptides (5a) or by autologous SIV infected blasts (5b). Target cells were autologous B-LCL alone, incubated with peptide GAG 165-195, SEQ ID NO:26 infected with a wild type vaccinia virus or with GAG recombinant vaccinia virus (Vac-GAG).

a) It has demonstrated at first that CTL induced by lipopeptides could lyse Vac-NEF or Vac-GAG infected autologous target cells as illustrated for macaque RS4 in FIG. 5a. Similar cytolytic activities against Vac-NEF or Vac-GAG infected cells were regularly demonstrated in all the 7 responder macaques (Table VI).

b) PBMC from immunized animals have been stimulated by autologous SIV-infected cells. The CTL generated in these experiments were able to lyse peptide sensitized target cells as well as target cells infected with the corresponding recombinant vaccinia virus as shown in FIG. 5b for macaques RS4.

c) It must be also emphasized that in three responder macaques, shorter 15-mer peptides were defined as epitopes and were identical to epitopic peptides previously described in SIV-infected macaques (Table VII) (Bourgault et al. 1992.J.Virol.66:750, Yamamoto et al.1990.

J. Immunol.144:3385).

4. Kinetics of in vivo CTL responses.

Cytotoxic activities were systematically detected in all responder macaques after 3 immunizations. However, in 3 macaques (RS4, RS17 and RS20), CTL were already found after two immunizations.

Interestingly, after having been detected, these cytotoxic responses always persisted for at least 13 months after the last immunization in the two macaques (RS4 and RS20) which have the longest follow-up after immunization, confirming the presence of long lasting CTL memory cells in immunized animals.

EXAMPLE 8

Comparison of immunization against ENV 312-327 SEQ ID NO:2 and ENV 302-335 SEQ ID NO:3 (amino acids 1-34) by various lipopeptides.

In this example we have compared, in terms of ability to induce CTLs, several constructs obtained by modification with different simple lipidic amino-acids introduced at the C-terminal and/or the N-terminal part of two model peptides: a 16-mer peptide (V3S: sequence 312–327) containing known MHC-class I and class-II restricted epitopes, and a 34-mer peptide (V3L: sequence 302–335) derived from the third hypervariable domain of the gp160 envelop glycoprotein (the "V3 loop") of HIV-1 BRU. The different constructs where compared with reference to compounds modified by an a-amino hexadecanoic acid, and to a compound obtained by N-terminal introduction of the tripalmitoyl-S-glycerylcysteinylseryl-serine immunoadjuvant lipopeptide, analog to the compound described by Deres et al. (Nature 1989, 342:561).

1) Materials and methods

Abbreviations are as follows: DMF, N,N-dimethylformamide; HOBt, 1-hydroxybenzotriazol; NMP, N-methylpyrrolidinone; TFA, trifluoroacetic acid; Fmoc, fluorenemethyloxycarbonyl; tert-butyloxycarbonyl (t-Boc); BOP, (benzotriazol-1-yl-oxy) tris (dimethylamino) phosphonium hexafluorophosphate; PAM, phenylacetamidomethyl; MBHA, methylbenzhydrylamine; pmc, pentamethylchromanesulfonyl; Rink amide, 4-(2',4'-dimethoxyphenylaminomethyl)-phenoxymethyl resin; HF, hydrogen fluoride; DMEM, Dubelcco's modified Eagle medium; HEPES, N-2-hydroxyethylpiperazine-N'-2-ethanesulfonic acid.

Synthesis of the lipophilic amino acids

Synthesis of D, L α-amino hexadecanoïc acid (Hda): Into an autoclave were placed bromo-2-hexadecanoïc acid (Janssen) (10 g, 30 mmol) and 32% aqueous ammonia (100 ml). The reaction mixture was shaken at 130° C. for 18 hours. After cooling to room temperature, the precipitate was filtered and washed twice with water (2×100 ml), ethanol (100 ml), and recrystallized from boiling acetic acid. Yield 4.56 g (46%). Rf=0.82 in butanol/acetyl acetate/acetic acid/water 1/1/1/1 m.p.=236–238° C. (decomp.).

Synthesis of N-tert-butyloxycarbonyl- D, L α amino hexadecanoïc acid (Boc-Hda): Into a 250 ml round bottom flask were placed α amino hexadecanoïc acid (3 g, 9.1 mmole) and 100 ml of DMF. To this suspension was added 6 ml of a 40% solution of trimethylbenzylammonium hydroxyde in methanol (Janssen). The mixture was stirred for 12 hours, and DMF was evaporated under reduced pressure. The resulting white slurry was dispersed in a solution containing tertiobutanol (30 ml), water (36 ml), and 1M sodium hydrogenocarbonate (6 ml). Tertiobutyl pyrocarbonate (Janssen) (9.8 g, 45 mmole) was added, and the pH was maintained between 9 and 10 by additions of 1M sodium carbonate for 18 hours. Tertiobutanol was then evaporated in vacuum, and the resulting oily residue was taken up with 100 ml of water, and acidified to pH 4 with 1N aqueous HCl. The mixture was extracted twice with ethyl acetate (100 ml). The organic layers were washed with $10^{-4}$ aqueous HCl (100 ml), dried over sodium sulfate, and evaporated in vacuum. The resulting oily residue crystallized spontaneously at room temperature. Yield: 2.7 g (80%). m.p.=75° C. Rf=0.6 (chloroform/methanol/acetic acid, 9/1/0.1.

Synthesis of Nα-Fmoc-Nε-3β-(2'-carboxymethoxycholest-5-ene)-L-lysine (or N-ε-[(cholest-5-enyl-3-oxy) acetyl]lsine) (Fmoc-CholLys): 830 mg (1.53 mmole) of the N-hydroxysuccinimide ester of 3β-(2'-carboxymethoxycholest-5-ene) obtained as previously described (Ahmad et al. J. Chem., 24, 143–151) was added to a solution of 746 mg (1.53 mmoles) of Nα-Fmoc-lysine trifluoroacetate (obtained by trifluoroacetic acid deprotection of Nα-Fmoc-NεBoc-lysine), and 0.214 ml of triethylamine in 5 ml of methylene chloride. The reaction mixture was stirred overnight at room temperature. After addition of methanol (5 ml), and methylene chloride (20 ml), the reaction mixture was washed with $10^{-2}$ aqueous HCl. The organic layer was dried, and evaporated to give crystals. Yield: 0.88 g (73%). m.p.=89° C. Rf=0.5 (methylene chloride/methanol, 9/1), m/z: 795 [M+H]$^+$.

Peptide synthesis

All peptides except the PC3SS- and cholesteryl-modified analogs were synthesized using the conventional solid-phase "Boc-benzyl strategy" in an automated Applied Biosystem 430A peptide synthesizer (Applied Biosystems, Foster City, USA); t-Boc-protected amino acids were purchased from Propeptide (Vert-Le-Petit, France); Side chain protections were as follows: arginine (tosyl), threonine (benzyl ether), tyrosine (2,6-dichlorobenzyl ether); resins for solid phase synthesis were from Applied Biosystems, Foster City, USA. Peptides possessing a carboxylic C-terminal end were synthesized on N-t-Boc-Gly-PAM resin (Applied Biosystems, Foster City, USA), while peptides possessing a carboxamide C-terminal end were synthesized on a MBHA resin (Applied Biosystems, Foster City, USA).

N-terminal acetylation or succinylation (AcHda-V3S or SucHda-V3S) were performed on the peptidyl resin: after TFA-deprotection of the terminal Boc group and neutralisation; the acyl group was introduced using acetic or succinic anhydride, respectively.

An additional lysine residue was incorporated at the C- and/or N-terminal extremities for the synthesis of palmitoyl-modified analogs, with an orthogonal protecting group for the ε-NH$_2$ group. A Nα-Boc, Nε-Fmoc lysine (Novabiochem, EMA, Meudon, France) was used: immediately after introduction of the protected lysine, the Fmoc group was removed by 20% piperidine, and the palmitoyl-chain was introduced by activation of palmitic acid by the BOP reagent (Richelieu Biotechnologies, Ste-Hyacinthe, Quebec, Canada).

After hydrogen fluoride final deprotection and cleavage from the resin for 2 hours at 0° C., in a Teflon-Kel F apparatus (Asti, Courbevoie, France), the peptides were partially purified by two consecutive trifluoroacetic acid/ ether precipitations, and lyophilized.

Tripalmitoyl-S-glyceryl-cysteinyl-seryl-serin (P3CSS-) was a kind gift from Professor G. Jung (Tübingen, Germany). P3CSS- and cholesteryl-modified analogs were synthesized using the Fmoc-tBu Chemistry (Fields, and Noble, 1990 Int. J. Peptide Protein Res., 161–214). Fmoc-protected amino acids were purchased from Novabiochem (EMA, Meudon, France); side chain protections were as follows: arginine (pentamethylchromanesulfonyl), threonine (t-butyl ether), tyrosine (t-butyl ether). Peptides P3CSSV3S and CholLysV3s, possessing a carboxylic C-terminal end were synthesized on a Nα-Fmoc-Nε-Boc-Lys-Wang resin (Novabiochem, Meudon, France), while peptide V3S-CholLys, possessing a carboxamide C-terminal end, was synthesized on a Rink amide resin (Novabiochem, Meudon, France). P3CSS was introduced at the N-terminal end of the peptide by BOP activation.

Final deprotection and cleavage were performed in TFA:thioanisole:water:ethanedithiol (85:5:5:5), for 3 hours at room temperature. Peptides were partially purified by TFA-ether precipitations as above.

Reversed-phase preparative HPLC

Unmodified peptides and peptides modified by a single lipophilic amino acid were purified by reversed-phase preparative HPLC. Crude lipopeptides (50 mg per run) were solubilized in formic acid (0.5 ml) and water (2 ml), and applied onto a Vydac C4 7 $\mu$ 300 Å column (11×250 mm). Solvent system was: solvent A 0.05% TFA in water; solvent B: 0.05% TFA in acetonitrile/water (80/20), flow rate: 2.5 ml/min. The linear gradient used was from 10 to 100% solvent over 100 minutes. The column was washed during 10 minutes with isopropanol between each purification run.

Peptides characterizations.

Amino acid analysis: Hydrolysis of the peptides was performed with 6N HCl/phenol (10/1) at 110° C. for 24 hours in evacuated sealed tubes. Amino acid were quantified on a Beckman amino acid analyzer model 7300 with ninhydrine detection. Amino acids composition were as expected. Lipophilic amino acids were not determined with this method.

Mass spectrometry: The mass spectra were recorded on a Bio Ion 20 plasma desorption mass spectrometer, Bio Ion AB, Upsala, Sweden. Spectra were accumulated for $10^7$ fission events corresponding to approximatively 180 mn. Samples were analyzed using nitrocellulose targets, prepared by the spin drying technique using 50–100 $\mu$l of a 2 mg/ml nitrocellulose solution in acetone, applied onto a Mylar foil (1 cm i.d.). Samples were dissolved in water (1 mg/ml); 50 $\mu$l was applied on the nitrocellulose target by the spin drying technique. Mass determination was possible only for unmodified peptides, or peptides modified by a single lipophilic amino acid, after RP-HPLC purification. Results were as follows:V3S: [M+H]$^+$calc. 1769.1, found 1771; Ac-V3S-NH$_2$: calc. 1810.2, found 1810.1; P3CSS-V3S: calc. 2835.6 , found 2836.4; V3S-Hda: calc. 2023.5, found 2023.1; Hda-V3S: calc. 2024.5, found 2024. AcHda-V3S: calc. 2066.6, found 2066; V3S: calc. 1769.1, found 1771; SucHda-V3S: calc. 2124.6, found 2124.2; V3S-MPLys: calc. 2134.7, found 2135.2; V3S-CholLys: calc. 2343. found 2342; CholLys-V3S: calc. 2368.1, found 2368; V3L-Hda: calc. 4098.4 found 4100.7; V3L-MPLys: calc. 4212.1, found 4217.

Analytical high-pressure liquid chromatography: 10 $\mu$l of peptide solutions (1 mg/ml) were applied onto a Vydac C4 5 $\mu$ 300 Å column (250×4.6 mm) in a Shimadzu system. Solvent A was 0.05% TFA in water, solvent B was 0.042% TFA in acetonitrile-water (80/20).

Priming of mice and generation of CTL

BALB/c mice (H-2$^d$) were primed subcutaneously with 50 nanomoles of free peptide or lipopeptide in PBS. Three weeks later, mice were boosted under identical conditions. Fifteen days after the last injection, spleens were removed for in vitro lymphocyte stimulation. Splenocytes from naive or primed mice were cultured for 6 days in 24-well plates at 5×10$^6$ cells per well in 2 ml DMEM supplemented with 100 U/ml penicillin, 100 $\mu$g/ml streptomycin, 2 mM L-glutamine, nonessential amino acids, 1 mM sodium pyruvate, 10 mM HEPES, 2.5 mg/ml amphotericin B, 50 $\mu$M 2-mercaptoethanol and 10% heat-inactivated FCS (Flow Laboratories, Irvine, Scotland) (culture medium) containing 3–5 $\mu$M synthetic V3S peptide.

Viruses

The vaccinia virus recombinant for the env and gag genes of HIV-1-BRU (Vac-env) and (Vac-gag) (Transgène, Strasbourg, France) were kindly provided by the Agence Nationale de Recherches sur le SIDA (ANRS).

Cytotoxicity assays

P815 (H-$_2^d$, DBA/2) cells (1–2×10$^6$) in 200 $\mu$l culture medium were labelled with 100 $\mu$Ci Na$_2^5$CrO$_4$ (CEA, Gif sur Yvette, France) for 1 hour at 37° C. After two washings, 3,000 labelled target and serial dilutions of effector cells were incubated in 200 $\mu$l of culture medium in round-bottomed microtiter plates. Synthetic peptides were included in the appropriate assays at 3 $\mu$M. In the case of virus-infected targets, cells were incubated overnight at 37° C. with 10 PFU per cell of recombinant vaccinia virus. The cytotoxicity assay was terminated after 4 hours of incubation at 37° C., and 100 $\mu$l of supernatant were harvested and specific lysis was determined as: % specific lysis=100× (experimental—spontaneous release)/(half total $^{51}$Cr incorporated-spontaneous release). In all experiments, spontaneous release in the absence of effector cells was less than 20% of maximum release. 2) Results Peptide synthesis and characterization.

The $\alpha$-D,L-aminohexadecanoic acid (Hda) was obtained by nucleophilic substitution of $\alpha$-D,L-bromohexadecanoYc acid by ammonia. As this amino-acid was obtained in a racemic form, the corresponding peptides were obtained and tested as equimolecular mixture of diastereoisomers. The N$\alpha$-t-Boc, N$\epsilon$-palmitoyl-lysine (Boc-PalmLys), and the N$\alpha$-Fmoc, N$\epsilon$-3$\beta$-(2'-carboxymethoxy-cholest-5-ene)-lysine (Fmoc-CholLys) were obtained in non-racemizing conditions by derivatization of the N$\alpha$ protected L-lysine, and were thus enantiomerically pure.

All peptides were soluble in water (>2 mg/ml), except the heavily lipided forms of the short peptide (DPLys-V3S-Hda, Hda-V3S-Hda), which yielded turbid suspensions. These solutions or suspensions were not filtrated before in vivo priming of animals.

All soluble peptides, except Hda-V3L-Hda and DPLys-V3L-Hda, were purified by RP-HPLC. Purification yields after RP-HPLC of soluble peptides were between 38 and 55% for the non-lipidic form V3S and Ac-V3S-NH$_2$, and between 32 and 38% for the V3S peptides modified by a single Hda or palmitoyl-lysine residue. Resolution of the diastereoisomers contained in the Hda-V3S peptide could be obtained by this method, with a yield of 10 and 12% for the first and the second collected peak, respectively. The V3S-CholLys and CholLys-V3S peptides were obtained with lower yields (5 and 10.5%, respectively), due to the lability of the 3$\beta$ O-steroid bond towards the prolonged acidic cleavages that were necessary to deprotect the arginine residues from the Pmc groups. Purification yields for the longer sequences were of 17.5% for the V3L peptide, 5% for the V3L-Hda, and 8% for the V3L-MPLys peptide.

Figure 6:
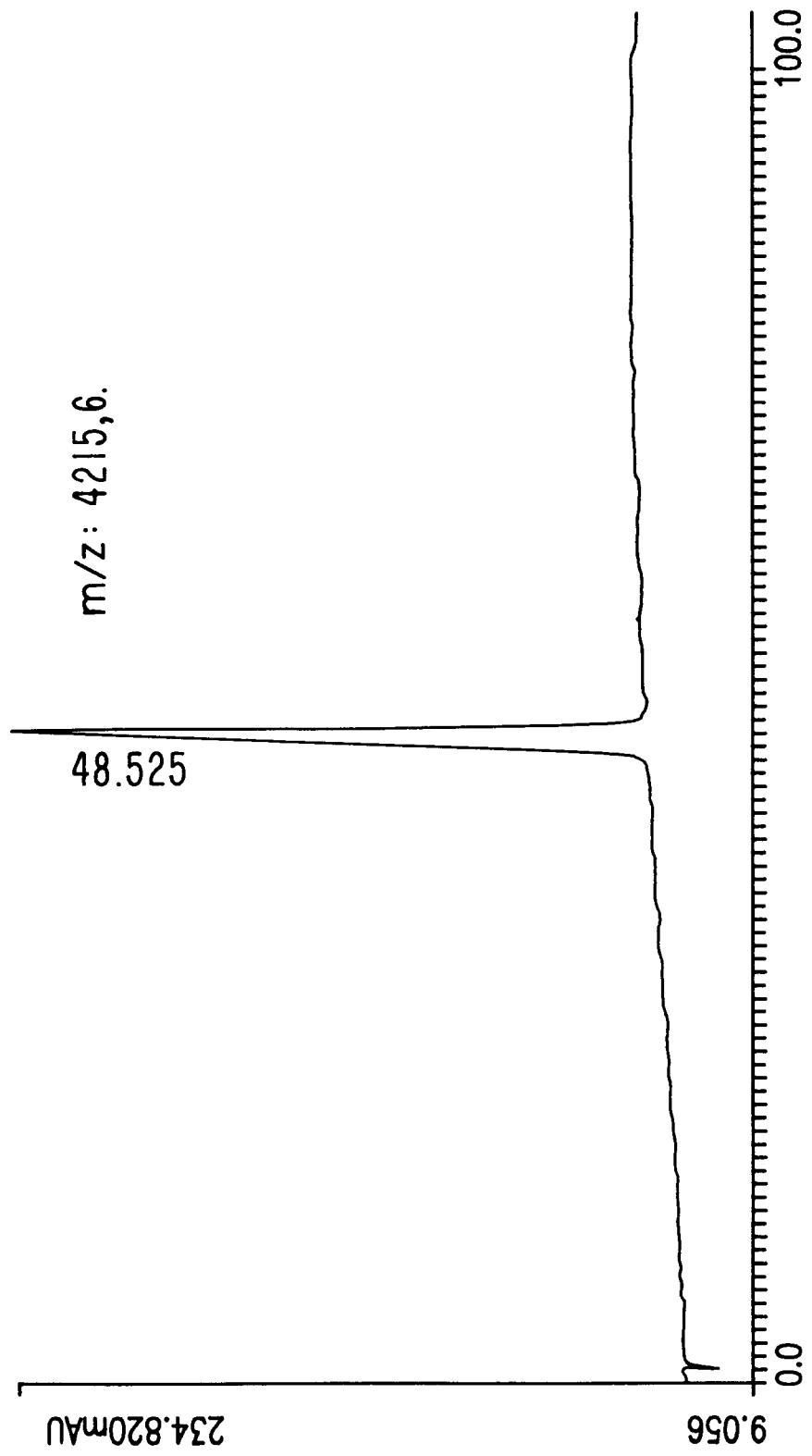
FIG. 6 illustrates the RP-HPLC analysis of the peptide V3L-MPLys, on a Vydac C4 7 μm, 300 Å (4,6×250 mm) column. Injection : 50 μl of an 1 mg/ml solution. Solvent composition : A: 0,05% TFA in water; B: 0,05% TFA in acetonitrile: water 80:20. Gradient: from 0 to 100% in 100 minutes. Flow rate: 1 ml/min.

Homogeneity of the purified peptides was checked by analytical RP-HPLC. Lipopeptides, even with long sequences, modified by the L-lysine-derived lipophilic amino acids eluted as a symetric peaks, which can be used to determine their purity (FIG. 6). Conversely, peptides modified by the $\alpha$-aminohexadecanoïc acid eluted as shouldered peaks resulting from the presence of diastereoisomers, although the presence of impurity could not be excluded from the chromatographic profile. In the case of the Hda-V3S peptide, even the doublet corresponding to the diastereoisomers was observed, assessing the resolutive power of our analytical procedures. Nevertheless, in our conditions, RP-HPLC resolution was not possible with the C-terminally modified V3S-Hda or V3L-Hda.

Purified peptides had the expected amino acid composition, as determined by amino acid analysis after total acid hydrolysis. Incorporation of the lipidic component was assessed by molecular mass determination, determined by Plasma Desorption Mass Spectrometry for mono-substituted peptides, after RP-HPLC purification. Mass determination was not possible for peptides DPLys-V3S-Hda, Hda-V3S-Hda, DPLys-V3L-Hda, and Hda-V3L-Hda. As these peptides were obtained by N-terminal elongation of the same peptidyl-resin than the analog V3S-Hda and V3L-Hda, it was assumed that the incorporation of the C-terminal lipidic was effective after monitoring using a qualitative ninhydrine test.

In vivo induction of virus-specific CTL response. Criteria of positivity.

The criteria retained in this paper have been described hereabove. Briefly, the capacity of the different peptide constructs to induce without any adjuvant, a virus-specific CTL response was evaluated with reference to the results obtained when immunizing with the living vac-env, recombinant virus, i.e. according to the delay before detection of cytolytic activity (<day 14), and the ability to lyse virus-infected target cells.

All mice were individually tested. Representative experiments are shown in FIGS. 7a and 7b. CTL activity, able to lyse specifically both peptide-pulsed and vac-env infected P815 target cells could be detected in a Balb/c mouse after subcutaneous priming with 50 nanomoles of the V3S-Hda peptide, in saline, followed by a booster injection 15 days later under identical conditions (FIG. 7a).

The efficiency of our different constructs was thus expressed in terms of the relative number of animals in which a virus-specific CTL activity was observed after subcutaneous priming with 50 nanomoles of a given compound. By contrast, we were unable to detect CTL activity in any of the 8 mice immunized in the same conditions with the unmodified V3S peptide (FIG. 7b).

CTL induction: comparative efficiency of the lipopeptides

As shown from results summarized in tables VIII and IX, several constructs were endowed of a high potency; for example, a virus specific CTL response was observed in sixteen out of the seventeen mice immunized in by the V3-SHda lipopeptide injected in pBS.

In our conditions, CTL activity was never detected in the animals immunized with the unmodified peptides V3S, and V3L, and exceptionnally observed in animals immunized with the Ac-V3S-NH$_2$ peptide: the simple protection towards the degradation by exopeptidases, by introduction of acetyl and carboxamide N and C-terminal extremities, was not sufficient to confer CTL-immunogenicity (a significant CTL activity could be detected in only 2 out of the 7 mice immunized with the Ac-V3S-NH$_2$ peptide).

Peptides modified at a single extremity by a lipidic amino-acid can induce a virus specific CTL response in most cases: this result is clearly reproducible when the C-terminal extremity was modified by an α-aminohexadecanoylamide residue, a Nε-palmitoyllysylamide residue, or with a Nε-cholesteryloxyacetyllysylamide residue (due to the low yields of synthesis and purification, only two mice were immunized with the CholLys-derived constructs).

Interestingly, modification of the long V3L peptide by a single lipidic amino acid (α-aminohexadecanoylamide or Nεpalmitoyllysylamide) is sufficient to confer CTL immunogenicity.

Results obtained with N-terminally modified constructs are less clear. As expected, the P3CSS-V3S construct was active, but no CTL were observed in mice immunized with the AcHda-V3S or SucHda-V3S peptides, modified by a N-terminally blocked α-aminohexadecanoïc acid residue. Six out the ten animals immunized with the Hda-V3S peptide were positive. The CholLys-V3S construct, modified by an acetylated lipidic amino acid was active in both immunized mice. The presence of a N-terminal Hda residue in a longer sequence is nevertheless compatible with activity in the Hda-V3L-Hda peptide.

None of the insoluble peptides (Hda-V3S-Hda, DPLys-V3S-Hda, and DPLys-V3L-Hda) were active. Insolubility rather than the ratio lipidic charge versus length appeared critical: the three palmitoyl chains present in the (soluble) P3CSS-V3S peptide were compatible with CTL-immunogenicity, althought in this case, the activity of the construct cannot be explained only by lipophilicity (the well known intrinsic immunoadjuvant properties of the P3CSS-moiety are presumably involved in the overall activity of this construct).

EXAMPLE 9

Immunization against various peptides from nucleoprotein NP coupled with alpha amino hexadecanoic rest:

All the peptides and lipopeptide equivalents used in this study contain CD8 epitopes (table X). Peptides NP50-63 (NP1) SEQ ID NO:29, NP147-158 R$_{156}$ (NP2) SEQ ID NO:1, NP147-155 (NP2S SEQ ID NO:1(amino acids 1-9)), NP365-379 (NP3) SEQ ID NO:30 and (NP50-63)-(NP147-158)-(NP365-379) (NP123) SEQ ID NO:31 are from the influenza A virus nucleoprotein.

The peptides were synthesized using the conventional solid-phase "Boc-benzyl strategy" in an automated Applied Biosystem 470A peptide synthesizer (Applied Biosystems, Foster City, USA), using double coupling and systematic capping with acetic anhydride. Tert-butyloxycarbonyl (t-Boc)Hda was synthesized and introduced as described hereabove.

The peptides were checked for homogeneity by analytical RP-HPLC, and their identity was checked by amino-acid analysis after acid hydrolysis. The incorporation of the exotic amino-acid alpha-amino-hexadecanoïc acid (Hda) was assessed by determining the molecular mass by plasma desorption mass spectrometry.

Viruses

A/Puerto Rico/8/34 (A/PR/8, H$_1$N$_1$) and A/New Texas (A/NT, H$_3$N$_2$) and B/Yamagata (B/Yam) influenza viruses were generously provided by C. Hannoun (Institut Pasteur, Paris, France). They were grown in embryonated chicken eggs and the filtered allantoic fluid was used for in vivo immunization of mice, and for in vitro infection of target cells in cytotoxicity assays.

Immunization of mice

BALB/c (H-2$^d$), C57BL/6 (B/6) (H-2$^b$), and B/6 X CBA F1 (H-2$^{b \times k}$) mice were purchased from Iffa Credo (l'Arbresles, France). Mice were primed s.c. or i.p. with 50 nanomoles of free peptide or lipopeptide in normal saline. They were boosted three weeks later using identical conditions. Their spleen was removed for CTL generation 2 or 24 weeks after the last injection. To study the induction of a T helper cell response, mice were immunized with lipopeptides in mild adjuvant (IFA). Their spleen was removed two weeks after the last injection.

IL-2 release assays.

Single spleen suspensions were made and the cells washed twice in RPMI 1640 before resuspension in RPMI 1640 supplemented with 100 U/ml penicillin, 100 μg/ml streptomycin, 2 mM L-glutamine, nonessential amino-acids, 1 mM sodium pyruvate, 10 mM HEPES, 50 μM 2-ME and 1% Nutridoma SP (Boehringer-Mannheim) at a concentration of $5.10^6$ cells/ml. A total of 100 μl of cell suspension was placed into round-bottomed microtiter wells (Costar) and peptides added at the indicated concentrations. Cultures were set up in triplicates. After a 24 hours incubation at 37 C and 5% $CO_2$, 100 μl/well of supernatant were transferred and tested for the IL-2+IL-4 content using the CTL.L2 line ($10^4$ cells/well). [$^3$H]thymidine was added (1 μCi/well) during the last 6 hours of a 24 hours incubation. The cells were harvested on an automatic cell harvester (Skatron Inc., Sterling Va., USA) and [$^3$H]thymidine incorporation was quantified by scintillation counting.

Generation of CTL

In vitro stimulation was performed by mixing $3.10^6$ responding cells with $6.10^6$ irradiated (4,000 rads) stimulating cells in 2 ml culture medium (RPMI 1640 supplemented with 100 U/ml penicillin, 100 μg/ml streptomycin, 2 mM L-glutamine, nonessential amino-acids, 1 mM sodium pyruvate, 10 mM HEPES, 50 μM 2-ME and 10% heat inactivated FCS). These stimulating cells were obtained by incubating $10.10^6$ syngeneic spleen cells from naive mice in 1 ml medium containing 30 μg synthetic peptide for 3 hours at 37° C. These cells were washed before use. In most experiments, an additional in vitro stimulation was performed one week later using stimulating cells prepared as described before in culture medium supplemented with 5% human IL-2 containing supernatant (19). The cytotoxicity was evaluated five to six days after each in vitro stimulation.

Cytotoxicity assays

The target cells used were P815 ($H-2^d$, DBA/2), RDM4 ($H-2^k$, CBA) and EL4 ($H-2^b$, B/6) tumor cell lines. Influenza virus-infected cells were obtained by incubating cells with 100 HAU influenza virus; they were used as targets 2 to 3 hours later. Peptide pulsed-target cells were prepared by a similar incubation with peptide (final concentration 20 μg/ml) and used immediately.

Uninfected or infected target cells were labelled with 100 μCi $Na_2^{51}CrO_4$ (CEA, Gif sur Yvette, France) for 90 min at 37° C. and washed twice. 5,000 target cells and serial dilutions of effector cells were then incubated in 200 μl culture medium in round-bottomed microtiter plates for 4 hours at 37° C., and the assay was terminated by gamma counting the supernatants. The % specific lysis was calculated as : 100 X (experimental-spontaneous release)/(total $^{51}Cr$ incorporated)- spontaneous release). Spontaneous release in the absence of effector cells was less than 20% of total $^{51}Cr$ incorporated in all experiments.

Results

Generation of influenza nucleoprotein-specific CTL by lipopeptide constructs.

We synthesized a NP2 peptide (Lipo-NP2) modified as described hereabove in the V3 ENV model by additing a C-terminal amino-acid possessing a 14-carbon aliphatic side chain without known adjuvant properties. We injected this into BALB/c mice, both i.p. and s.c. Lipo-NP2 induced H-2d restricted influenza virus specific CTL responses, when given by either route (FIG. 8). The free peptide was not immunogenic when injected under the same conditions. Thus lipopeptides containing a simple modifying lipid amino-acid can induce comparable CTL responses in different viral systems.

Influence of T helper cells on in vivo priming with lipopeptides

Figure 9B:
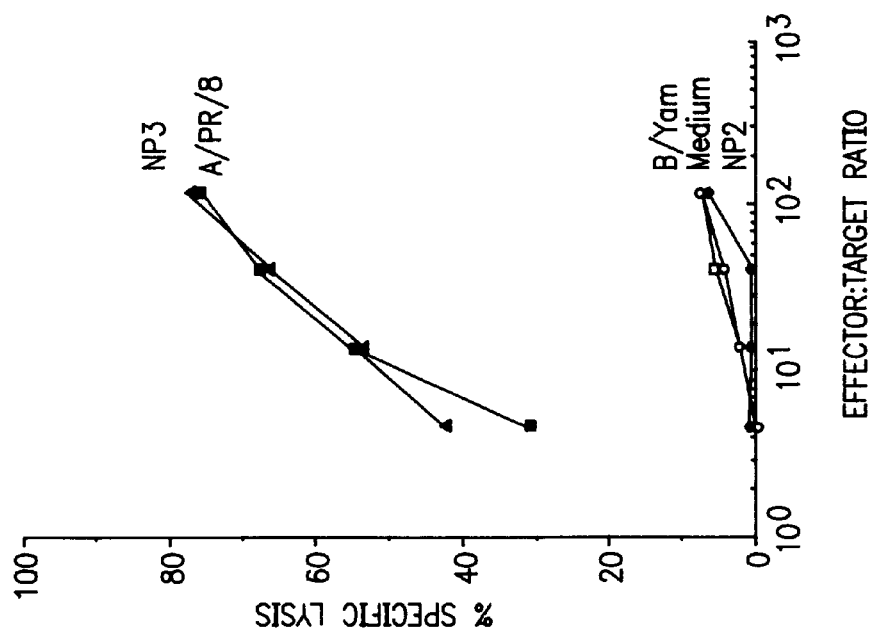
Figure 9A:
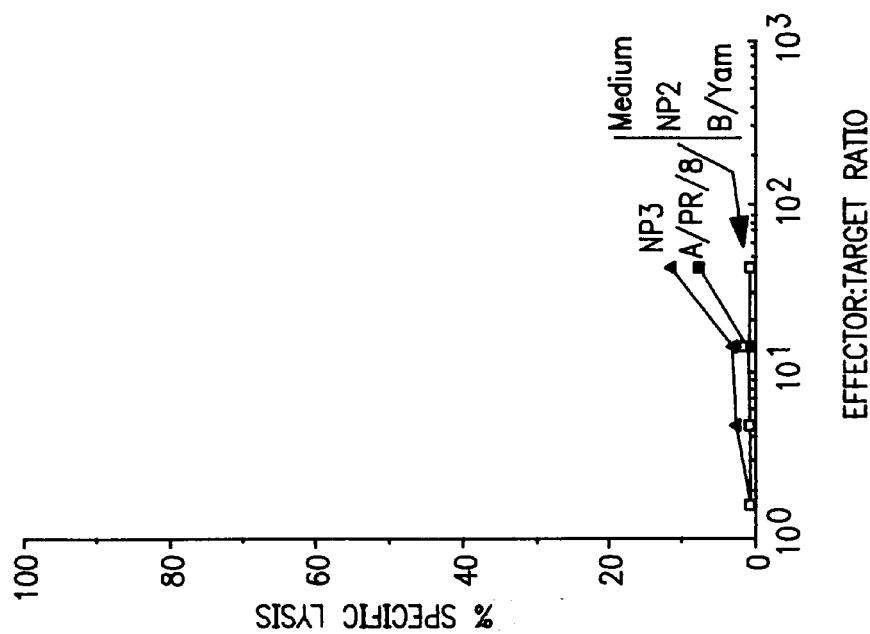

The tests on the construct Lipo-NP3, which includes a known $H-2^b$-restricted CTL epitope of the influenza virus nucleoprotein (table X) revealed no CTL response in B/6 mice (FIG. 9a), even when IFA was used for priming. One explanation for this could be a lack of T helper cell activation. The synthetic peptides V3L and NP2 have been shown to induce specific CD4+ T helper responses in BALB/c mice, whereas NP3, although it includes a CTL epitope, contains no CD4 epitope in this H-2 haplotype (table X). The corresponding lipopeptide (Lipo-NP3) generated no T helper cell response as measured by specific IL-2 secretion following in vitro stimulation assay in B /6 mice (FIG. 9C). Since peptide NP3 is known to activate T helper cells in the $H-2^k$ haplotype, we checked that Lipo-NP3 was effective at inducing a T helper cell response in H-2 b×k haplotype (FIG. 9d). Due to subtype-specific mutations between the sequence of NP3 from A/PR/8 used in this study and the corresponding sequence from other A strains, the CTL response was studied on target cells infected with the A/PR/8 strain. In addition to a specific T helper cell induction, FIG. 9b shows that F1 mice were also able to generate a virus specific CTL response to Lipo-NP3. The free unmodified NP3 peptide was not immunogenic in these F1 mice.

Immunogenicity of lipopeptide constructs including long synthetic sequences.

The capacity of long lipopeptide sequences that included several different CD8 and CD4 epitopes to induce CTL was tested. Several CD8 epitopes were incorporated into a construct that had a long synthetic sequence containing three colinear CTL epitopes of the influenza nucleoprotein, each with a different H-2 restriction. This NP123 lipopeptide (see table X) was first injected s.c. into BALB/c mice which should normally respond to the central epitope, NP2. The $H-2^d$- restricted virus-specific CTLs were primed with both Lipo-NP2 (FIG. 8) and Lipo-NP123 (FIG. 10a) suggesting that NP2 is still immunogenic even when it is in the center of a much longer sequence.

The immunogenicity of the N-terminal NP1 sequence was then evaluated in CBA mice. FIG. 10b shows that strong $H-2^k$-restricted virus-specific CTL activities were also elicited in this H-2 haplotype with the LipoNP-123 construct.

We finally tested the same construct in F1 mice whose $H-2^{b \times k}$ hybrid haplotype should allow induction of a CTL response to the C-terminal (NP3) epitope. The Lipo-NP123 construct also effectively produced NP3-specific $H-2^b$-restricted CTL in F1 mice (FIG. 10C). Lipo-NP123 did not induce NP1-specific $H-2^k$- restricted CTL in these F1 mice, suggesting that there is an immunodominantly regulated response to NP1 within Lipo-NP123 in this particular context.

Long-term CTL in mice Primed with lipopeptides.

Lastly, we evaluated the ability of lipopeptide constructs to induce long-term cytotoxic responses, as this is a major parameter in the design of any vaccine. The CTL responses to influenza virus NP were studied for up to six months after the last injection. The spleens of BALB/c and F1 mice immunized s.c. with Lipo-NP123 six months earlier were restimulated in vitro either with peptides NP2 or NP3. Strong specific CTL responses to these peptides were still present in BALB/c and F1 mice, respectively (FIGS. 11a and 11b).

Discussion

We first evaluated the ability of lipopeptide constructs bearing simple lipid amino-acid in the C-term position to reproducibly induce virus-specific CTL responses in a viral model. Deres et al. (Nature 1989, 342-561) described how influenza virus-specific CTL responses could be generated using a synthetic peptide containing a known $H-2K^d$-restricted CTL epitope of the nucleoprotein, provided that it was chemically linked to a built-in lipotripeptide immunoadjuvant possessing polyclonal activator properties. Immunizing BALB/c mice with our NP2 derived lipopeptide, without adjuvant, we actually obtained a virus-specific response. Although the NP3 lipopeptide failed to induce a virus-specific CTL response into B/6 (H-$2^b$) mice, it succeeded in the H-$2^{b \times k}$ hybrid haplotype, which allowed generation of a concomitant H-$2^k$-restricted T helper cell response. These results suggest that T helper cells are required for efficient CTL induction at least in these cases and when using 11 to 15-mer long lipopeptides. The necessity for T helper cells was also confirmed by the use of a lipopeptide construct that included the nine-mer NP2S sequence corresponding to the CDB epitope within NP2 (see table X). Neither the peptide nor the lipopeptide NP2S induced T helper and CTL responses in BALB/c when injected s.c. even when the injections were done with IFA.

The conditions of immunization are important for generating persisting effectors, an essential consideration for the purposes of a vaccine. The results with long lipopeptides show that specific CTL responses persist for up to six months after the last injection, which is a long time in the life of a mouse.

Since each individual has the potential to present a particular set of dominant epitopes for CTL recognition, due to the MHC presentation of these epitopes, an effective vaccine should allow generation of virus-specific CTL in as diverse a population as possible. The use of long synthetic sequences containing several CD8 and CD4 epitopes for human vaccination is therefore of particular interest.

Several epitopes used in the SIV-derived lipopeptides to immunize macaques were chosen because they shared significant homologies with HIV sequences known to be epitopic in HIV-1 infected individuals, in contrast to the well defined epitopes described in the present study. We evaluated in mice a "maximal" construction by testing a 41 amino-acid long lipopeptide (Lipo-NP123) that included the sequences of NP1, NP2 and NP 3 peptides (see table X) plus a C-terminal Hda residue. The immunogenicity of the NP2 peptide in BALB/c mice was completely retained, even when the peptide lay within a 41-residue peptide. Both the N-terminal NP1 and C-terminal NP3 peptides were also immunogenic in CBA and B/6 X CBA F1 mice respectively. Since all our constructs are modified at the C-term end of the peptide, this result suggests that the immunogenicity of the peptide does not depend on its distance from the lipophilic moiety. When the responses to the two external epitopes were tested in the same hybrid H-$2^{b \times k}$ haplotype, H-2b restricted CTL activity was dominant over H-2k restricted activity, suggesting that there was immunodominance within the NP123 sequence, as observed in F1 mice immunized with influenza-virus and restimulated with the virus in vitro. Thus, the lipopeptide construct and the whole internal nucleoprotein synthesized inside the cell seem to behave in a similar way, both for processing and MHC-class I presentation.

Conclusion

These CTL found in these experiments are clearly primed in vivo.

These results demonstrate that naturally processed peptides are recognized at the stimulator as well as at the effector stages of the immune response by lipopeptides induced CTL.

A major interest of vaccination with lipopeptides found in these experiments is the persistence in peripheral blood of a detectable CTL precursor activity for at least 10 months. Humoral immune response usually declines quickly after immunization although memory B cells persist at a low level and can be further reactivated. After immunization, one expected a decrease in CTL activity with homing of memory CTL within lymphoid organs and few circulating memory cells. The persistence of a strong activity, detected in macaques, in circulating PBMC at least 10 months after the last immunization suggests a high frequency of memory CTL precursors.

Interests of lipopeptidic vaccines are multiple. Lipopeptides are safe, without side effects, and the protocol of vaccination could be easily applicable to humans. Moreover, the response will not be hampered by a preexisting immune response against the vector as observed with recombinant viruses (Cooney, E. L. et al. 1991. Lancet 337:567). In addition, lipopeptides allow the induction of antibodies; anti NEF and GAG antibodies were detected in the SIV-lipopeptide study but are unlikely to be efficient for protection. However, neutralizing antibodies have been obtained in mice by immunization against ENV (HIV1)—derived lipopeptides. Therefore, the association of lipopeptides inducing CTL to other lipopeptides capable to generate antibodies should result in efficient protection.

TABLE I

ANTI-NP 147-158R PEPTIDE IMMUNIZATIONS (influenza virus)

| In vivo injection | In vitro stimulation | Target | Cytolytic activity | | |
|---|---|---|---|---|---|
| | | | d5 | d12 | ≥d21 |
| 0 | NP.147-158R⁻ | NP.147-158R⁻(a) | – | – | ++ |
| | | Influ. virus(b) | | | (+) |
| Influ. virus | NP.147-158R⁻ | NP.147-158R⁻ | (++) | (++) | (+++) |
| | | Influ. virus | (++) | (++) | (+++) |
| NP.147-158R | NP.147-158R⁻ | NP.147-158R⁻ | (–) | – | + |
| | | Influ. virus | (–) | – | |
| P3CSS-Pep .NP | Influ. virus | Influ. virus | (–) | | |
| | NP.147-158R⁻ | NP.147-156R⁻ | (++) | | |
| | | Influ. virus | (++) | | |
| | | P3CSS-Pep. NP. | (++) | | |
| LIPOSOME-Pep.NP. | | | | | |
| [1* s.c. syntex][c] | NP.147-158R⁻ | NP.147-158R⁻ | – | – | |
| [1* i.p.] | NP.147-158R⁻ | NP.147-158R⁻ | – | – | |
| [2* s.c. syntex] | NP.147-158R⁻ | NP.147-158R⁻ | – | ++ | |
| [2* i.p.] | NP.147-158R⁻ | NP.147-158R⁻ | – | ++ | |
| LIPOPEPTIDES-Pep.NP. | | | | | |
| L1-Pep.NP. [2* i.p.] | NP.147-158R⁻ | NP.147-158R⁻ | – | +++ | |
| | | Influ. virus | – | | |

TABLE I-continued

ANTI-NP 147-158R PEPTIDE IMMUNIZATIONS (influenza virus)

| In vivo injection | In vitro stimulation | Target | Cytolytic activity d5 | d12 | ≥d21 |
|---|---|---|---|---|---|
| L2-Pep.NP. [2* i.p.] | NP.147-158R⁻ | L1-Pep.NP. | +++ | +++ | |
| | | NP.147-158R⁻ | – | – | |
| | | Influ. virus | – | – | |
| L3-Pep.NP. [2* i.p.] | NP.147-158R | L1-Pep.NP. | – | – | |
| | | NP.147-158R⁻ | – | – | |
| | | Influ. virus | – | – | |
| | | L1-Pep.NP. | – | – | |

The results in brackets have already been published.
[a] syngenic target cells in the presence of 3 μm of the peptide NP.147-158 R
[b] syngenic target cells infected by the virus influenza A
[c] liposomes loaded with peptide NP 147-158 R.

TABLE II

ANTI-ENV. 312-327 PEPTIDE IMMUNIZATIONS (HIV-BRU) by $CB_1$, $CB_2$ and $CB_6$

| In vivo injection | In vitro stimulation | Target | Cytolytic activity d5 | d12 | ≥d21 |
|---|---|---|---|---|---|
| 0 | ENV.312-327 | ENV.312-327[a] | – | – | ++ |
| | | Vac-env[b] | – | – | – |
| Vac-env | CBI | ENV.312-327 | – | – | |
| | ENV.312-327 | ENV.312-327 | (++) | | |
| | | Vac-env | (++) | | |
| ENV.312-327 | ENV.312-327 | ENV.312-327 | – | – | ++ |
| | | Vac-env | – | – | – |
| LIPOPEPTIDES-ENV.312-327 | | | | | |
| CB1 [1* i.p.] | ENV.312-327 | ENV.312-327 | – | | |
| CB1 [2* i.p.] | ENV.312-327 | ENV.312-327 | +++ | +++ | +++ |
| | | Vac-env | +++ | +++ | +++ |
| CB1 [1* s.c.syntex] | ENV.312-327 | ENV.312-327 | – | | |
| CB1 [2* s.c.syntex] | ENV.312-327 | ENV.312-327 | ++ | | |
| | | Vac-env | ++ | | |
| CB2 [2* i.p.] | ENV.312-327 | ENV.312-327 | – | ++ | |
| | | Vac-env | – | ++ | |
| CB3 [2* i.p.] | ENV.312-327 | ENV.312-327 | – | – | |
| | | Vac-env | – | – | |

[a] syngenic target cells in the presence of 3 μM of peptide INV 312-327
[b] syngenic target cells infected by a vaccine virus allowing the expression of the gene env of HIV

TABLE III

ANTI-ENV.302-335 PEPTIDE IMMUNIZATIONS (HIV-BRU)

| In vivo injection | In vitro stimulation | Target | Cytolytic activity d5 | d12 | ≥d21 |
|---|---|---|---|---|---|
| ENV.302-336 | ENV.302-336 or ENV. 312-327 | ENV.312-327[a] | – | – | |
| LIPOPEPTIDES-ENV. 302-335 | | | | | |
| CB6 [2* i.p.] | ENV. 302-336 or ENV.312-327 | ENV.312-327[a] Vac-env[b] | ++ | +++ | |
| CB7 [2* i.p.] | ENV. 302-336 or ENV.312-327 | ENV.312-327 Vac-env | | ++ | +++ |
| CB8 [2* i.p.] | ENV.302-336 or ENV.312-327 | ENV.312-327 Vac-env | – | – | – |

(a) and (b) : cf TABLE II

TABLE IV

Anti-Env.312-327 peptide immunizations by $CB_1$, $CB_4$, $CB_{17}$, $CB_{19}$, $CB_{21}$, $CB_{25}$ and $CB_5$

| | | | cytotoxic activity | |
|---|---|---|---|---|
| in vivo injection | in vitro stimulation | target | <14 days | >21 days |
| CB1 (2 × s.c.) | ENV 312-327 | ENV 312-327[a] | +++ | +++ |
| | | Vac-ENV[b] | +++ | +++ |
| | | CB1 | +++ | +++ |
| CB4 (2 × i.p.) | ENV 312-327 | ENV 312-327 | +++ | +++ |
| | | Vac-ENV | +++ | +++ |
| CB17 (2 × i.p.) | ENV 312-327 | ENV 312-327 | − | ++ |
| | | Vac-ENV | − | + |
| CB19 (2 × i.p.) | ENV 312-327 | ENV 312-327 | + | ++ |
| | | Vac-ENV | − | + |
| CB21 (2 × i.p.) | ENV 312-327 | ENV 312-327 | ++ | +++ |
| | | Vac-ENV | ++ | +++ |
| CB25 (2 × i.p.) | ENV 312-327 | ENV 312-327 | +++ | NT |
| | | Vac-ENV | ++ | |
| CB25 (2 × i.p. FIA) | ENV 312-327 | ENV 312-327 | ++ | NT |
| | | Vac-ENV | + | |
| CB25 (3 × i.p.) | ENV 312-327 | ENV 312-327 | +++ | NT |
| | | Vac-ENV | ++ | |
| CB25 (3 × i.p. FIA) | ENV 312-327 | ENV 312-327 | ++ | NT |
| | | Vac-ENV | ++ | |
| CB25 (2 × s.c.) | ENV 312-327 | ENV 312-327 | +++ | NT |
| | | Vac-ENV | ++ | |
| CB25 (2 × s.c. FIA) | ENV 312-327 | ENV 312-327 | +++ | NT |
| | | Vac-ENV | +++ | |
| CB25 (3 × s.c.) | ENV 312-327 | ENV 312-327 | +++ | NT |
| | | Vac-ENV | ++ | |
| CB25 (2 × s.c. FIA) | ENV 312-327 | ENV 312-327 | +++ | NT |
| | | Vac-ENV | +++ | |
| CB5 (2 × i.p.) | ENV 312-327 | ENV 312-327 | ++ | +++ |
| | | Vac-ENV | ++ | +++ |

(a) and (b): cf table II

TABLE V

Cytolytic activities found in 12 immunized macaques

| Effector cells[a] | | Target | % specific lysis[c] at E/T ratio[d] of: | | | |
|---|---|---|---|---|---|---|
| Macaque* | CD4/CD8 ratio[e] | cells[b] | 70:1 | 23:1 | 7:1 | 2:1 |
| RS4 | 56/31 | HP | 8 | 7 | 2 | 0 |
| | | HP-GAG 165-195 | 60[f] | 64 | 63 | 48 |
| RS7 | 4/78 | HP | 20 | 18 | 10 | 4 |
| | | HP-GAG 246-281 | 59 | 41 | 25 | 12 |
| RS23 | 39/44 | HP | 18 | 10 | 4 | 1 |
| | | HP-NEF 201-225 | 42 | 29 | 8 | 2 |
| Q50 | 44/38 | — | | | | |
| Q51 | 48/39 | — | | | | |
| RS6 | 50/32 | HP | 11 | 11 | 9 | 6 |
| | | HP-NEF 155-178 | 40 | 34 | 21 | 11 |
| Q53 | 27/56 | — | | | | |
| Q54 | 54/31 | — | | | | |
| RS17 | 21/72 | HP | 0 | 0 | 0 | |
| | | HP-NEF 155-178 | 44 | 43 | 28 | |
| RS20 | 34/47 | HP | 5 | 5 | 0 | |
| | | HP-NEF 125-147 | 70 | 64 | 38 | |
| | | HP-NEF 155-178 | 53 | 42 | 20 | |
| RS21 | 43/51 | HP | 23 | 20 | 18 | |
| | | HP-NEF 201-225 | 35 | 29 | 20 | |
| RS22 | 36/50 | — | | | | |

Legends table V:
[a]PBMC were obtained from 12 immunized macaques and restimulated by the mixture of the 7 peptides in vitro.
[b]target cells were autologous B-LCL immortalized by the herpes papio virus and incubated with peptide (20 μM).
[c]target cells (5 · 10³) were labeled with $^{51}$Cr and incubated for 4 hours with various numbers of effector cells.
[d]E/T ratio, effector to target ratio.
[e]phenotypes were performed on cell cultures just before the CRT.
[f]CRT was considered as positive if the specific chromium release observed against peptide-pulsed target cells exceeded that observed on B-LCL without peptide by more than 10% at the highest E:T ratio.

TABLE VI

CTL recognized autologous target cells infected with vaccinia virus

| Effector cells[a] | | % Specific lysis[c] at E/T ratio[d] of: | | | |
|---|---|---|---|---|---|
| Macaque * | Target cells[b] | 210:1 | 70:1 | 23:1 | 7:1 |
| RS4 | HP-VAC-WT | 22 | 14 | 11 | 2 |
| | HP-VAC-GAG | 70[e] | 51 | 32 | 36 |
| RS6 | HP-VAC-WT | 16 | 2 | 0 | 0 |
| | HP-VAC-NEF | 36 | 11 | 1 | 0 |
| RS7 | HP-VAC-WT | 34 | 22 | 23 | 21 |
| | HP-VAC-GAG | 46 | 37 | 22 | 25 |
| RS23 | HP-VAC-WT | 43 | 16 | 17 | 8 |
| | HP-VAC-NEF | 64 | 34 | 21 | 11 |
| RS17 | HP-VAC-WT | | 10 | 3 | 5 |
| | HP-VAC-NEF | | 17 | 7 | 9 |
| RS20 | HP-VAC-WT | 11 | 3 | 8 | 4 |
| | HP-VAC-NEF | 30 | 22 | 23 | 17 |
| RS21 | HP-VAC-WT | 22 | 22 | 27 | 8 |
| | HP-VAC-NEF | 61 | 50 | 52 | 23 |

Legends Table VI:
[a]PBMC were obtained from 12 immunized macaques and restimulated by the mixture of the 7 peptides in vitro.
[b]target cells were autologous B-LCL immortalized by the herpes papio virus and infected with a wild type (WT) or Nef or Gag recombinant vaccinia virus.
[c]target cells (5 · 10³) were labeled with $^{51}$Cr and incubated for 4 hours with various numbers of effector cells.
[d]E/T ratio, effector to target ratio.
[e]CRT was considered as positive if the specific chromium release observed against target cells presenting SIV antigens exceeded that observed on targets infected with the wild type vaccinia virus by more than 10% for 210:1 E/T ratio or 5% for 70:1 E:T ratio.

TABLE VII

Fine specificities of CTL

| Peptides | Specific cytolytic activity for monkey and E/T ratio[a] | | | | | | | |
|---|---|---|---|---|---|---|---|---|
| | RS4 | | RS17 | | RS20 | | RS23 | |
| (amino acid position) | 60:1 | 20:1 | 60:1 | 20:1 | 60:1 | 20:1 | 60:1 | 20:1 |
| NEF 125-147 | | | | | 72 | 76 | | |
| NEF 125-138 | | | | | 70 | 85 | | |
| NEF 133-147 | | | | | 0 | 4 | | |
| NEF 155-178 | | | 44 | 43 | 74 | 87 | | |
| NEF 155-169 | | | 0 | 0 | 12 | 14 | | |
| NEF 160-176 | | | 0 | 0 | 0 | 6 | | |
| NEF 164-178 | | | 42 | 46 | 47 | 49 | | |
| NEF 201-225 | | | | | | | 23 | 14 |
| NEF 201-215 | | | | | | | 18 | 11 |
| NEF 211-225 | | | | | | | 0 | 0 |
| GAG 165-195 | 52 | 57 | | | | | | |
| GAG 165-185 | 9 | 8 | | | | | | |
| GAG 176-195 | 44 | 35 | | | | | | |

TABLE VII-continued

| | Fine specificities of CTL | | | | | | | |
|---|---|---|---|---|---|---|---|---|
| Peptides | Specific cytolytic activity for monkey and E/T ratio[a] | | | | | | | |
| (amino acid | RS4 | | RS17 | | RS20 | | RS23 | |
| position) | 60:1 | 20:1 | 60:1 | 20:1 | 60:1 | 20:1 | 60:1 | 20:1 |

[a]The CRT was performed after 3 in vitro stimulations of PBMC from immunized macaques. Target cells were prepared from autologous B-LCL. The percent specific chromium release was measured for each target cell incubated with each peptide. The lysis of autologous B-LBL without peptide was always less than 5%. E/T ratio, effector to target ratio.

TABLE VIII

COMPARATIVE EFFICIENCY OF PEPTIDE DERIVED FROM THE 312–327 SEQUENCE.

| denomination | construction | positive/total |
|---|---|---|
| V3S | H— 312–327 —OH | 0/8 |
| Ac—V3—NH$_2$ | Ac— 312–327 —NH$_2$ | 2/7 |
| P3CSS—V3S | P$_3$CSS— 312–327 —OH | 2/2 |
| V3S—Hda | H— 312–327 —Hda—NH$_2$ | 16/17 |
| Hda—V3S—Hda | H—Hda— 312–327 —Hda—NH$_2$ | 1/3 |
| Hda—V3s | H—Hda— 312–327 —OH | 6/10 |
| AcHda—V3S | Ac—Hda 312–327 —OH | 0/6 |
| SucHda—V3s | Suc—Hda 312–327 —OH | 0/6 |
| DPLys—V3S—Hda | (N$^{\alpha,\varepsilon}$-dipalmitoyl)Lys— 312–327 —Hda—NH$_2$ | 0/3 |
| V3S—MPLys | H— 312–327 —(N$^\varepsilon$palmitoyl)Lys—NH$_2$ | 7/9 |
| V3S—CholLys | H— 312–327 —(N$^\varepsilon$-cholesteryloxyacetyl)Lys— | 2/2 |
| Chol—LysV3s | N$^\alpha$—Ac, (N$^\varepsilon$-cholesteryloxyacetyl)Lys— 312–327 —OH | 2/2 |

312–327: IRIQRGPGRAFVTIGK
Results are expressed as the number of animals in which a virus-specific CTL activity was observed, relative to the total number of animals primed with 50 nanomoles of a given compound in saline.

TABLE IX

COMPARATIVE EFFICIENCY OF PEPTIDE DERIVED FROM THE 302–335 SEQUENCE.

| denomination | construction | positive/total |
|---|---|---|
| V3L | H— 302–336 —OH | 1/7 |
| V3L—Hda | H— 302–335 —Hda—NH$_2$ | 5/5 |
| Hda—V3L—Hda | H—Hda— 302–335 —Hda—NH$_2$ | 3/3 |
| DPLys—V3L—Hda | (N$^{\alpha,\varepsilon}$-dipalmitoyl)Lys— 302–335 —Hda—NH$_2$ | 0/3 |
| V3L—MPLys | H— 302–335 —(N$^\varepsilon$palmitoyl)Lys—NH$_2$ | 14/22 |

302–335: TRPNNNTRKSIRIQRGPGRAFVTIGKIGNMRQAH

TABLE X

Amino-acid sequence of peptides and lipopeptides used.

| Name | sequence[a,b] | H-2 class I restriction | H-2 class II restriction |
|---|---|---|---|
| NP1 | SDYEGRLIQNSLTI | K$^k$ (13) | I-A$^k$ (17) |
| NP2 | TYQRTRALVTG | K$^d$ (14) | 1-A$^d$ (17) |
| Lipo-NP2 | TYQRTRALVTG-Hda | | |
| NP2S | TYQRTRALV | K$^d$ (15) | — |

TABLE X-continued

Amimo-acid sequence of peptides and lipopeptides used.

| Name | sequence[a,b] | H-2 class I restriction | H-2 class II restriction |
|---|---|---|---|
| NP3 | IASNENMETMESSTL | $D^b$ (16) | 1-$A^k$ (17) |
| Lipo-NP3 | IASNENMETMESSTL-Hda | | |
| NP123 | SDYEGRLIQNSLTTTYQRTRALVTGIASNENMETMESSTL | $K^k, K^d, D^b$ | I-$A^k$, I-$A^d$ |
| Lipo-NP123 | SDYEGRLIQNSLTTTYQRTRALVTGIASNENMETMESSTL-Hda | | |

[a]The CTL determinant region is shown in bold type.
[b]Hda: Hexadecanoic acid.

---

What we claim:

1. A method of inducing cytotoxic T lymphocytes in warm-blooded animals comprising administering to warm-blooded animals an effective amount to induce cytotoxic T lymphocytes of a lipopeptide comprising a peptide having between 10 and 40 amino acids and at least one antigenic determinant, said lipopeptide also comprising at least one chain selected from the group consisting of pimelautide, trimexautide, hexadecanoic acid, 2-amino-hexadecanoic acid, steroid groups and derivatives thereof coupled on the $\alpha$-NH$_2$ and/or $\epsilon$-NH$_2$ functional groups of said amino acids.

2. The method of claim 1 wherein the chain is 2-aminohexadecanoic acid or one of its derivatives.

3. The method of claim 1 wherein the hexadecanoic acid is hexadecanoic acid or one of its derivatives.

4. The method of claim 1 wherein the chain is N-palmitoyllysine.

5. The method of claim 1 wherein the hexadecanoic derivative is N,N'-dipalmitoyllysine.

6. The method of claim 1 wherein the chain is pimelautide or trimexautide.

7. The method of claim 1 wherein the steroid is N-[(cholest-5-enyl-3-oxy)-acetyl]-lysine.

8. The method of claim 1 wherein the steroid is (cholest-5-enyl-3-oxy)-acetic acid.

9. The method of claim 1 wherein the peptide is a fragment of a protein of the HIV-1 or HIV-2 viruses.

10. The method of claim 1 wherein the peptide fragment is a fragment of the proteins encoded by the ENV-gene, the NEF-gene or the GAG-gene.

11. The method of claim 1 wherein the peptide is the 312-327 fragment, the 302-306 fragment or the 307-331 fragment of the protein encoded by the ENV-gene.

12. The method of claim 1 wherein the peptide is the 66-97 fragment, the 117-147 fragment or the 182-205 fragment of the protein encoded by the NEF-gene.

13. The method of claim 1 wherein the peptide is the 183-214 fragment or the 253-284 fragment of the protein encoded by the GAG-gene.

14. The method of claim 1 wherein the peptide part has between 10 and 20 amino acids.

15. A method of inducing cytotoxic T lymphocytes in warm-blooded animals comprising administering to warm-blooded animals an effective amount to induce cytotoxic T lymphocytes of a lipopeptide comprising a peptide having between 10 and 40 amino acids and at least one antigenic determinant, said lipopeptide also comprising at least one chain selected from the group consisting of pimelautide, trimexautide, hexadecanoic acid, 2-amino-hexadecanoic acid, steroid groups and derivatives thereof coupled on the $\alpha$-NH$_2$ functional groups of said amino acids.

16. A method of inducing cytotoxic T lymphocytes in warm-blooded animals comprising administering to warm-blooded animals an effective amount to induce cytotoxic T lymphocytes of a lipopeptide comprising a peptide having between 10 and 40 amino acids and at least one antigenic determinant, said lipopeptide also comprising at least one chain selected from the group consisting of pimelautide, trimexautide, hexadecanoic acid, 2-amino-hexadecanoic acid, steroid groups and derivatives thereof coupled on the $\epsilon$-NH$_2$ functional groups of said amino acids.

17. A method of inducing a CTL response specific for cancer tumor cells in humans comprising administering to humans an amount effective to induce a CTL response of a lipopeptide comprising a peptide having 10 to 40 amino acids and at least one antigenic determinant, said lipopeptide also comprising at least one chain selected from the group consisting of pimelautide, trimexautide, hexadecanoic acid, 2-amino-hexadecanoic acid, steroid groups and derivatives thereof coupled on the $\alpha$-N$_2$ and/or $\epsilon$-NH$_2$ groups of said amino acids.

* * * * *

UNITED STATES PATENT AND TRADEMARK OFFICE
CERTIFICATE OF CORRECTION

PATENT NO.    : 5,993,823
DATED         : November 30, 1999
INVENTOR(S)   : Boutillon et al It is certified that error appears in the above-identified patent and that said Letters Patent is hereby corrected as shown below:

<u>Title page,</u>
Item [73], Assignee, please change "Assignee:  Institut Pasteur de Lille, France" to -- Assignee:  Institut Pasteur de Lille and Institut National de la Sante et de la Recherche Medicale (INSERM), France --.

Signed and Sealed this

Thirteenth Day of May, 2003

JAMES E. ROGAN
*Director of the United States Patent and Trademark Office*

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 11
      (B) TYPE: amino acid
      (C) STRANDEDNESS: unknown
      (D) TOPOLOGY: linear (ii) MOLECULE TYPE: peptide (v) FRAGMENT TYPE: internal (vi) ORIGINAL SOURCE:
      (A) ORGANISM: Influenza (ix) FEATURE:
      (B) LOCATION: NP 147-158

(xi) SEQUENCE DESCRIPTION: SEQ ID NO:1:

Thr Tyr Gln Arg Thr Arg Ala Leu Val Thr Gly
 1         5                10

(2) INFORMATION FOR SEQ ID NO:2:

(i) SEQUENCE CHARACTERISTICS:
      (A) LENGTH: 16
      (B) TYPE: amino acid
      (C) STRANDEDNESS: unknown
      (D) TOPOLOGY: linear (ii) MOLECULE TYPE: peptide (v) FRAGMENT TYPE: internal (vi) ORIGINAL SOURCE:
      (A) ORGANISM: HIV-1

(ix) FEATURE:
      (B) LOCATION: ENV 312-327

(xi) SEQUENCE DESCRIPTION: SEQ ID NO:2:

Ile Arg Ile Gln Arg Gly Pro Gly Arg Ala Phe Val
 1         5                10

Thr Ile Gly Lys
       15

(2) INFORMATION FOR SEQ ID NO:3:

(i) SEQUENCE CHARACTERISTICS:
      (A) LENGTH: 35
      (B) TYPE: amino acid (C) STRANDEDNESS: unknown
           (D) TOPOLOGY: linear (ii) MOLECULE TYPE: peptide (v) FRAGMENT TYPE: internal (vi) ORIGINAL SOURCE:
           (A) ORGANISM: HIV-1

(ix) FEATURE:
           (B) LOCATION: ENV 302-335
           (D) OTHER INFORMATION: Xaa can be any amino
               acid (xi) SEQUENCE DESCRIPTION: SEQ ID NO:3:

Thr Arg Pro Asn Asn Asn Thr Arg Lys Ser Ile Arg
 1               5                  10

Ile Gln Arg Gly Pro Gly Arg Ala Phe Val Thr Ile
            15                  20

Gly Lys Ile Gly Asn Met Arg Gln Ala His Xaa
 25                  30                  35

(2) INFORMATION FOR SEQ ID NO:4:

(i) SEQUENCE CHARACTERISTICS:
           (A) LENGTH: 25
           (B) TYPE: amino acid
           (C) STRANDEDNESS: unknown
           (D) TOPOLOGY: linear (ii) MOLECULE TYPE: peptide (v) FRAGMENT TYPE: internal (vi) ORIGINAL SOURCE:
           (A) ORGANISM: HIV (ix) FEATURE:
           (B) LOCATION: ENV 307-331

(xi) SEQUENCE DESCRIPTION: SEQ ID NO:4:

Asn Thr Arg Lys Ser Ile Arg Ile Gln Arg Gly Pro
 1               5                  10

Gly Arg Ala Phe Val Thr Ile Gly Lys Ile Gly Asn
            15                  20

Met
 25

(2) INFORMATION FOR SEQ ID NO:5:

(i) SEQUENCE CHARACTERISTICS:
           (A) LENGTH: 32
           (B) TYPE: amino acid
           (C) STRANDEDNESS: unknown
           (D) TOPOLOGY: linear (ii) MOLECULE TYPE: peptide (v) FRAGMENT TYPE: internal (vi) ORIGINAL SOURCE:
           (A) ORGANISM: HIV (ix) FEATURE:
           (B) LOCATION: NEF 66-97

(xi) SEQUENCE DESCRIPTION: SEQ ID NO:5:

Val Gly Phe Pro Val Thr Pro Gln Val Pro Leu Arg
 1               5                  10

```
Pro Met Thr Tyr Lys Ala Ala Val Asp Leu Ser His
        15                  20

Phe Leu Lys Glu Lys Gly Gly Leu
25                  30

(2) INFORMATION FOR SEQ ID NO:6:

(i) SEQUENCE CHARACTERISTICS:
        (A) LENGTH: 31
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV (ix) FEATURE:
        (B) LOCATION: NEF 117-147

(xi) SEQUENCE DESCRIPTION: SEQ ID NO:6:

Ile Asp Met Ser His Phe Ile Lys Glu Lys Gly Gly
1               5                   10

Leu Glu Gly Ile Tyr Tyr Ser Ala Arg Arg His Arg
        15                  20

Ile Leu Asp Met Tyr Leu Glu
25                  30

(2) INFORMATION FOR SEQ ID NO:7:

(i) SEQUENCE CHARACTERISTICS:
        (A) LENGTH: 24
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV (ix) FEATURE:
        (B) LOCATION: NEF 182-205

(xi) SEQUENCE DESCRIPTION: SEQ ID NO:7:

Glu Trp Arg Phe Asp Ser Arg Leu Ala Phe His His
1               5                   10

Val Ala Arg Glu Leu His Pro Glu Tyr Phe Lys Asn
        15                  20

(2) INFORMATION FOR SEQ ID NO:8:

(i) SEQUENCE CHARACTERISTICS:
        (A) LENGTH: 32
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV (ix) FEATURE:
```

(B) LOCATION: GAG 183-214

(xi) SEQUENCE DESCRIPTION: SEQ ID NO:8:

Asp Leu Asn Thr Met Leu Asn Thr Val Gly Gly His
 1               5                  10

Gln Ala Ala Met Gln Met Leu Lys Glu Thr Ile Asn
            15                  20

Glu Glu Ala Ala Glu Trp Asp Arg
 25                  30

(2) INFORMATION FOR SEQ ID NO:9:

(i) SEQUENCE CHARACTERISTICS:
          (A) LENGTH: 32
          (B) TYPE: amino acid
          (C) STRANDEDNESS: unknown
          (D) TOPOLOGY: linear (ii) MOLECULE TYPE: peptide (v) FRAGMENT TYPE: internal (vi) ORIGINAL SOURCE:
          (A) ORGANISM: HIV (ix) FEATURE:
          (B) LOCATION: GAG 253-284

(xi) SEQUENCE DESCRIPTION: SEQ ID NO:9:

Asn Pro Pro Ile Pro Val Gly Glu Ile Tyr Lys Arg
 1               5                  10

Trp Ile Ile Leu Gly Leu Asn Lys Ile Val Arg Met
            15                  20

Tyr Ser Pro Thr Ser Ile Leu Asp
 25                  30

(2) INFORMATION FOR SEQ ID NO:10:

(i) SEQUENCE CHARACTERISTICS:
          (A) LENGTH: 29
          (B) TYPE: amino acid
          (C) STRANDEDNESS: unknown
          (D) TOPOLOGY: linear (ii) MOLECULE TYPE: peptide (v) FRAGMENT TYPE: internal (ix) FEATURE:
          (A) NAME/KEY: Theradigm-MART-AV
          (D) OTHER INFORMATION: initial Lys is N,N'-
              dipalmitoyllysine (xi) SEQUENCE DESCRIPTION: SEQ ID NO:10:

Lys Ser Ser Gln Tyr Ile Lys Ala Asn Ser Lys Phe
 1               5                  10

Ile Gly Ile Thr Glu Ala Ala Ala Ile Leu Thr Val
            15                  20

Ile Leu Gly Val Leu
 25

(2) INFORMATION FOR SEQ ID NO:11:

(i) SEQUENCE CHARACTERISTICS:
          (A) LENGTH: 29
          (B) TYPE: amino acid
          (C) STRANDEDNESS: unknown
          (D) TOPOLOGY: linear -continued

```
        (ii) MOLECULE TYPE:  peptide (v) FRAGMENT TYPE:  internal (ix) FEATURE:
             (A) NAME/KEY: Theradigm-MART-AV
             (D) OTHER INFORMATION: initial Lys is N,N'-
                 dipalmitoyllysine (xi) SEQUENCE DESCRIPTION: SEQ ID NO:11:

Lys Ser Ser Gln Tyr Ile Lys Ala Asn Ser Lys Phe
 1               5                  10

Ile Gly Ile Thr Glu Ala Ala Ala Ala Ala Gly Ile
            15                  20

Gly Ile Leu Thr Val
 25

(2) INFORMATION FOR SEQ ID NO:12:

(i) SEQUENCE CHARACTERISTICS:
             (A) LENGTH:  31
             (B) TYPE:  amino acid
             (C) STRANDEDNESS:  unknown
             (D) TOPOLOGY:  linear (ii) MOLECULE TYPE:  peptide (v) FRAGMENT TYPE:  internal (ix) FEATURE:
             (A) NAME/KEY: MART-1
             (D) OTHER INFORMATION: terminal Lys is N-n-
                 palmitoyllysine amide (xi) SEQUENCE DESCRIPTION: SEQ ID NO:12:

Lys Lys Gly His Gly His Ser Tyr Thr Thr Ala Glu
 1               5                  10

Glu Ala Ala Gly Ile Gly Ile Leu Thr Val Ile Leu
            15                  20

Gly Val Leu Leu Ile Gly Lys
 25                  30

(2) INFORMATION FOR SEQ ID NO:13:

(i) SEQUENCE CHARACTERISTICS:
             (A) LENGTH:  31
             (B) TYPE:  amino acid
             (C) STRANDEDNESS:  unknown
             (D) TOPOLOGY:  linear (ii) MOLECULE TYPE:  peptide (v) FRAGMENT TYPE:  internal (ix) FEATURE:
             (A) NAME/KEY: GP100
             (D) OTHER INFORMATION: terminal Lys is N-n-
                 palmitoyllysine amide (xi) SEQUENCE DESCRIPTION: SEQ ID NO:13:

Asp Phe Gly Asp Ser Ser Gly Thr Leu Ile Ser Arg
 1               5                  10

Ala Leu Val Val Thr His Thr Tyr Leu Glu Pro Gly
            15                  20

Pro Val Thr Ala Gln Val Lys
 25                  30
```

(2) INFORMATION FOR SEQ ID NO:14:

(i) SEQUENCE CHARACTERISTICS:
        (A) LENGTH: 29
        (B) TYPE: amino acid
        (C) STRANDEDNESS: unknown
        (D) TOPOLOGY: linear (ii) MOLECULE TYPE: peptide (v) FRAGMENT TYPE: internal (ix) FEATURE:
        (A) NAME/KEY: HA (xi) SEQUENCE DESCRIPTION: SEQ ID NO:14:

Pro Lys Tyr Val Lys Gln Asn Thr Leu Lys Leu Ala
1               5                   10

Thr Gly Met Arg Asn Val Pro Glu Lys Gln Thr Arg
            15                  20

Gly Leu Phe Gly Ala
25

(2) INFORMATION FOR SEQ ID NO:15:

(i) SEQUENCE CHARACTERISTICS:
        (A) LENGTH: 27
        (B) TYPE: amino acid
        (C) STRANDEDNESS: unknown
        (D) TOPOLOGY: linear (ii) MOLECULE TYPE: peptide (v) FRAGMENT TYPE: internal (ix) FEATURE:
        (A) NAME/KEY: 729NR1
        (D) OTHER INFORMATION: terminal Lys is N-n-
            palmitoyllysine amide (xi) SEQUENCE DESCRIPTION: SEQ ID NO:15:

Asp Glu Leu Phe Asn Glu Leu Leu Asn Ser Val Asp
1               5                   10

Val Asn Gly Glu Val Lys Glu Asn Ile Leu Glu Glu
            15                  20

Ser Gln Lys
25

(2) INFORMATION FOR SEQ ID NO:16:

(i) SEQUENCE CHARACTERISTICS:
        (A) LENGTH: 27
        (B) TYPE: amino acid
        (C) STRANDEDNESS: unknown
        (D) TOPOLOGY: linear (ii) MOLECULE TYPE: peptide (v) FRAGMENT TYPE: internal (ix) FEATURE:
        (A) NAME/KEY: 729NR2
        (D) OTHER INFORMATION: terminal Lys is N-n-
            palmitoyllysine amide (xi) SEQUENCE DESCRIPTION: SEQ ID NO:16:

Leu Glu Glu Ser Gln Val Asn Asp Asp Ile Phe Asn
1               5                   10

Ser Leu Val Lys Ser Val Gln Gln Glu Gln Gln His
            15                  20

Asn Val Lys
 25

(2) INFORMATION FOR SEQ ID NO:17:

(i) SEQUENCE CHARACTERISTICS:
        (A) LENGTH:  28
        (B) TYPE:  amino acid
        (C) STRANDEDNESS:  unknown
        (D) TOPOLOGY:  linear (ii) MOLECULE TYPE:  peptide (v) FRAGMENT TYPE:  internal (ix) FEATURE:
        (A) NAME/KEY: SALSA-1
        (D) OTHER INFORMATION: terminal Lys is N-n-
            palmitoyllysine amide (xi) SEQUENCE DESCRIPTION: SEQ ID NO:17:

Ser Ala Glu Lys Lys Asp Glu Lys Glu Ala Ser Glu
  1               5                  10

Gln Gly Glu Glu Ser His Lys Lys Glu Asn Ser Gln
         15                  20

Glu Ser Ala Lys
 25

(2) INFORMATION FOR SEQ ID NO:18:

(i) SEQUENCE CHARACTERISTICS:
        (A) LENGTH:  37
        (B) TYPE:  amino acid
        (C) STRANDEDNESS:  unknown
        (D) TOPOLOGY:  linear (ii) MOLECULE TYPE:  peptide (v) FRAGMENT TYPE:  internal (ix) FEATURE:
        (A) NAME/KEY: SALSA-2
        (D) OTHER INFORMATION: terminal Lys is N-n-
            palmitoyllysine amide (xi) SEQUENCE DESCRIPTION: SEQ ID NO:18:

Asn Gly Lys Asp Val Lys Glu Lys Lys Thr
  1               5                  10

Asn Glu Lys Lys Asp Asp Cys Lys Thr Asp Lys Val
         15                  20

Gln Glu Lys Val Leu Glu Lys Ser Pro Lys Glu Phe
 25                  30                  35

Lys (2) INFORMATION FOR SEQ ID NO:19:

(i) SEQUENCE CHARACTERISTICS:
        (A) LENGTH:  28
        (B) TYPE:  amino acid
        (C) STRANDEDNESS:  unknown
        (D) TOPOLOGY:  linear (ii) MOLECULE TYPE:  peptide (v) FRAGMENT TYPE:  internal (ix) FEATURE:
        (A) NAME/KEY: MSP3 b
        (D) OTHER INFORMATION: terminal Lys is N-n- palmitoyllysine amide (xi) SEQUENCE DESCRIPTION: SEQ ID NO:19:

Ala Lys Glu Ala Ser Ser Tyr Asp Tyr Ile Leu Gly
 1               5                  10

Trp Glu Phe Gly Gly Gly Val Pro Glu His Lys Lys
            15                  20

Glu Glu Asn Lys
25

(2) INFORMATION FOR SEQ ID NO:20:

(i) SEQUENCE CHARACTERISTICS:
        (A) LENGTH: 31
        (B) TYPE: amino acid
        (C) STRANDEDNESS: unknown
        (D) TOPOLOGY: linear (ii) MOLECULE TYPE: peptide (v) FRAGMENT TYPE: internal (ix) FEATURE:
        (A) NAME/KEY: MSP3 c
        (D) OTHER INFORMATION: terminal Lys is N-n-
            palmitoyllysine amide (xi) SEQUENCE DESCRIPTION: SEQ ID NO:20:

Pro Glu His Lys Lys Glu Glu Asn Met Leu Ser His
 1               5                  10

Leu Tyr Val Ser Ser Lys Asp Lys Glu Asn Glu Asn
            15                  20

Ile Ser Lys Glu Asn Glu Lys
25              30

(2) INFORMATION FOR SEQ ID NO:21:

(i) SEQUENCE CHARACTERISTICS:
        (A) LENGTH: 26
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (B) LOCATION: NEF 101-126

(xi) SEQUENCE DESCRIPTION: SEQ ID NO:21:

Ser Val Arg Pro Lys Val Pro Leu Arg Ala Met Thr
 1               5                  10

Tyr Lys Leu Ala Ile Asp Met Ser His Phe Ile Lys
            15                  20

Glu Lys
25

(2) INFORMATION FOR SEQ ID NO:22:

(i) SEQUENCE CHARACTERISTICS:
        (A) LENGTH: 23
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
             (A) ORGANISM: HIV-1

(ix) FEATURE:
             (B) LOCATION: NEF 125-147

(xi) SEQUENCE DESCRIPTION: SEQ ID NO:22:

Glu Lys Gly Gly Leu Glu Gly Ile Tyr Tyr Ser Ala
 1               5                  10

Arg Arg His Arg Ile Leu Asp Met Tyr Leu Glu
         15                  20

(2) INFORMATION FOR SEQ ID NO:23:

(i) SEQUENCE CHARACTERISTICS:
             (A) LENGTH: 24
             (B) TYPE: amino acid
             (C) STRANDEDNESS: unknown
             (D) TOPOLOGY: linear (ii) MOLECULE TYPE: peptide (v) FRAGMENT TYPE: internal (vi) ORIGINAL SOURCE:
             (A) ORGANISM: HIV-1

(ix) FEATURE:
             (B) LOCATION: NEF 155-178

(xi) SEQUENCE DESCRIPTION: SEQ ID NO:23:

Asp Trp Gln Asp Tyr Thr Ser Gly Pro Gly Ile Arg
 1               5                  10

Tyr Pro Lys Thr Phe Gly Trp Leu Trp Lys Leu Val
         15                  20

(2) INFORMATION FOR SEQ ID NO:24:

(i) SEQUENCE CHARACTERISTICS:
             (A) LENGTH: 25
             (B) TYPE: amino acid
             (C) STRANDEDNESS: unknown
             (D) TOPOLOGY: linear (ii) MOLECULE TYPE: peptide (v) FRAGMENT TYPE: internal (vi) ORIGINAL SOURCE:
             (A) ORGANISM: HIV-1

(ix) FEATURE:
             (B) LOCATION: NEF 201-225

(xi) SEQUENCE DESCRIPTION: SEQ ID NO:24:

Ser Lys Trp Asp Asp Pro Trp Gly Glu Val Leu Ala
 1               5                  10

Trp Lys Phe Asp Pro Thr Leu Ala Tyr Thr Tyr Glu
         15                  20

Ala
25

(2) INFORMATION FOR SEQ ID NO:25:

(i) SEQUENCE CHARACTERISTICS:

(A) LENGTH: 27
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (B) LOCATION: NEF 221-247

(xi) SEQUENCE DESCRIPTION: SEQ ID NO:25:

Tyr Thr Tyr Glu Ala Tyr Ala Arg Tyr Pro Glu Glu
  1               5                  10

Leu Glu Ala Ser Gln Ala Cys Gln Arg Lys Arg Leu
             15                  20

Glu Glu Gly
 25

(2) INFORMATION FOR SEQ ID NO:26:

(i) SEQUENCE CHARACTERISTICS:
        (A) LENGTH: 31
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: SIV (ix) FEATURE:
        (B) LOCATION: GAG 165-195

(xi) SEQUENCE DESCRIPTION: SEQ ID NO:26:

Lys Phe Gly Ala Glu Val Val Pro Gly Phe Gln Ala
  1               5                  10

Leu Ser Glu Gly Cys Thr Pro Tyr Asp Ile Asn Gln
             15                  20

Met Leu Asn Cys Val Gly Asp
 25                  30

(2) INFORMATION FOR SEQ ID NO:27:

(i) SEQUENCE CHARACTERISTICS:
        (A) LENGTH: 37
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: SIV (ix) FEATURE:
        (B) LOCATION: GAG 246-282

(xi) SEQUENCE DESCRIPTION: SEQ ID NO:27:

Gln Ile Gln Trp Met Tyr Arg Gln Gln Asn Pro Ile
  1               5                  10

```
Pro Val Gly Asn Ile Tyr Arg Arg Trp Ile Gln Leu
            15                  20
Gly Leu Gln Lys Cys Val Arg Met Tyr Asn Pro Thr
 25                  30                  35
Asn
```

(2) INFORMATION FOR SEQ ID NO:28:

(i) SEQUENCE CHARACTERISTICS:
        (A) LENGTH: 15
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (B) LOCATION: NEF 164-178

(xi) SEQUENCE DESCRIPTION: SEQ ID NO:28:

```
Gly Ile Arg Tyr Pro Lys Thr Phe Gly Trp Leu Trp
 1               5                  10
Lys Leu Val
        15
```

(2) INFORMATION FOR SEQ ID NO:29:

(i) SEQUENCE CHARACTERISTICS:
        (A) LENGTH: 14
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: influenza A (ix) FEATURE:
        (A) NAME/KEY: NP1
        (B) LOCATION: NP 50-63

(xi) SEQUENCE DESCRIPTION: SEQ ID NO:29:

```
Ser Asp Tyr Glu Gly Arg Leu Ile Gly Asn Ser Leu
 1               5                  10
Thr Ile
```

(2) INFORMATION FOR SEQ ID NO:30:

(i) SEQUENCE CHARACTERISTICS:
        (A) LENGTH: 15
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: influenza A (ix) FEATURE:
        (A) NAME/KEY: NP3

(B) LOCATION: NP 365-379

(xi) SEQUENCE DESCRIPTION: SEQ ID NO:30:

Ile Ala Ser Asn Glu Asn Met Glu Thr Met Glu Ser
 1               5                  10

Ser Thr Leu
        15

(2) INFORMATION FOR SEQ ID NO:31:

(i) SEQUENCE CHARACTERISTICS:
        (A) LENGTH: 40
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: influenza A (ix) FEATURE:
        (A) NAME/KEY: NP123
        (B) LOCATION: NP 50-63; 147-158; 365-379

(xi) SEQUENCE DESCRIPTION: SEQ ID NO:31:

Ser (v) FRAGMENT TYPE:  internal (vi) ORIGINAL SOURCE:
        (A) ORGANISM: influenza (ix) FEATURE:
        (A) NAME/KEY: L2
        (D) OTHER INFORMATION:  Xaa at position 1 is
            N-acetyl-2-aminohexadecanoic acid; and Xaa
            at position 13 is 2-aminohexadecanoamide (xi) SEQUENCE DESCRIPTION: SEQ ID NO:33:

Xaa Thr Tyr Gln Arg Thr Arg Ala Leu Val Thr Gly
              5                  10

Xaa (2) INFORMATION FOR SEQ ID NO:34:

(i) SEQUENCE CHARACTERISTICS:
        (A) LENGTH: 13
        (B) TYPE:  amino acid
        (C) STRANDEDNESS:  unknown
        (D) TOPOLOGY:  linear (ii) MOLECULE TYPE:  peptide (v) FRAGMENT TYPE:  internal (vi) ORIGINAL SOURCE:
        (A) ORGANISM: influenza (ix) FEATURE:
        (A) NAME/KEY: L3
        (D) OTHER INFORMATION:  Xaa at position 1 is
            N,N'-dipalmitoyllysine; and Xaa at position
            13 is 2-aminohexadecanoamide (xi) SEQUENCE DESCRIPTION: SEQ ID NO:34:

Xaa Thr Tyr Gln Arg Thr Arg Ala Leu Val Thr Gly
              5                  10

Xaa (2) INFORMATION FOR SEQ ID NO:35:

(i) SEQUENCE CHARACTERISTICS:
        (A) LENGTH: 17
        (B) TYPE:  amino acid
        (C) STRANDEDNESS:  unknown
        (D) TOPOLOGY:  linear (ii) MOLECULE TYPE:  peptide (v) FRAGMENT TYPE:  internal (vi) ORIGINAL SOURCE:
        (A) ORGANISM: HIV-1

(ix) FEATURE:
        (A) NAME/KEY: CB1
        (D) OTHER INFORMATION:  Xaa is 2-
            aminohexadecanoamide (xi) SEQUENCE DESCRIPTION: SEQ ID NO:35:

Ile Arg Ile Gln Arg Gly Pro Gly Arg Ala Phe Val
              5                  10

Thr Ile Gly Lys Xaa
         15

(2) INFORMATION FOR SEQ ID NO:36:

```
        (i) SEQUENCE CHARACTERISTICS:
            (A) LENGTH:  18
            (B) TYPE:  amino acid
            (C) STRANDEDNESS:  unknown
            (D) TOPOLOGY:  linear (ii) MOLECULE TYPE:  peptide (v) FRAGMENT TYPE:  internal (vi) ORIGINAL SOURCE:
            (A) ORGANISM: HIV-1

(ix) FEATURE:
            (A) NAME/KEY: CB2
            (D) OTHER INFORMATION:  Xaa at position 1 is
                N-acetyl-2-aminohexadecanoic acid; and Xaa
                at position 18 is 2-aminohexadecanoamide (xi) SEQUENCE DESCRIPTION: SEQ ID NO:36:

Xaa Ile Arg Ile Gln Arg Gly Pro Gly Arg Ala Phe
 1               5                  10

Val Thr Ile Gly Lys Xaa
            15

(2) INFORMATION FOR SEQ ID NO:37:

(i) SEQUENCE CHARACTERISTICS:
            (A) LENGTH:  18
            (B) TYPE:  amino acid
            (C) STRANDEDNESS:  unknown
            (D) TOPOLOGY:  linear (ii) MOLECULE TYPE:  peptide (v) FRAGMENT TYPE:  internal (vi) ORIGINAL SOURCE:
            (A) ORGANISM: HIV-1

(ix) FEATURE:
            (A) NAME/KEY: CB3
            (D) OTHER INFORMATION:  Xaa at position 1 is
                N,N'-dipalmitoyllysine; and Xaa at position
                18 is 2-aminohexadecanoamide (xi) SEQUENCE DESCRIPTION: SEQ ID NO:37:

Xaa Ile Arg Ile Gln Arg Gly Pro Gly Arg Ala Phe
 1               5                  10

Val Thr Ile Gly Lys Xaa
            15

(2) INFORMATION FOR SEQ ID NO:38:

(i) SEQUENCE CHARACTERISTICS:
            (A) LENGTH:  35
            (B) TYPE:  amino acid
            (C) STRANDEDNESS:  unknown
            (D) TOPOLOGY:  linear (ii) MOLECULE TYPE:  peptide (v) FRAGMENT TYPE:  internal (vi) ORIGINAL SOURCE:
            (A) ORGANISM: HIV-1

(ix) FEATURE:
            (A) NAME/KEY: CB6
            (D) OTHER INFORMATION:  Xaa is 2-
                aminohexadecanoamide (xi) SEQUENCE DESCRIPTION: SEQ ID NO:38:
```

```
Thr Arg Pro Asn Asn Asn Thr Arg Lys Ser Ile Arg
 1               5                  10

Ile Gln Arg Gly Pro Gly Arg Ala Phe Val Thr Ile
         15              20

Gly Lys Ile Gly Asn Met Arg Gln Ala His Xaa
 25              30                  35
```

(2) INFORMATION FOR SEQ ID NO:39:

(i) SEQUENCE CHARACTERISTICS:
        (A) LENGTH: 36
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (A) NAME/KEY: CB7
        (D) OTHER INFORMATION: Xaa at position 1 is
            N-acetyl-2-aminohexadecanoic acid; and Xaa
            at position 36 is 2-aminohexadecanoamide (xi) SEQUENCE DESCRIPTION: SEQ ID NO:39:

```
Xaa Thr Arg Pro Asn Asn Asn Thr Arg Lys Ser Ile
 1               5                  10

Arg Ile Gln Arg Gly Pro Gly Arg Ala Phe Val Thr
         15              20

Ile Gly Lys Ile Gly Asn Met Arg Gln Ala His Xaa
 25              30                  35
```

(2) INFORMATION FOR SEQ ID NO:40:

(i) SEQUENCE CHARACTERISTICS:
        (A) LENGTH: 36
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (A) NAME/KEY: CB8
        (D) OTHER INFORMATION: Xaa at position 1 is
            N,N'-dipalmitoyllysine; and Xaa at position
            36 is 2-aminohexadecanoamide (xi) SEQUENCE DESCRIPTION: SEQ ID NO:40:

```
Xaa Thr Arg Pro Asn Asn Asn Thr Arg Lys Ser Ile
 1               5                  10

Arg Ile Gln Arg Gly Pro Gly Arg Ala Phe Val Thr
         15              20

Ile Gly Lys Ile Gly Asn Met Arg Gln Ala His Xaa
 25              30                  35
```

(2) INFORMATION FOR SEQ ID NO:41:

(i) SEQUENCE CHARACTERISTICS:
        (A) LENGTH: 17

(B) TYPE:  amino acid
        (C) STRANDEDNESS:  unknown
        (D) TOPOLOGY:  linear (ii) MOLECULE TYPE:  peptide (v) FRAGMENT TYPE:  internal (vi) ORIGINAL SOURCE:
        (A) ORGANISM:  HIV-1

(ix) FEATURE:
        (A) NAME/KEY:  CB4
        (D) OTHER INFORMATION:  Xaa is N-n-
            palmitoyllysine amide (xi) SEQUENCE DESCRIPTION: SEQ ID NO:41:

Ile Arg Ile Gln Arg Gly Pro Gly Arg Ala Phe Val
 1               5                  10

Thr Ile Gly Lys Xaa
        15

(2) INFORMATION FOR SEQ ID NO:42:

(i) SEQUENCE CHARACTERISTICS:
        (A) LENGTH:  17
        (B) TYPE:  amino acid
        (C) STRANDEDNESS:  unknown
        (D) TOPOLOGY:  linear (ii) MOLECULE TYPE:  peptide (v) FRAGMENT TYPE:  internal (vi) ORIGINAL SOURCE:
        (A) ORGANISM:  HIV-1

(ix) FEATURE:
        (A) NAME/KEY:  CB17
        (D) OTHER INFORMATION:  Xaa is 2-aminohexa-
            decanoic acid (xi) SEQUENCE DESCRIPTION: SEQ ID NO:42:

Xaa Ile Arg Ile Gln Arg Gly Pro Gly Arg Ala Phe
 1               5                  10

Val Thr Ile Gly Lys
        15

(2) INFORMATION FOR SEQ ID NO:43:

(i) SEQUENCE CHARACTERISTICS:
        (A) LENGTH:  16
        (B) TYPE:  amino acid
        (C) STRANDEDNESS:  unknown
        (D) TOPOLOGY:  linear (ii) MOLECULE TYPE:  peptide (v) FRAGMENT TYPE:  internal (vi) ORIGINAL SOURCE:
        (A) ORGANISM:  HIV-1

(ix) FEATURE:
        (A) NAME/KEY:  CB5
        (D) OTHER INFORMATION:  N-terminal amine is
            linked to trimexautide via a succinyl
            linker as shown on page 60 of the
            specification (xi) SEQUENCE DESCRIPTION: SEQ ID NO:43:

Ile Arg Ile Gln Arg Gly Pro Gly Arg Ala Phe Val
 1               5                  10

Thr Ile Gly Lys
        15

(2) INFORMATION FOR SEQ ID NO:44:

(i) SEQUENCE CHARACTERISTICS:
        (A) LENGTH: 16
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (A) NAME/KEY: CB19
        (D) OTHER INFORMATION: N-terminal amine is
            linked to trimexautide via a succinyl-
            Gly linker as shown on page 60 of the
            specification (xi) SEQUENCE DESCRIPTION: SEQ ID NO:44:

Ile Arg Ile Gln Arg Gly Pro Gly Arg Ala Phe Val
1               5                   10
Thr Ile Gly Lys
        15

(2) INFORMATION FOR SEQ ID NO:45:

(i) SEQUENCE CHARACTERISTICS:
        (A) LENGTH: 16
        (B) TYPE: amino acid
        (C) STRANDEDNESS: unknown
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (A) NAME/KEY: CB21
        (D) OTHER INFORMATION: the N-terminal Ile
            is linked directly to trimexautide as
            shown on page 60 in the specification (xi) SEQUENCE DESCRIPTION: SEQ ID NO:45:

Ile Arg Ile Gln Arg Gly Pro Gly Arg Ala Phe Val
1               5                   10
Thr Ile Gly Lys
        15

(2) INFORMATION FOR SEQ ID NO:46:

(i) SEQUENCE CHARACTERISTICS:
        (A) LENGTH: 35
        (B) TYPE: amino acid
        (C) STRANDEDNESS: unknown
        (D) TOPOLOGY: linear (ii) MOLECULE TYPE: peptide (v) FRAGMENT TYPE: internal (ix) FEATURE:
        (A) NAME/KEY: CB25

-continued

```
        (D) OTHER INFORMATION:  C-terminal Lys is
            N-n-palmitoyllysine amide (xi) SEQUENCE DESCRIPTION: SEQ ID NO:46:

Thr Arg Pro Asn Asn Asn Thr Arg Lys Ser Ile Arg
  1               5                  10

Ile Gln Arg Gly Pro Gly Arg Ala Phe Val Thr Ile
             15                  20

Gly Lys Ile Gly Asn Met Arg Gln Ala His Lys
 25                  30                  35
```